United States Patent
Vavvas et al.

(10) Patent No.: US 10,143,703 B2
(45) Date of Patent: *Dec. 4, 2018

(54) TREATING OCULAR NEOVASCULARIZATION

(71) Applicant: Massachusetts Eye & Ear Infirmary, Boston, MA (US)

(72) Inventors: Demetrios Vavvas, Boston, MA (US); Joan W. Miller, Winchester, MA (US); Kimio Takeuchi, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 7 days.

This patent is subject to a terminal disclaimer.

(21) Appl. No.: 15/108,751

(22) PCT Filed: Jan. 2, 2015

(86) PCT No.: PCT/US2015/010046
§ 371 (c)(1),
(2) Date: Jun. 28, 2016

(87) PCT Pub. No.: WO2015/103480
PCT Pub. Date: Jul. 9, 2015

(65) Prior Publication Data
US 2017/0042926 A1 Feb. 16, 2017

Related U.S. Application Data

(60) Provisional application No. 61/922,964, filed on Jan. 2, 2014.

(51) Int. Cl.
| | |
|---|---|
| A61K 31/7056 | (2006.01) |
| A61K 31/683 | (2006.01) |
| C07H 19/052 | (2006.01) |
| C07F 9/117 | (2006.01) |
| A61K 31/436 | (2006.01) |
| A61K 31/155 | (2006.01) |
| A61K 31/4439 | (2006.01) |
| A61K 31/515 | (2006.01) |
| A61K 31/519 | (2006.01) |
| A61K 31/616 | (2006.01) |
| A61K 31/6615 | (2006.01) |
| A61K 31/7004 | (2006.01) |
| A61K 9/00 | (2006.01) |
| A61K 45/06 | (2006.01) |

(52) U.S. Cl.
CPC ........ *A61K 31/7056* (2013.01); *A61K 9/0048* (2013.01); *A61K 31/155* (2013.01); *A61K 31/436* (2013.01); *A61K 31/4439* (2013.01); *A61K 31/515* (2013.01); *A61K 31/519* (2013.01); *A61K 31/616* (2013.01); *A61K 31/6615* (2013.01); *A61K 31/683* (2013.01); *A61K 31/7004* (2013.01); *A61K 45/06* (2013.01); *C07F 9/117* (2013.01); *C07H 19/052* (2013.01)

(58) Field of Classification Search
None
See application file for complete search history.

(56) References Cited

U.S. PATENT DOCUMENTS

| | | | |
|---|---|---|---|
| 6,169,069 B1 | 1/2001 | De Lacharriere et al. | |
| 2005/0187241 A1 | 8/2005 | Wen et al. | |
| 2005/0208102 A1* | 9/2005 | Schultz | A61K 9/0048 424/427 |
| 2007/0082859 A1* | 4/2007 | Stover | A61K 9/0019 514/43 |
| 2008/0306011 A1* | 12/2008 | Tokuda | A61K 31/7004 514/23 |
| 2009/0074786 A1* | 3/2009 | Dor | A61K 31/436 424/141.1 |

FOREIGN PATENT DOCUMENTS

| | | | | |
|---|---|---|---|---|
| WO | WO98/055059 | 12/1998 | | |
| WO | WO03/027275 | 4/2003 | | |
| WO | WO2007/017512 | * 2/2007 | .......... | A61K 31/519 |
| WO | WO10/118419 | 10/2010 | | |
| WO | WO2011/098801 | * 8/2011 | .......... | A61K 31/192 |

OTHER PUBLICATIONS

U.S. Appl. No. 15/624,172, filed Jun. 2017, Vavvas et al.*
Ho et al., "Cytosolic phospholipase A2-alpha is an early apoptotic activator in PEDF-induced endothelial cell apoptosis" Am J Physiol Cell Physiol (2009) vol. 296, pp. C273-C284 (Year: 2009).*
Feng et al., "The Regulation of AMPK B1, TSC2, and PTEN Expression by p53: Stress, Cell and Tissue Specificity, and the Role of These Gene Products in Modulating the IGF-1-AKT-mTOR Pathways" Cancer Research (2007) vol. 67 No. 7 pp. 3043-3053 (Year: 2007).*
Kim et al., "Metformin inhibits inflammatory response via AMPK-PTEN pathway in vascular smooth muscle cells" Biochemical and Biophysical Research Communications (2012) vol. 425 pp. 866-872 (Year: 2012).*
Silverman et al., "The Organic Chemistry of Drug Design and Drug Action" Published 1992 by Academic Press chapter 2 pp. 4-47 (Year: 1992).*
Kalariya et al., "Antidiabetic Drug Metformin Suppresses Endotoxin-Induced Uveitis in Rats" Investigative Ophthamology and Visual Science (2012) vol. 53 No. 7 pp. 3431-3440 (Year: 2012).*
Kovach et al., "Anti-VEGF Treatment Strategies for Wet AMD" Journal of Ophthamology, vol. 2012, pp. 1-7 (Year: 2012).*

(Continued)

*Primary Examiner* — Eric Olson
(74) *Attorney, Agent, or Firm* — Fish & Richardson P.C.

(57) ABSTRACT

Methods of treating ocular neovascularization, e.g., associated with wet agerelated macular degeneration (AMD), using activators of AMP-activated protein kinase (AMPK) and/or of Phosphatase and tensin homolog deleted on chromosome 10 (PTEN).

12 Claims, 45 Drawing Sheets
Specification includes a Sequence Listing.

(56) References Cited

OTHER PUBLICATIONS

Uchiyama et al., "An ophthalmic solution of a peroxisome proliferator-activated receptor gamma agonist prevents corneal inflammation in a rat alkali burn model" Molecular Vision vol. 19 pp. 2135-2150 (Year: 2013).*

Suzuki et al., "Aminoimidazole Carboxamide Ribonucleotide Ameliorates Experimental Autoimmune Uveitis" Immunology and Microbiology vol. 53 pp. 4158-4169 (Year: 2012).*

Meric-Bernstam F et al. PIK3CA/PTEN mutations and Akt activation as markers of sensitivity to allosteric mTOR inhibitors. Clin Cancer Res, 2012, 18(6), (abstract) [online] [retrieved on May 19, 2015]. Retrieved from the PubMed, PMID: 22422409.

International Search Report and Written Opinion dated May 21, 2015 from corresponding application PCT/US2015/010046.

Bora et al., "CD59, a complement regulatory protein, controls choroidal neovascularization in a mouse model of wet-type age-related macular degeneration," The Journal of Immunology, 178(3): 1783-1790, Jan. 2007.

Cheung et al., "Regulation of caveolin-1 expression and phosphorylation by VEGF in ovine amnion cells," Reproductive Sciences (Thousand Oaks, Calif.), 17(12): 1112-1119, Dec. 2010.

European Search Report in Application No. 15733311.3, dated Aug. 25, 2017.

Huxlin et al., "Topical rosiglitazone is an effective anti-scarring agent in the cornea," PLOS One, 8(8): e70785, 2013.

Hyttinen et al., "5'-Adenosine monophosphate-activated protein kinase—mammalian target of rapamycin axis as therapeutic target for age-related macular degeneration," Rejuvenation Research, 14(6): 651-660, Dec. 2011.

Iwasaki et al., "AMP-activated protein kinase as a promoting factor, but complement and thrombin as limiting factors for acquisition of cytoprotection: implications for induction of accommodation," Transplant International: Official Journal of the European Society for Organ Transplantation, 26(11): 1138-1148, Nov. 2013.

Lu et al., "Quercetin activates AMP-activated protein kinase by reducing PP2C expression protecting old mouse brain against high cholesterol-induced neurotoxicity," The Journal of Pathology, 222(2): 199-212, Oct. 2010.

Meric-Bernstam et al., "PIK3CA/PTEN mutations and Akt activation as markers of sensitivity to allosteric mTOR inhibitors." Clin Cancer Res, 2012, 18(6), (abstract).

Soheilian et al., "Pilot study of safety and effect of combined intravitreal bevacizumab and methotrexate for neovascular age-related macular degeneration," European Journal of Opthalmology, 21(1): 77-82, Jan. 2011.

Takeuchi et al., "AMP-dependent kinase inhibits oxidative stress-induced caveolin-1 phosphorylation and endocytosis by suppressing the dissociation between c-Abl and Prdx1 proteins in endothelial cells," The Journal of Biological Chemistry, 288(28): 20581-20591, Jul. 2013.

Theodoropoulou et al., "Aminoimidazole carboxamide ribonucleotide (AICAR) inhibits the growth of retinoblastoma in vivo by decreasing angiogenesis and including apoptosis," PLOS One, 8(1): e52852, 2013.

Zhuang et al., "Effect of quercetin on formation of choroidal neovascularization (CNV) in age-related macular degeneration (AMD)," Eye Science, 26(1): Mar. 23-29, 2011.

* cited by examiner

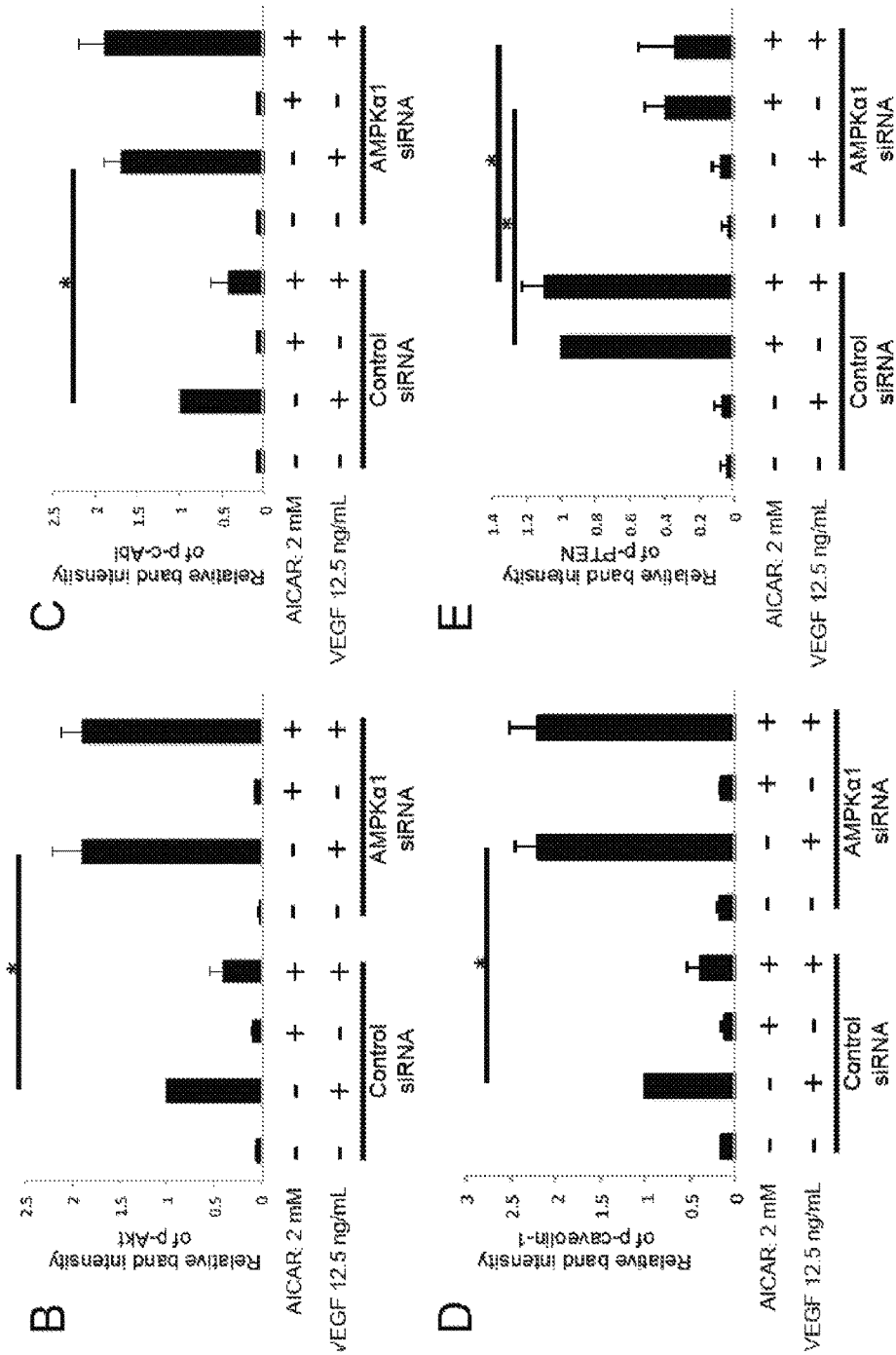
FIGs. 13B-E

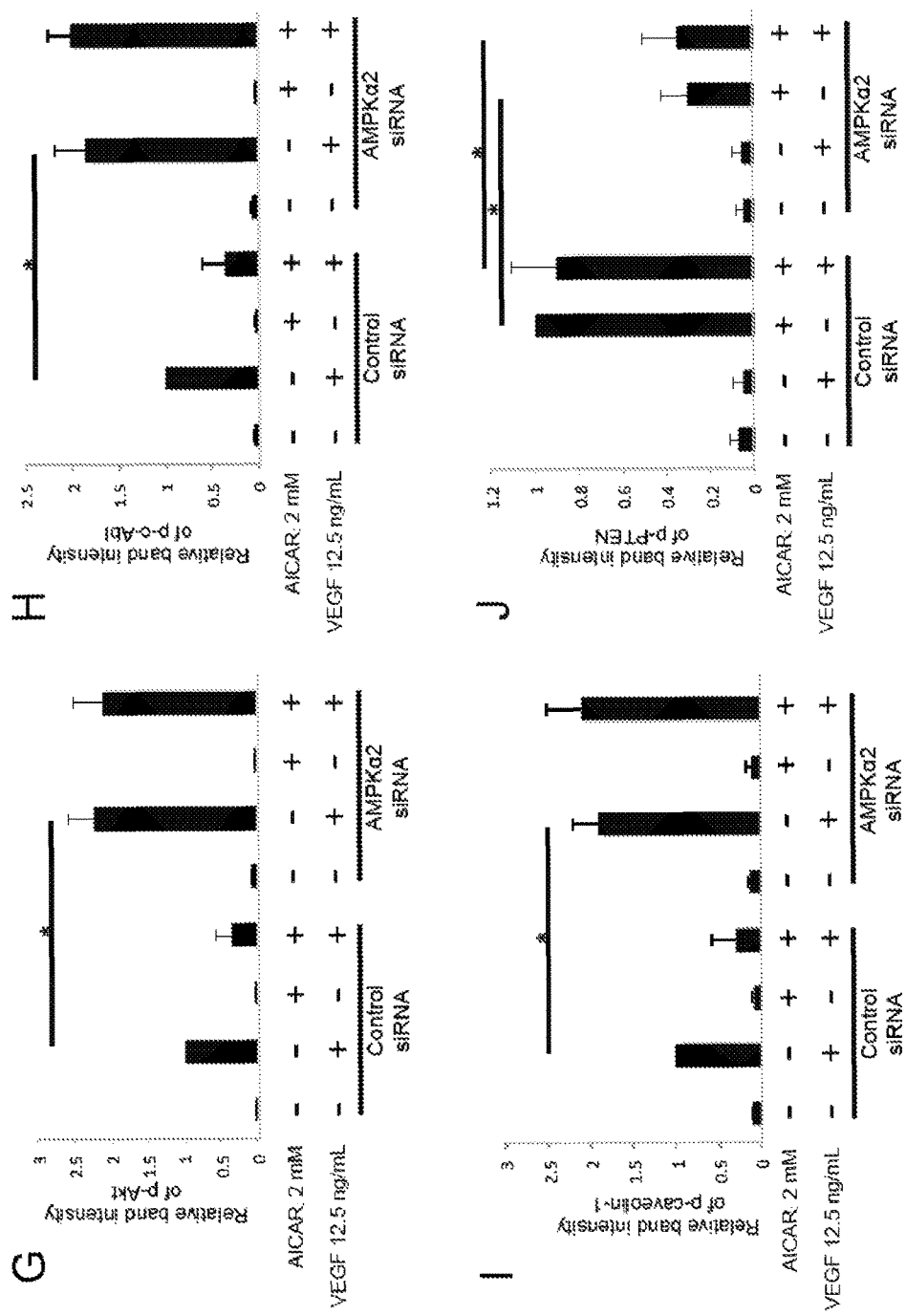
FIGs. 13G-J

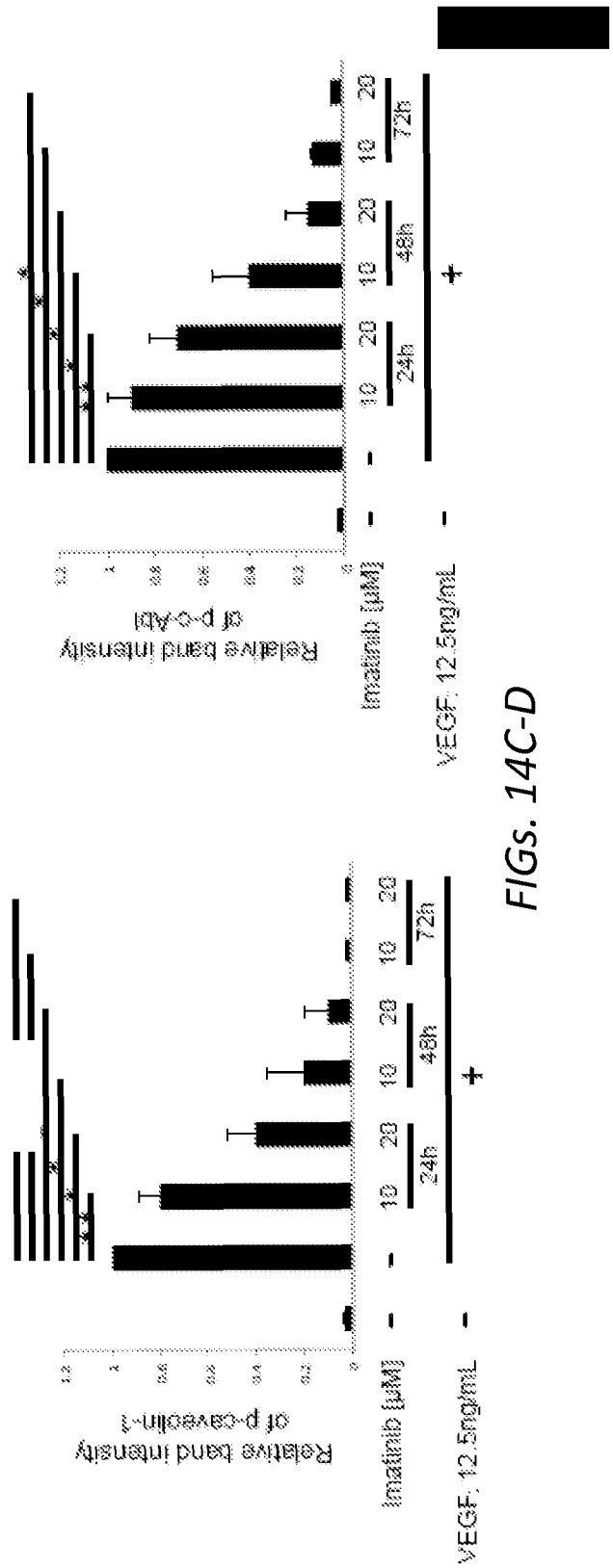
FIGs. 14C-D

SEQUENCE LISTING

```
<160> NUMBER OF SEQ ID NOS: 4

<210> SEQ ID NO 1
<211> LENGTH: 19
<212> TYPE: RNA
<213> ORGANISM: Artificial Sequence
<220> FEATURE:
<223> OTHER INFORMATION: alpha1 PRKAA1 siRNA

<400> SEQUENCE: 1
ccauacccuu gaugaauua                                              19

<210> SEQ ID NO 2
<211> LENGTH: 19
<212> TYPE: RNA
<213> ORGANISM: Artificial Sequence
<220> FEATURE:
<223> OTHER INFORMATION: alpha2 PRKAA2 siRNA

<400> SEQUENCE: 2
cgacuaagcc caaaucuuu                                              19

<210> SEQ ID NO 3
<211> LENGTH: 19
<212> TYPE: RNA
<213> ORGANISM: Artificial Sequence
<220> FEATURE:
<223> OTHER INFORMATION: alpha1prime PRKAA1 siRNA

<400> SEQUENCE: 3
gcccagaggu agauauaug                                              19

<210> SEQ ID NO 4
<211> LENGTH: 19
<212> TYPE: RNA
<213> ORGANISM: Artificial Sequence
<220> FEATURE:
<223> OTHER INFORMATION: alpha2prime PRKAA2 siRNA

<400> SEQUENCE: 4
gagcauguac cuacguuau                                              19
```

TREATING OCULAR NEOVASCULARIZATION

CLAIM OF PRIORITY

This application is a 371 U.S. National Phase Application of PCT/US2015/010046, filed on Jan. 2, 2015, which claims the benefit of U.S. Patent Application Ser. No. 61/922,964, filed on Jan. 2, 2014. The entire contents of the foregoing are hereby incorporated by reference.

FEDERALLY SPONSORED RESEARCH OR DEVELOPMENT

This invention was made with Government support under Grant No. EY014104 awarded by the National Eye Institute of the National Institutes of Health. The Government has certain rights in the invention.

TECHNICAL FIELD

This invention relates to methods of treating ocular neovascularization using activators of AMP-activated protein kinase (AMPK) and/or of Phosphatase and tensin homolog deleted on chromosome 10 (PTEN).

BACKGROUND

Age-related macular degeneration (AMD) is the primary cause of blindness in elderly individuals of industrialized countries (Lim et al. (2012) Lancet. 379, 1728-1738; Zhang et al. (2012) Nat. Rev. Drug Discov. 11, 541-559), and has a projected 50% increase by the year 2020 in the United States (Friedman et al. (2004) Arch. Ophthalmol. 122, 564-572). There is an urgent need for new pharmacological interventions that are safe over the long term for the treatment or prevention of AMD.

SUMMARY

The studies described herein connect AMPK activation to two VEGF-mediated pathological processes in ocular neovascularization—vascular tube formation and vascular leakage. Examples 1 and 2 describe AMPK activation as inhibiting vascular tube formation and also as inhibiting vascular leakage in in vitro experiments. Thus, in one embodiment the present invention includes the use of an AMPK activator (e.g., AICAR) to treat pathological ocular neovascularization, e.g., in AMD. In addition, Example 2 demonstrates that AMPK activation inhibits VEGF-induced tube formation through PTEN dependent dephosphorylation of Akt; thus, in another aspect the invention provides methods for reducing VEGF-induced neovascularization in vivo, e.g., neovascularization associated with AMD, by administering a PTEN activator.

Thus in a first aspect the invention provides methods for reducing or delaying ocular neovascularization in a mammal, the method comprising:
identifying a mammal in need of reduced or delayed ocular neovascularization; and
administering to the mammal an effective amount of an amp-activated protein kinase (AMPK) activator and/or Phosphatase and tensin homolog deleted on chromosome 10 (PTEN) activator sufficient to reduce or delay ocular neovascularization in the mammal.

In another aspect the invention provides methods for treating wet age-related macular degeneration (AMD) in a mammal, the method comprising:
identifying a mammal who has wet AMD; and
administering to the mammal a therapeutically effective amount of an amp-activated protein kinase (AMPK) activator and/or Phosphatase and tensin homolog deleted on chromosome 10 (PTEN) activator.

In another aspect the invention provides an amp-activated protein kinase (AMPK) activator and/or Phosphatase and tensin homolog deleted on chromosome 10 (PTEN) activator to reduce ocular neovascularization in a mammal.

In another aspect the invention provides for the use of an amp-activated protein kinase (AMPK) activator and/or Phosphatase and tensin homolog deleted on chromosome 10 (PTEN) activator in the manufacture of a medicament to reduce IOP in a mammal.

In some embodiments, the mammal has wet age-related macular degeneration, retinopathy (selected from a group comprising of: retinopathy of prematurity (ROP); diabetic retinopathy; retina vein occlusion; sickle cell retinopathy; Stargardt's disease; choroidal neovascularization, radiation retinopathy), symptoms associated with microangiopathy, neovascular glaucoma, corneal graft rejection, glaucoma, herpetic and infectious keratitis, ocular ischemia, neovascular glaucoma, corneal, uveal and iris neovascularization, orbital and eyelid tumors, Stevens Johnson Syndrome, ocular cicatricial pemphigoid, wounds or other injuries (e.g., chemical injuries due to exposure to irritants, acids or bases), and ocular surface diseases.

In some embodiments, the disorder is characterized by surface, corneal, retinal, choroidal, uveal, or iris neovascularization.

In some embodiments, the mammal has endophthalmitis (e.g., the endogenous form and the exogenous form), macular edema (e.g., macular edema that occurs as a result of age-related macular degeneration, cataract surgery, diabetes, drug toxicity, eye injury, retinal vein occlusion (e.g., central retinal vein occlusion (CRVO) and branch retinal vein occlusion), or other inflammatory eye diseases, e.g., pseudophakic macular edema), conjunctivitis, episcleritis, keratitis, optic neuritis, orbital pseudotumor, retinal vasculitis, scleritis, and uveitis (e.g., (i) uveitis associated with sepsis (e.g., LPS-induced uveitis); (ii) autoimmune uveitis (e.g., uveitis associated with lupus); or (iii) uveitis associated with type II, type III, type IV, or type V hypersensitivity reactions).

In some embodiments, the AMPK activator is selected from the group consisting of 5-Aminoimidazole-4-carboxamide riboside (AICA riboside or AICAR); ZMP; guanidine; galegine; metformin (dimethylbiguanide); phemformin (phenethylbiguanide); antifolate drugs that inhibit AICAR transformylase (e.g., methotrexate, pemetrexed); thiazolidinediones (e.g., rosiglitazone, pioglitazone, or troglitazone); 2-Deoxyglucose (2DG); phenobarbital; A-769662; PT1; and salicylate.

In some embodiments, the PTEN activator is selected from the group consisting of di-C8-phosphatidylinositol 4,5-P2 (PI(4,5)P2 and PI(5)P; PPARgamma agonists such as rosiglitazone; and mTOR inhibitors including rapamycin and its chemical analogues such as temsirolimus, everolimus, and AP-2357.

In some embodiments, the AMPK activator and/or PTEN activator is administered in combination with another treatment such as anti VEGF therapies, non-steroidal or steroidal anti-inflammatory treatments, or neuroprotective treatments.

In another aspect the invention provides a pharmaceutical composition comprising a PTEN activator formulated for ocular administration. In some embodiments, the composition is formulated for topical ocular administration, e.g., as eye drops, topical eye cream, or topical eye lotion. In some embodiments, the formulation comprises microcapsules, microemulsions, or nanoparticles.

In another aspect the invention provides container for drop-wise dispensation of a pharmaceutical composition into the eye of a subject, the container having disposed therein an amount of a PTEN activator.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

A, Cells were cultured in AICAR (2 mM) containing medium for 2 h, and then stimulated with each different concentration (0, 0.5, 1.0, 2.0 mM) of $H_2O_2$ for 30 min. The amounts of p-caveolin-1 and p-c-Abl in HUVEC were then examined by western blotting.

Figure 1A:
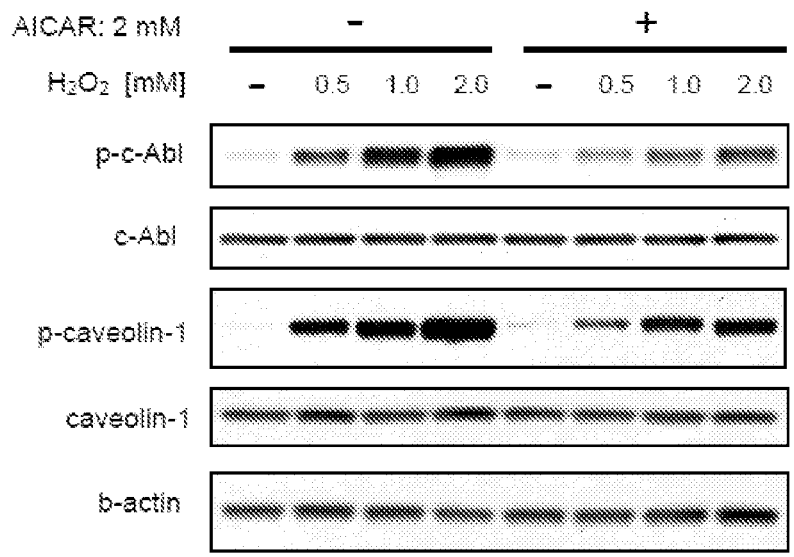
FIG. 1. AICAR suppresses phosphorylation of caveolin-1 and c-Abl, and albumin endocytosis under oxidative stress.
Figure 1B:
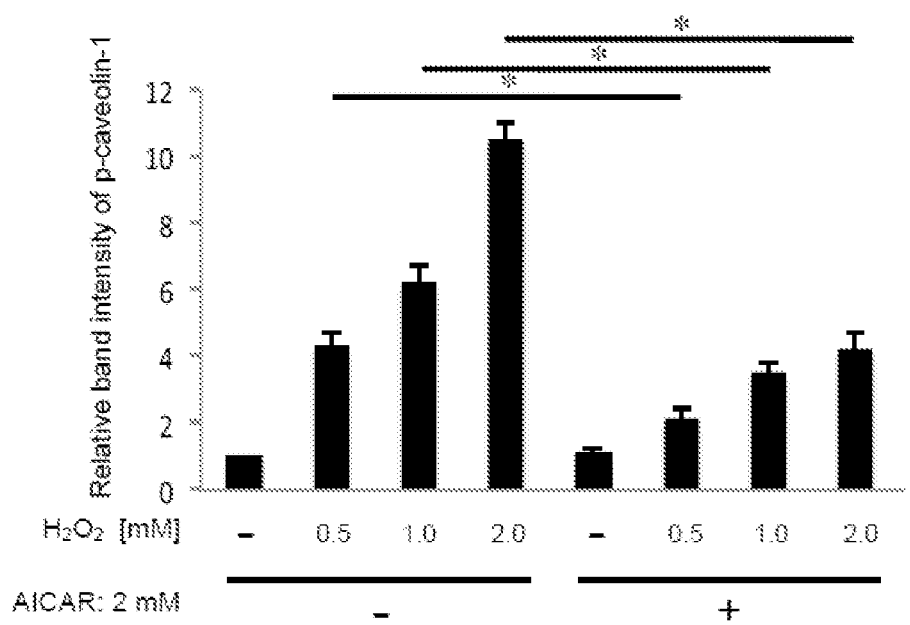
Figure 1C:
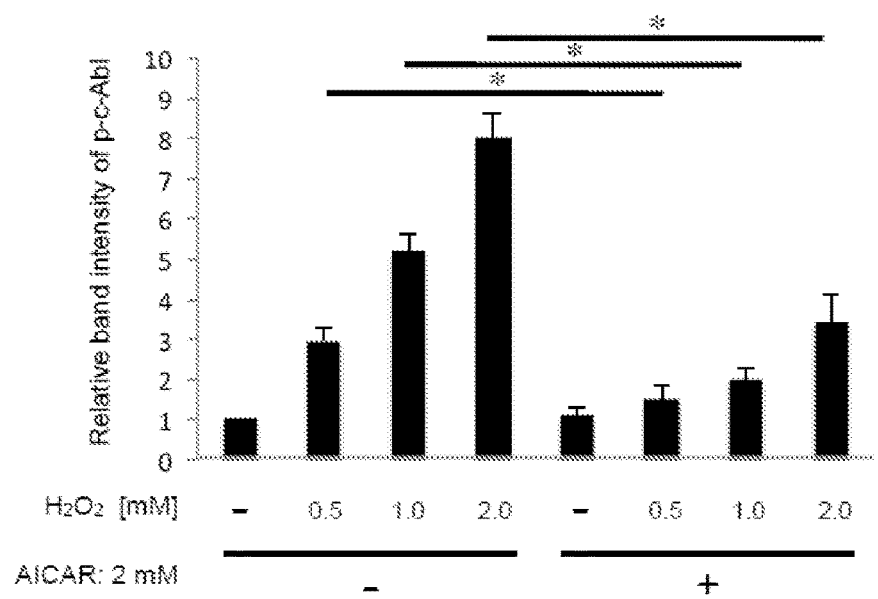

B, Densitometry of p-caveolin-1 in FIG. 1A.

C, Densitometry of p-c-Abl in FIG. 1A.

D, Albumin endocytosis assay. Cells were exposed to Alexa555 conjugated BSA. a, control (untreated cells), b, $H_2O_2$ (2 mM) stimulation for 30 min, c, Pretreated with AICAR (2 mM) for 2 h, d, Pretreated with AICAR for 2 h followed by $H_2O_2$ (2 mM) stimulation for 30 min. BSA conjugated with Alexa 555 (red), p-caveolin (green), VE-cadherin (blue). Scale bar=50 μm.

A, Representative blots are shown. *, P<0.01.

FIG. 2. AICAR inhibits $H_2O_2$ induced phosphorylation of caveolin-1 via activation of AMPK.

A, Cells were treated with each concentration of AICAR for 2 h.

B, Cells were treated with each concentration of DPY for 1 h, and then stimulated with 2 mM of AICAR for 2 h.

C, Cells were treated with Adenosine transporter inhibitor DPY (8 μM) for 1 h, and then stimulated with 2 mM of AICAR for 2 h, followed by $H_2O_2$ (2 mM) stimulation for 30 min.

Figure 2A:
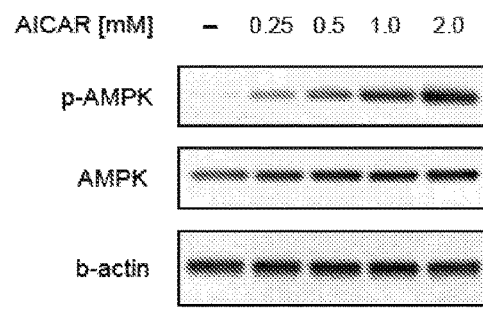
Figure 2B:
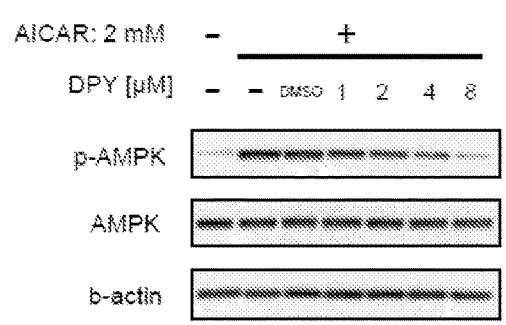
Figure 2C:
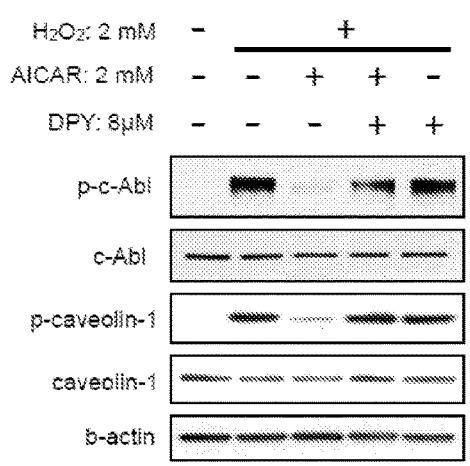
Figure 2D:
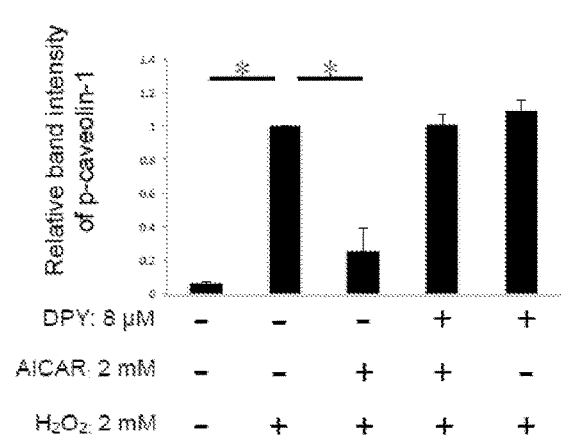
Figure 2E:
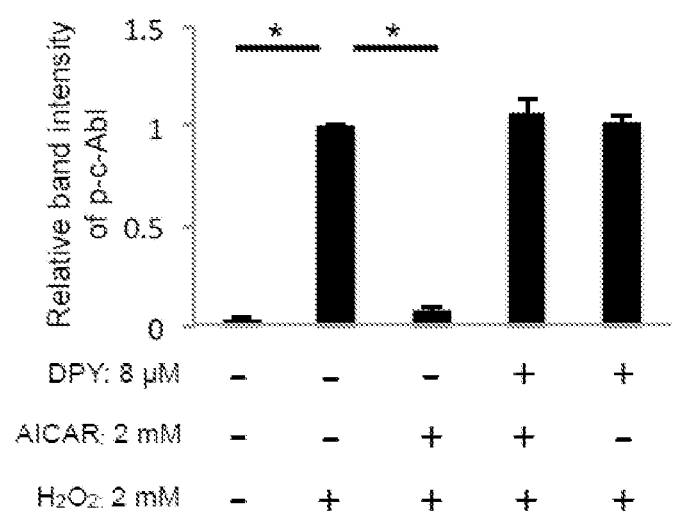
Figure 2F:
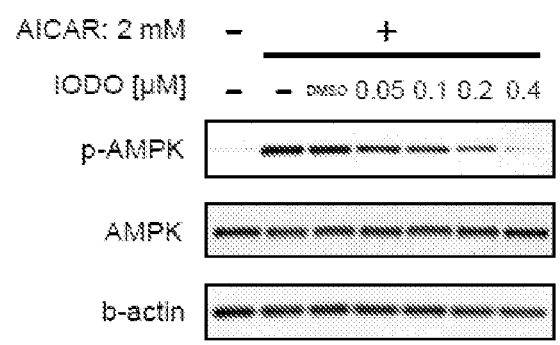

D, Densitometry of p-caveolin-1 in FIG. 2C.

E, Densitometry of p-c-Abl in FIG. 2C.

F, Cells were treated with each concentration of adenosine kinase inhibitor IODO for 1 h, and then stimulated with 2 mM of AICAR for 2 h.

G, Cells were treated with 0.4 μM of IODO for 1 h, and then stimulated with 2 mM of AICAR for 2 h, followed by $H_2O_2$ (2 mM) stimulation for 30 min.

Figure 2G:
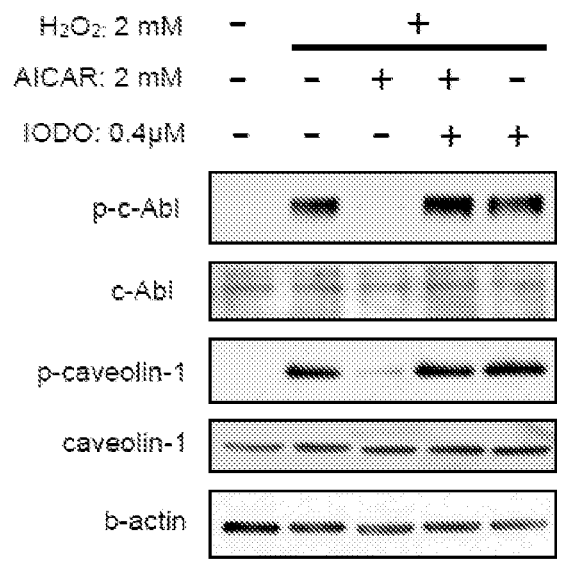
Figure 2H:
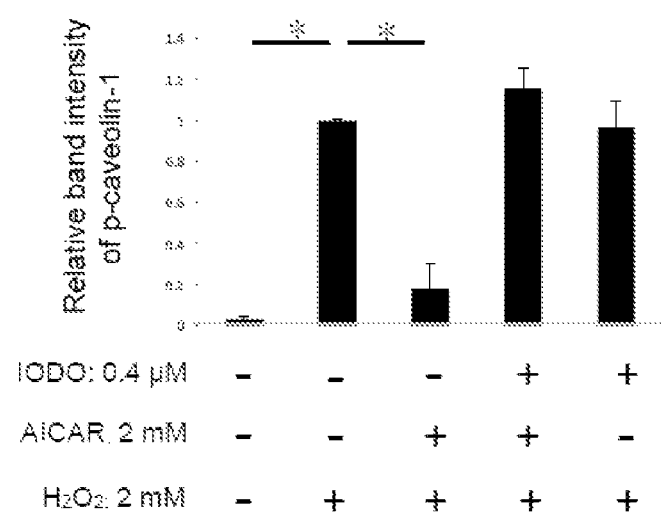
Figure 2I:
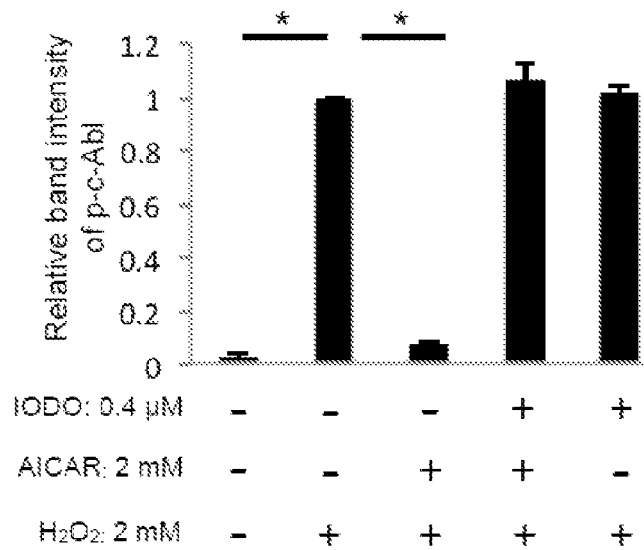

H, Densitometry of p-caveolin-1 in FIG. 2G.

I, Densitometry of p-c-Abl in FIG. 2G.

A-E, Representative blots are shown. *, P<0.01.

FIG. 3. Both AMPKα1 and α2 isoforms are required for AICAR inhibition of caveolin-1 phosphorylation under oxidative stress.

A,D, The amounts of p-caveolin-1 and p-c-Abl in HUVEC were examined by western blotting. Cells were transfected with siRNA against AMPKα1 (A) or α2 (D). Three days after transfection, cells were stimulated with 2 mM of AICAR for 2 h, followed by $H_2O_2$ (2 mM) stimulation for 30 min.

Figure 3A:
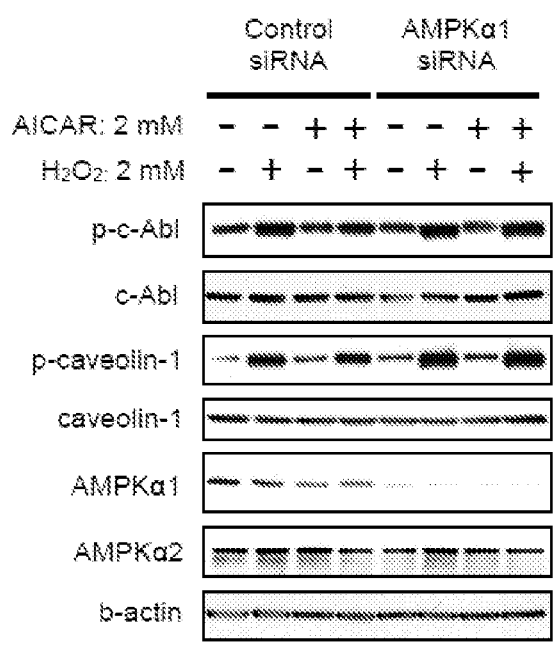
Figure 3B:
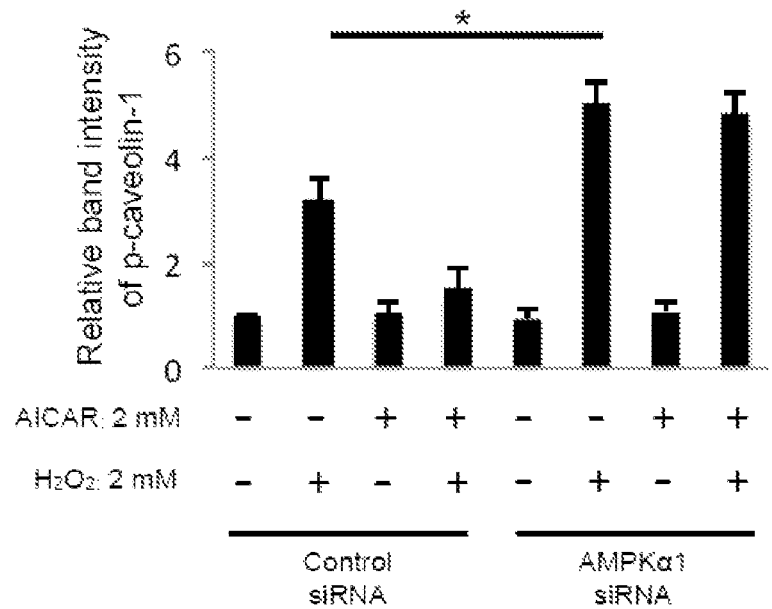
Figure 3C:
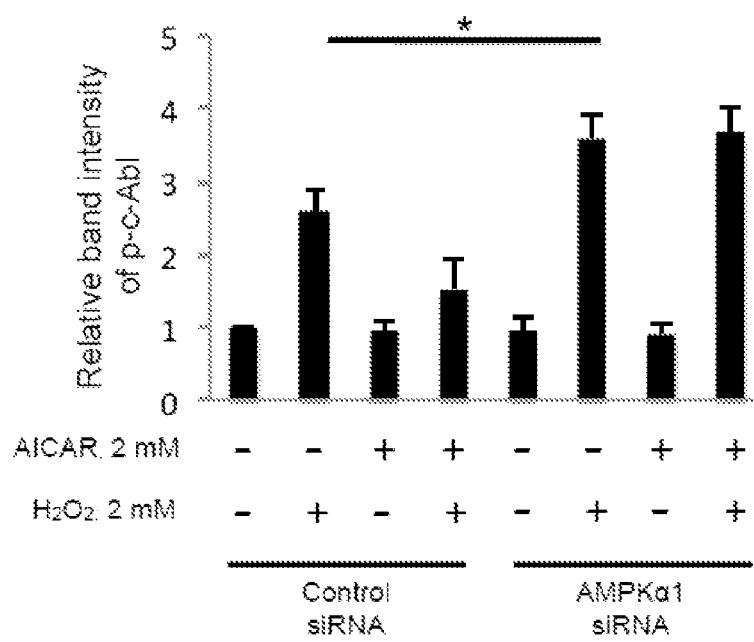

B, Densitometry of p-caveolin-1 in FIG. 3A.

C, Densitometry of p-c-Abl in FIG. 3A.

Figure 3D:
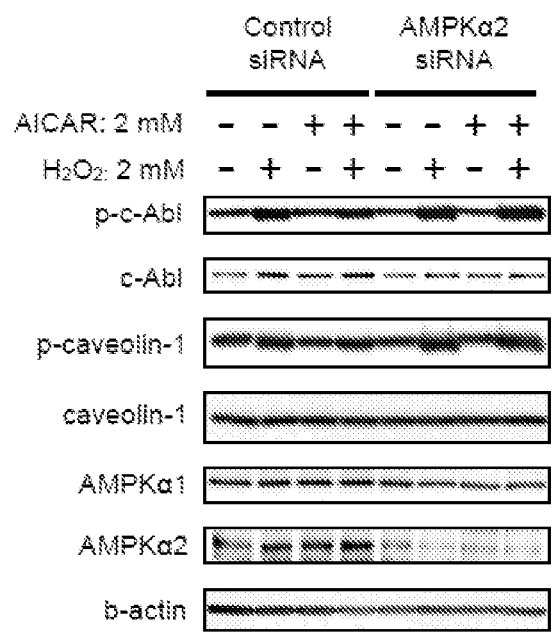
Figure 3E:
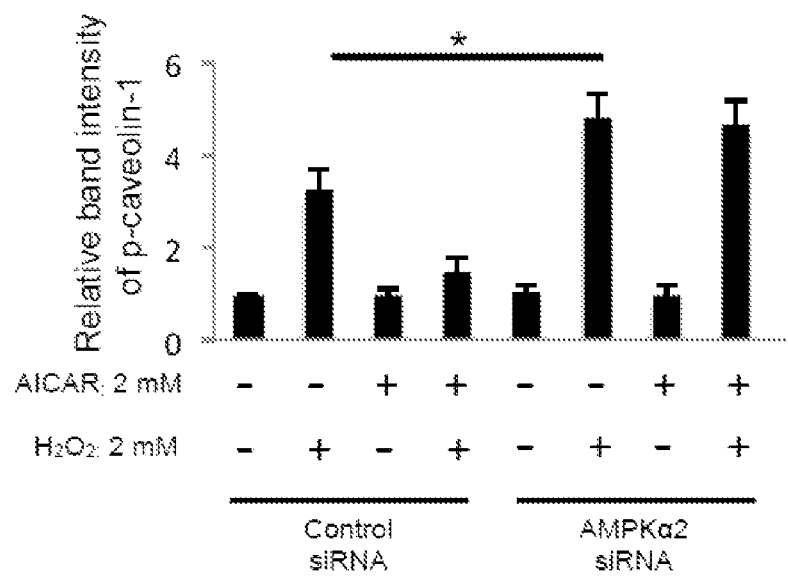
Figure 3F:
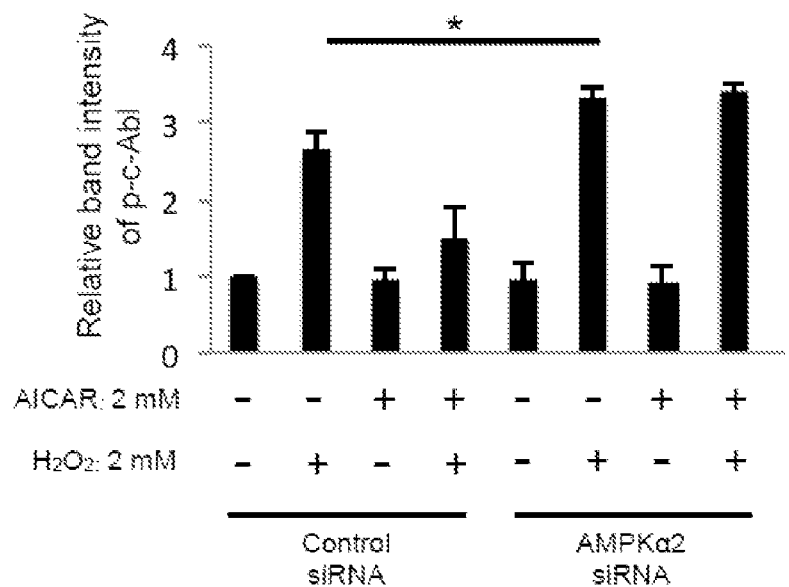

E, Densitometry of p-caveolin-1 in FIG. 3D.

F, Densitometry of p-c-Abl in FIG. 3D.

A & B, Representative blots are shown. *, P<0.01.

FIG. 4. AMPK mediates AICAR effects on c-Abl and caveolin1 phosphorylation

A, Cells were co-transfected with both AMPKα1 and α2 siRNAs (two independent oligos) (α1 (PRKAA1)-CCAUACCCUUGAUGAAUUA (SEQ ID NO:1), α2 (PRKAA2)-CGACUAAGCCCAAAUCUUU (SEQ ID NO:2)). Three days after transfection, cells were stimulated with 2 mM of AICAR for 2 h, followed by $H_2O_2$ (2 mM) stimulation for 30 min. The amounts of p-c-Abl, p-caveolin-1 were examined by western blotting.

Figure 4A:
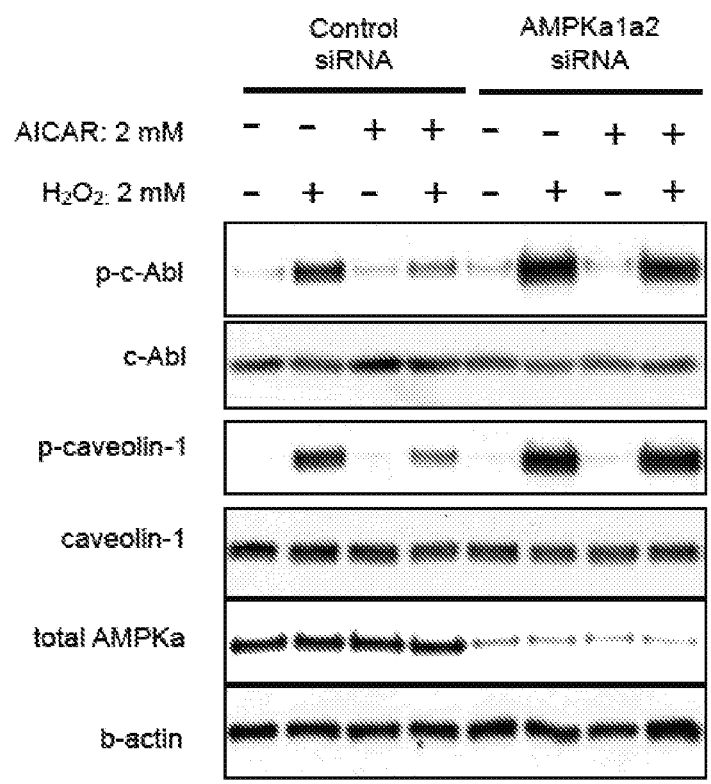
Figure 4B:
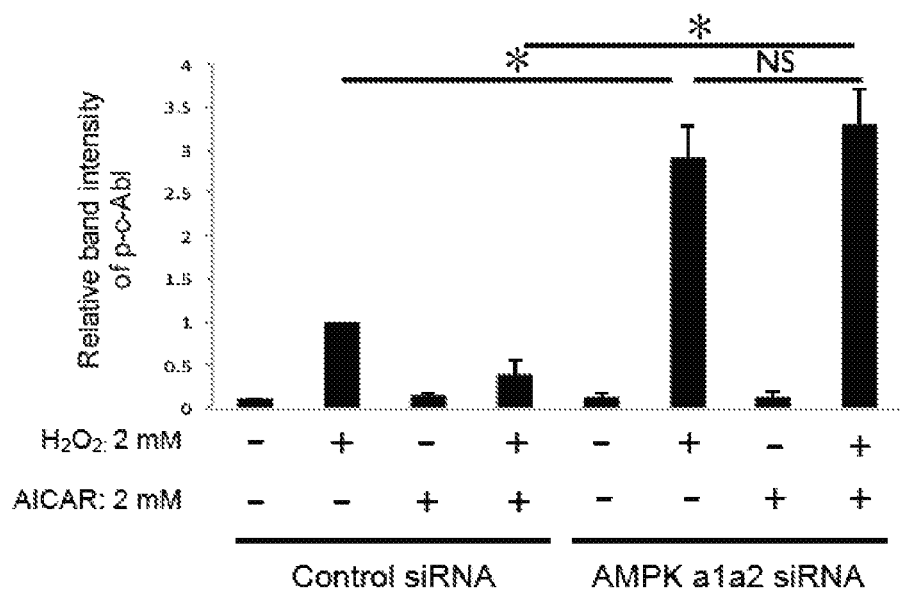
Figure 4C:
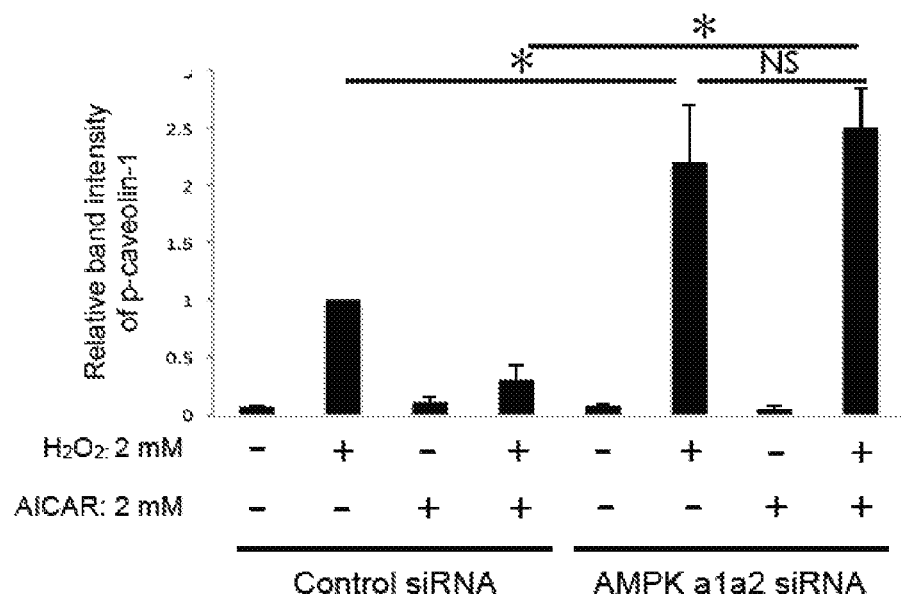

B, Densitometry of p-c-Abl in FIG. 4A.

C, Densitometry of p-caveolin-1 in FIG. 4A.

D, Cells were co-transfected with both AMPKα1 and α2 siRNAs (two independent oligos). (α1' (PRKAA1)-GCCAGAGGUAGAUAUAUG (SEQ ID NO:3), α2' (PRKAA2)-GAGCAUGUACCUACGUUAU (SEQ ID NO:4)). Three days after transfection, cells were stimulated with 2 mM of AICAR for 2 h, followed by $H_2O_2$ (2 mM) stimulation for 30 min. The amounts of p-c-Abl, p-caveolin-1 were examined by western blotting.

Figure 4D:
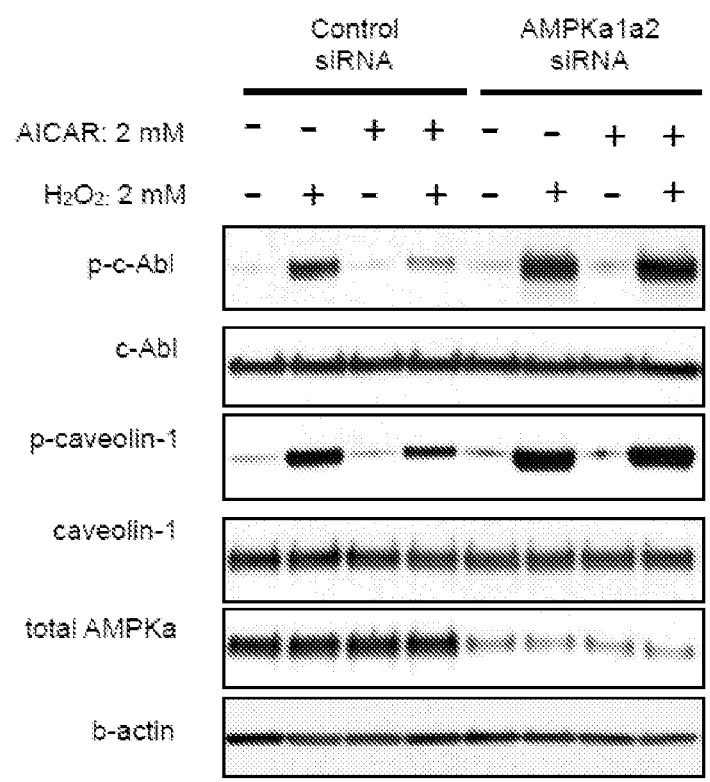
Figure 4E:
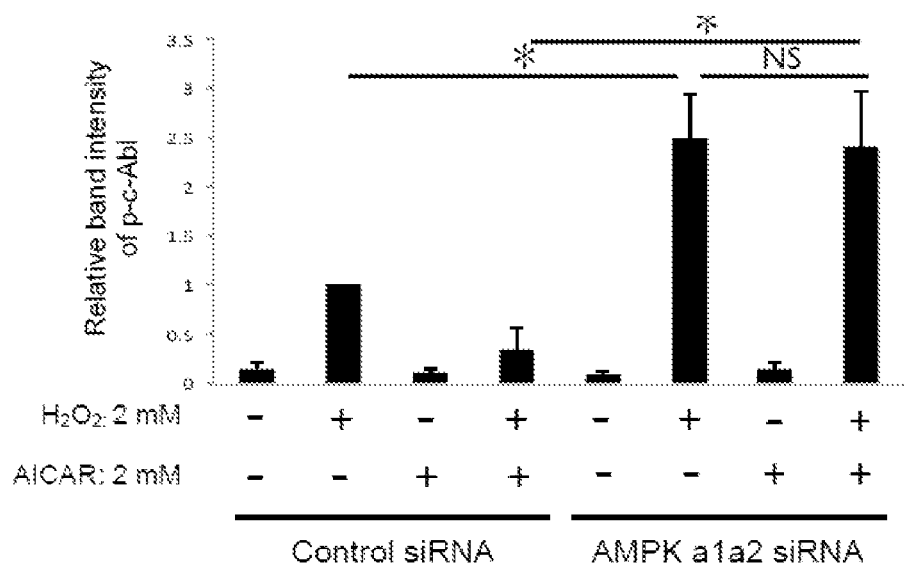
Figure 4F:
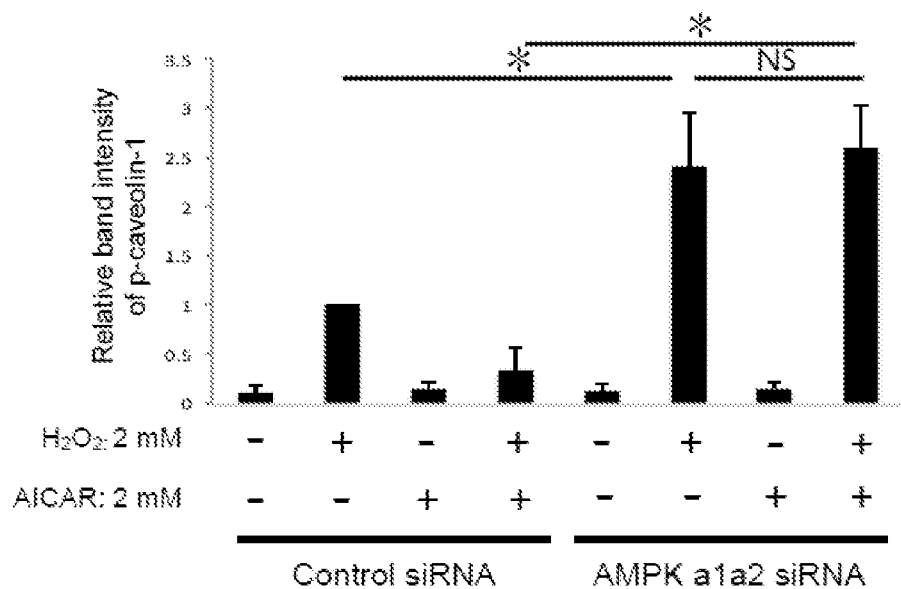

E, Densitometry of p-c-Abl in FIG. 4D.

F, Densitometry of p-caveolin-1 in FIG. 4D.

A & D, Representative blots are shown. *, P<0.01; NS, not significant.

FIG. 5. Inhibitory effect of AMPK on caveolin-1 phosphorylation under oxidative stress is dependent on c-Abl.

A, Cells were treated with 10 or 20 uM of imatinib mesylate for 24, 48 or 72 h before stimulation with $H_2O_2$ (2 mM) for 30 min.

Figure 5A:
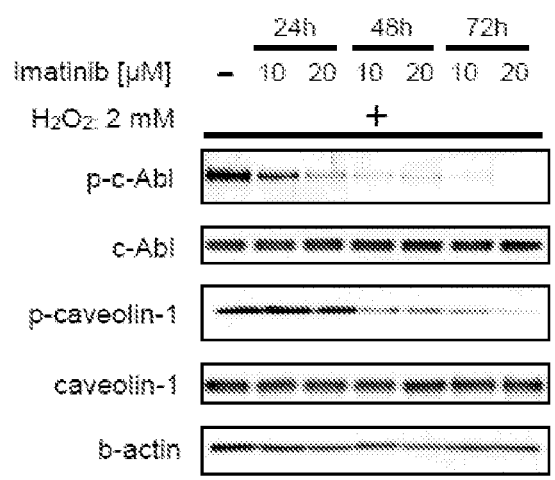
Figure 5B:
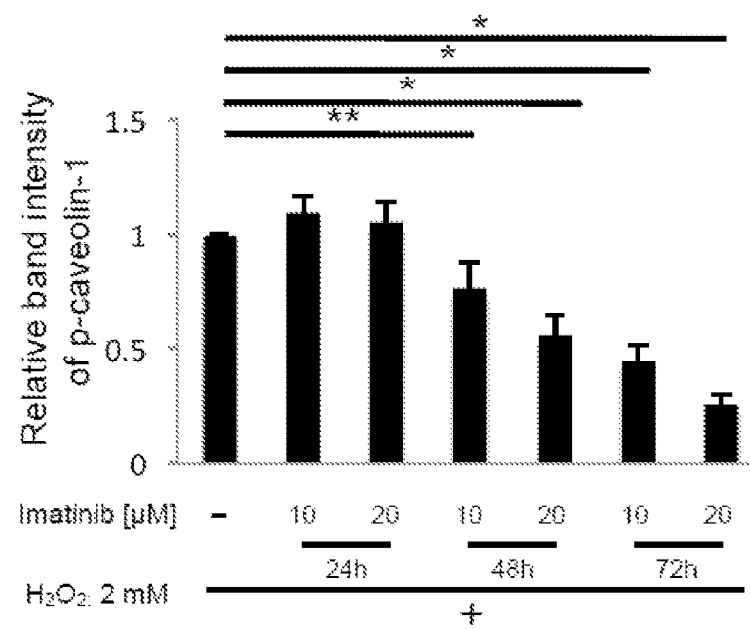
Figure 5C:
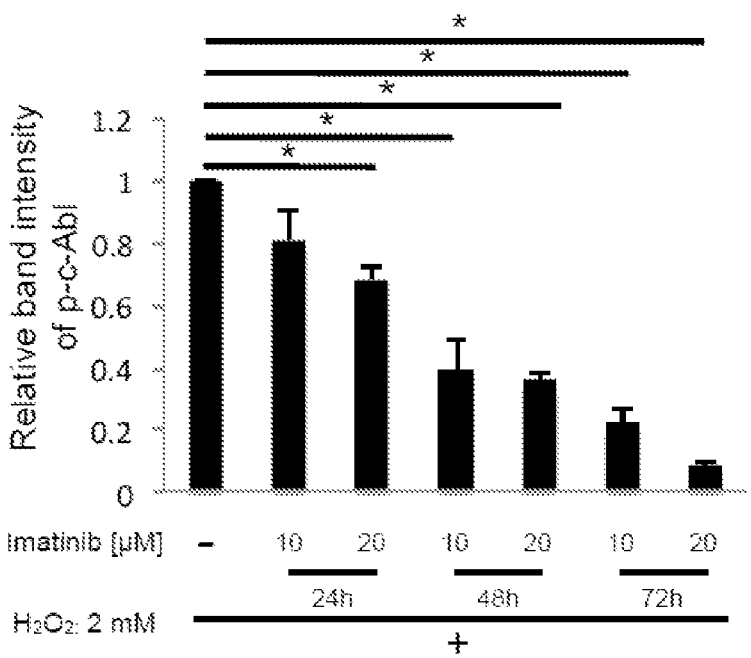

B, Densitometry of p-caveolin-1 in FIG. 5A.

C, Densitometry of p-c-Abl in FIG. 5A.

D, Cells were transfected with siRNA against c-Abl. Three days after transfection, cells were stimulated with 2 mM of AICAR for 2 h, followed by stimulation with $H_2O_2$ (2 mM) for 30 min.

E, Densitometry of p-caveolin-1 in FIG. 4, B.

A & D, Representative blots are shown. *, P<0.01; NS, not significant.

FIG. 6. AICAR inhibits caveolin-1 phosphorylation under oxidative stress by suppressing the dissociation between prdx1 and c-Abl.

A, Cells were transfected with siRNA against prdx1. Three days after transfection, cells were stimulated with 2 mM of AICAR for 2 h, followed by $H_2O_2$ (2 mM) stimulation for 30 min. The amounts of p-c-Abl, p-caveolin-1 were examined by western blotting.

Figure 6A:
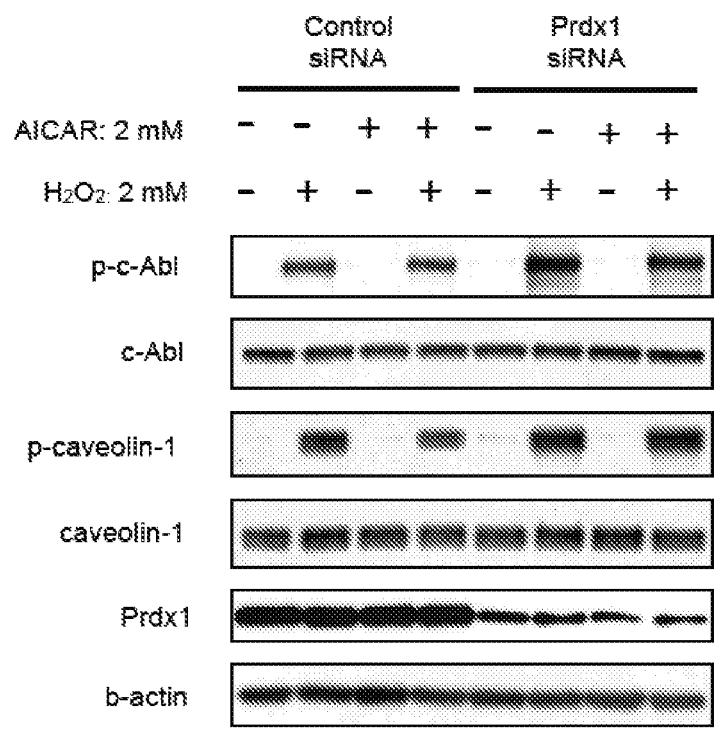
Figure 6B:
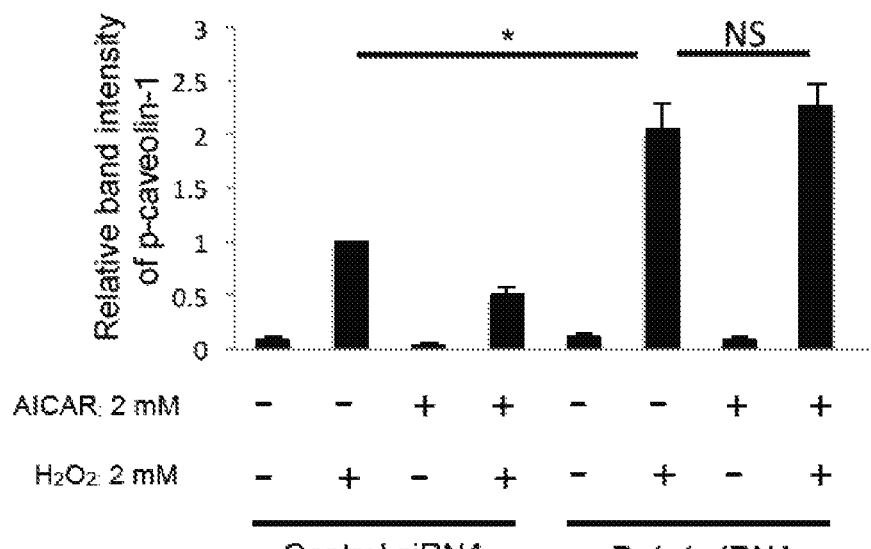
Figure 6C:
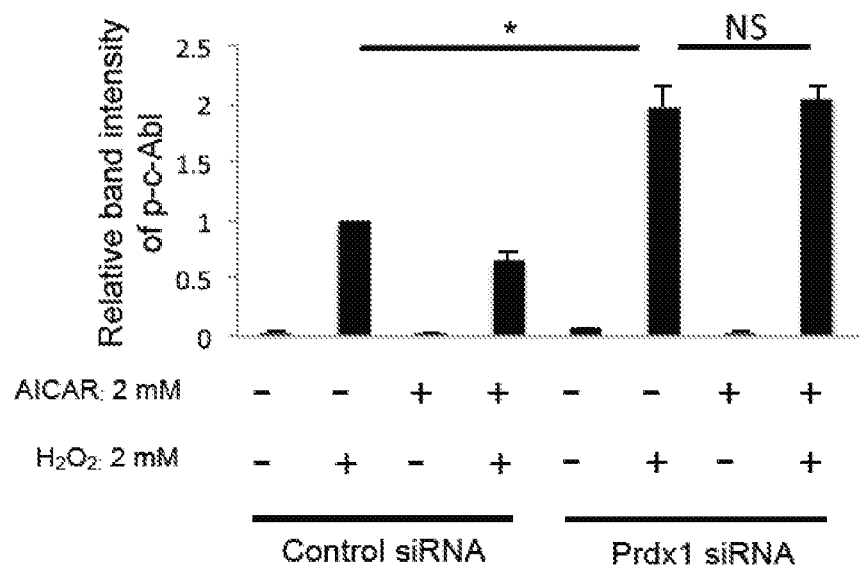

B, Densitometry of p-caveolin-1 in FIG. 6A.

C, Densitometry of p-c-Abl in FIG. 6A.

D, Cells were stimulated with 2 mM of AICAR for 2 h, followed by $H_2O_2$ (2 mM) stimulation for 30 min. After total cell lysates of each group were collected, the interaction between prdx1 and c-Abl was examined by immunoprecipitation with anti-prdx1 antibody. Immunoprecipitates were then subjected to immunoblotting using anti-c-Abl antibody.

Figure 6D:
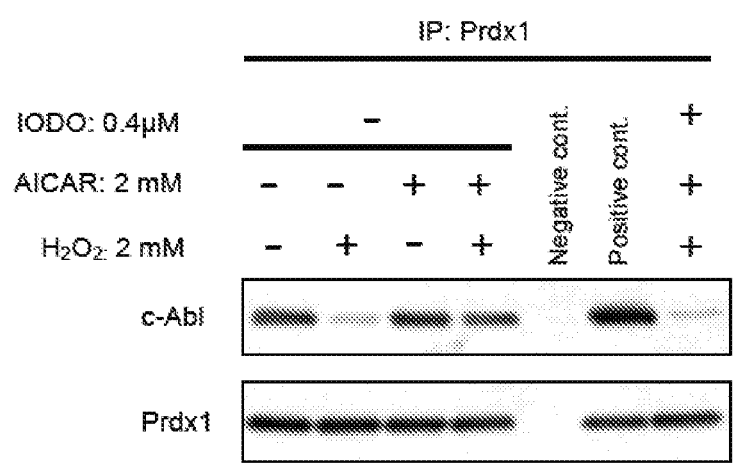
Figure 6E:
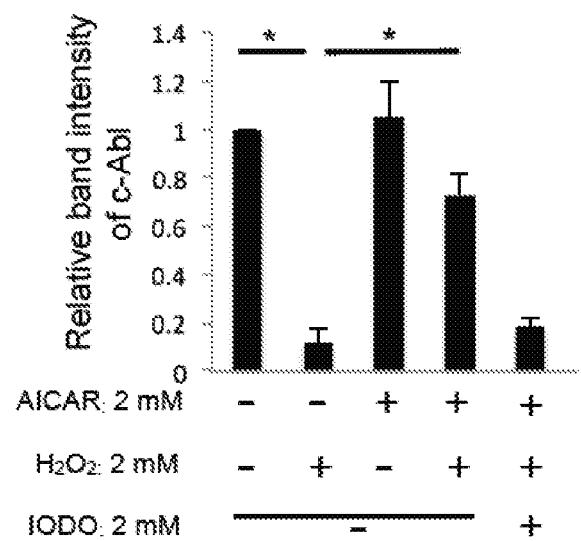

E, Densitometry of p-c-Abl in FIG. 6D.

F, Cells were transfected with siRNA against AMPKα1 or α2. Three days after transfection, cells were stimulated with 2 mM of AICAR for 2 h, followed by $H_2O_2$ (2 mM) stimulation for 30 min. After total cell lysates of each group were collected, the interaction between c-Abl and prdx1 was examined by immunoprecipitation with anti-prdx1 antibody. Immunoprecipitates were then subjected to immunoblotting using anti-c-Abl antibody.

G, Densitometry of c-Abl in FIG. 5F.

H, Co-immunoprecipitation experiments with pull-down using anti-AMPK antibodies showing that AMPK does not directly associate with the c-abl/prdx1 complex.

A,D and F, Representative blots are shown. *, P<0.01; NS, not significant.

Figure 7:
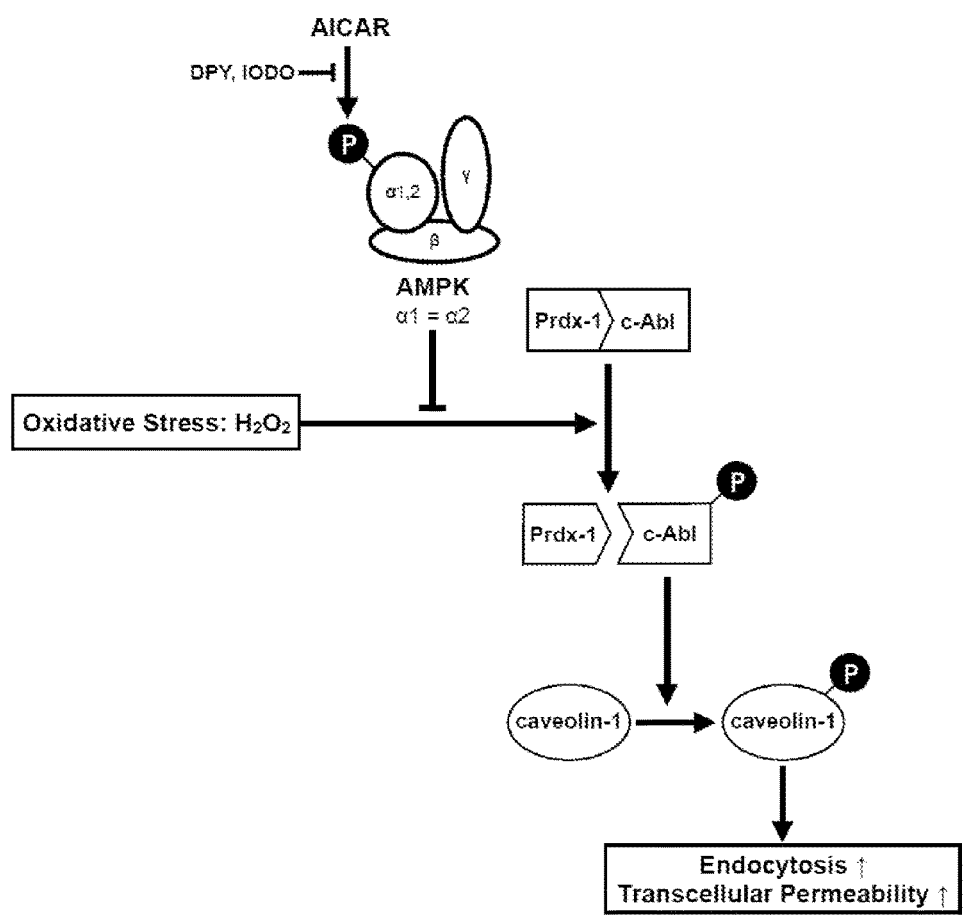

FIG. 7. Proposed model for the mechanism by which AMPK suppresses caveolin-1 phosphorylation and endocytosis under oxidative stress.

AMPK negatively regulates caveolin-1 phosphorylation by suppressing the dissociation between c-Abl and prdx-1.

FIG. 8. AICAR inhibits VEGF-induced vascular tube formation in an in-vitro model through VEGFR2 independent mechanisms.

A: Morphological changes of HUVECs in the presence of VEGF (12.5 ng/mL) and AICAR. The culture conditions of each group in descending order were VEGF (−), AICAR (−), Suramin (−); VEGF (+), AICAR (−), Suramin (−); VEGF (+), AICAR (0.25 mM), Suramin (−); VEGF (+), AICAR (0.5 mM), Suramin (−); VEGF (+), AICAR (1.0 mM), Suramin (−); VEGF (+), AICAR (2.0 mM), Suramin (−); VEGF (+), AICAR (−), Suramin (50 μM). Bar equals 500 μm.

B: Statistical analysis performed to evaluate the tube length. *, p<0.01.

C: HUVECs were cultured in AICAR (2 mM)-containing medium for 2 h, and then after the medium was changed, they were stimulated with VEGF (12.5 ng/mL) for 0 to 60 min. The amounts of (p-)VEGFR2 and (p-)Akt in the HUVECs were then examined by western blotting.

D: Densitometry of p-VEGFR2 in panel C

E: Densitometry of p-Akt in panel C

F: Cells were stimulated with 2 mM of AICAR for 2 h, followed by VEGF (12.5 ng/mL) stimulation for 10 min. After total cell lysates of each group were collected, the interaction between VEGFR2 and caveolin-1 was examined by immunoprecipitation with anti-caveolin-1 antibody. Immunoprecipitates were then subjected to immunoblotting using anti-VEGFR2 antibody.

G: Densitometry of p-VEGFR2 in panel F

C & F: Representative blots are shown. *, p<0.01; NS, not significant.

FIG. 9. AICAR Activation of AMPK leads to PTEN dependent dephosphorylation of Akt.

A: HUVECs were treated with Adenosine Kinase Inhibitor IODO (0.1 μM) for 60 min, and then stimulated with AICAR (2 mM) in the presence or absence of VEGF.

B: Densitometry of p-AMPK in panel A.

C: Densitometry of p-Akt in panel A.

D: Densitometry of p-PTEN in panel A.

E: Cells were transfected with siRNA against PTEN. Three days after transfection, cells were stimulated with 2 mM of AICAR for 2 h, followed by VEGF (12.5 ng/mL) stimulation for 10 min.

F: Densitometry of p-Akt in panel E.

A & E: Representative blots are shown. *, p<0.01; NS, not significant.

FIG. 10. AICAR inhibits VEGF-induced albumin endocytosis and leakage in HUVECs in an in vitro model.

A: After a cell monolayer was formed, each chamber was treated with 2 mM of AICAR for 2 h, followed by VEGF (12.5 ng/mL) stimulation for 10 min. The fluorescent density was measured by spectrofluorometry. *, p<0.01.

B: The expression of (p-)caveolin-1 was also examined by immunofluorescence. (a): control (untreated cells), (b): VEGF (12.5 ng/mL) stimulation for 10 min, (c) pretreated with AICAR (2 mM) for 2 h, (d) pretreated with AICAR for 2 h followed by VEGF (12.5 ng/mL) stimulation for 10 min. Bar=50 μm.

Figure 11A:
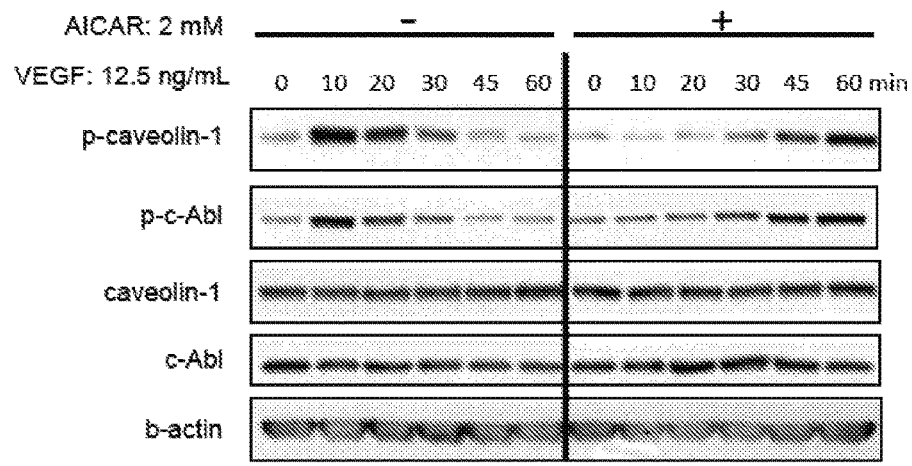
Figure 11B:
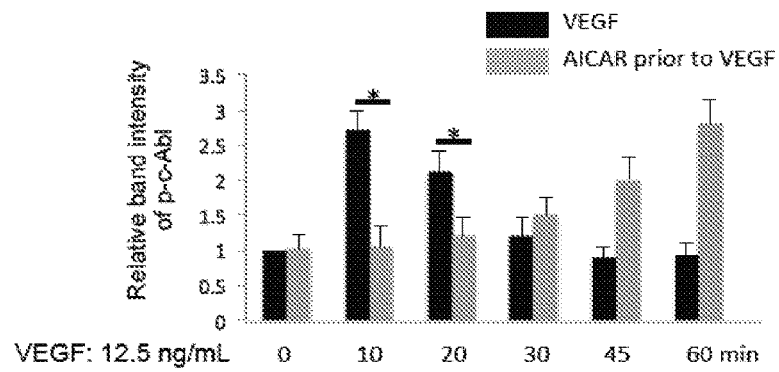
Figure 11C:
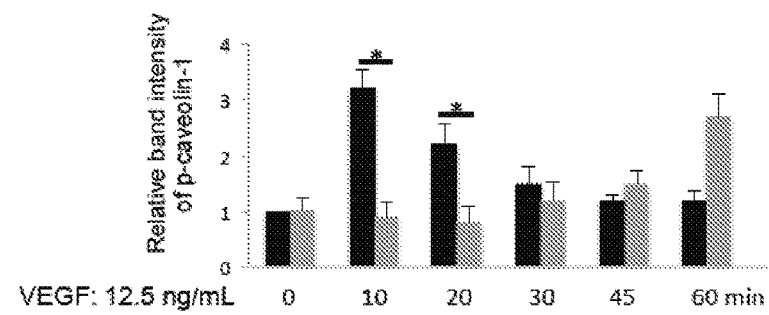

FIG. 11. AICAR inhibits VEGF-induced c-Abl, and caveolin-1 phosphorylation.

A: HUVECs were cultured in AICAR (2 mM)-containing medium for 2 h, and then after the medium was changed, they were stimulated with VEGF (12.5 ng/mL) for 0 to 60 min. The amounts of (p-)caveolin-1 and (p-)c-Abl in the HUVECs were then examined by western blotting.

B: Densitometry of p-c-Abl in panel A.

C: Densitometry of p-caveolin-1 in panel A.

A: Representative blots are shown. *, p<0.01.

FIG. 12. AICAR suppresses VEGF-induced caveolin-1, c-Abl and Akt phosphorylation likely via AMPK.

A: Cells were treated with each concentration of AICAR for 2 h.

B: Cells were treated with each concentration of DPY for 1 h, and then stimulated with 2 mM of AICAR for 2 h.

C: Cells were treated with 8 μM of DPY for 1 h, and then stimulated with 2 mM of AICAR for 2 h, followed by VEGF (12.5 ng/mL) stimulation for 10 min.

D: Cells were treated with each concentration of IODO for 1 h, and then stimulated with 2 mM of AICAR for 2 h.

E: Cells were treated with 0.4 μM of IODO for 1 h, and then stimulated with 2 mM of AICAR for 2 h, followed by VEGF (12.5 ng/mL) stimulation for 10 min.

F: Densitometry of p-Akt in panel D.

G: Densitometry of p-c-Abl in panel D.

H: Densitometry of p-caveolin-1 in panel D.

I: Densitometry of p-Akt in panel E.

J: Densitometry of p-c-Abl in panel E.

K: Densitometry of p-caveolin-1 in panel E.

A-E: Representative blots are shown. *, p<0.01.

Figure 13A:
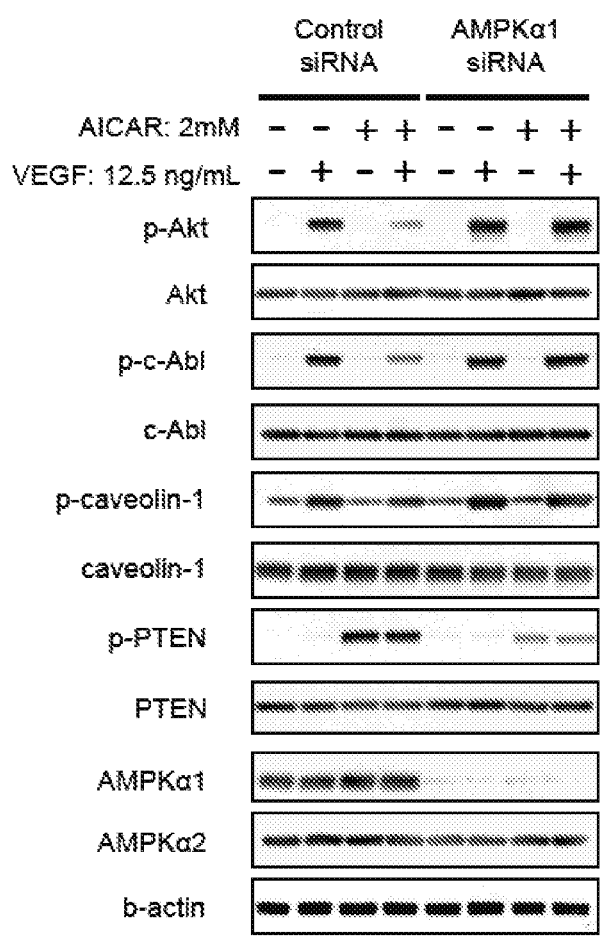
Figure 13F:
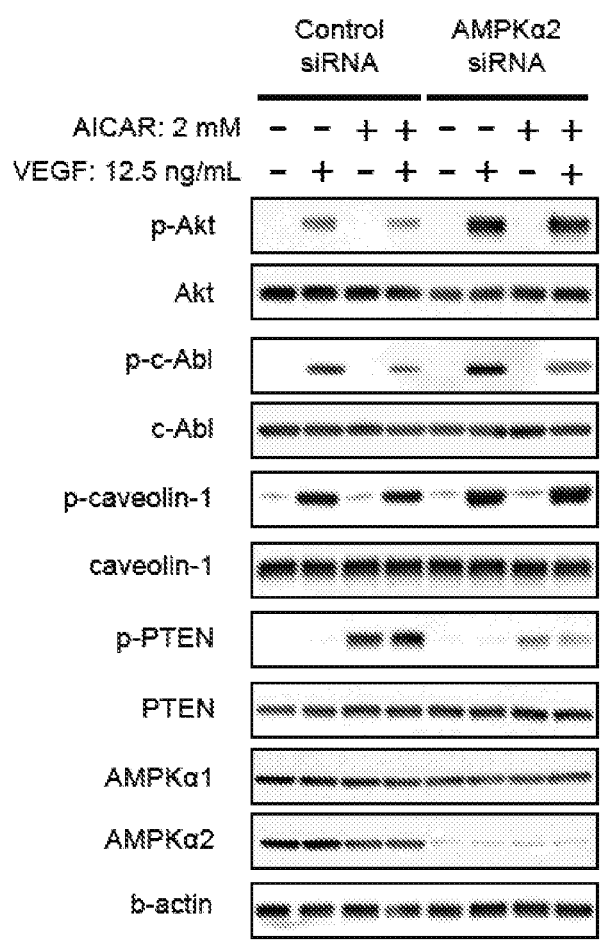

FIG. 13. Both AMPKα1 and α2 isoforms are required for AICAR inhibition of VEGF dependent caveolin-1, c-Abl and Akt phosphorylation.

A,F: The amounts of p-caveolin-1 and p-c-Abl in HUVECs were examined by western blotting. Cells were transfected with siRNA against AMPKα1 (A) or α2 (B). Three days after transfection, cells were stimulated with 2 mM of AICAR for 2 h, followed by VEGF (12.5 ng/mL) stimulation for 10 min.

B: Densitometry of p-Akt in panel A.

C: Densitometry of p-c-Abl in panel A.

D: Densitometry of p-caveolin-1 in panel A.

E: Densitometry of p-PTEN in panel A.

G, Densitometry of p-Akt in panel B.

H, Densitometry of p-c-Abl in panel B.

I, Densitometry of p-caveolin-1 in panel B.

J, Densitometry of p-PTEN in panel B.

A & F: Representative blots are shown. *, P<0.01.

FIG. 14. c-Abl is required for VEGF dependent caveolin-1 phosphorylation.

A: Cells were treated with 10 or 20 μM of imatinib mesylate for 24, 48 or 72 h before stimulation with VEGF (12.5 ng/mL) for 10 min.

B: Densitometry of p-VEGFR2 in panel A.
C: Densitometry of p-caveolin-1 in panel A.
D: Densitometry of p-c-Abl in panel A.
E: Cells were transfected with siRNA against c-Abl. Three days after transfection, cells were stimulated with VEGF (12.5 ng/mL) for 10 min.
F: Densitometry of p-caveolin-1 in panel B.
G: Densitometry of p-VEGFR2 in panel B.
A & E: Representative blots are shown. *, p<0.01; NS, not significant.

FIG. 15. AICAR mediated AMPK activation inhibits VEGF dependent caveolin-1 phosphorylation by suppressing the dissociation between prdx1 and c-Abl.

A: Cells were transfected with siRNA against prdx1. Three days after transfection, cells were stimulated with 2 mM of AICAR for 2 h, followed by VEGF (12.5 ng/mL) stimulation for 10 min. The amounts of p-c-Abl and p-caveolin-1 were examined by western blotting.

B: Densitometry of p-c-Abl in panel A.
C: Densitometry of p-caveolin-1 in panel A.
D: Cells were stimulated with 2 mM of AICAR for 2 h, followed by VEGF (12.5 ng/mL) stimulation for 10 min. After the total cell lysates of each group were collected, the interaction between prdx1 and c-Abl was examined by immunoprecipitation with anti-prdx1 antibody. Immunoprecipitates were then subjected to immunoblotting using anti-c-Abl antibody.
E: Densitometry of c-Abl in panel D.
F: Cells were transfected with siRNA against AMPKα1 or α2. Three days after transfection, cells were stimulated with 2 mM of AICAR for 2 h, followed by VEGF (12.5 ng/mL) stimulation for 10 min. After total cell lysates of each group were collected, the interaction between c-Abl and prdx1 was examined by immunoprecipitation with anti-prdx1 antibody. Immunoprecipitates were then subjected to immunoblotting using anti-c-Abl antibody.
G: Densitometry of c-Abl in panel F.
A,D,F: Representative blots are shown. *, P<0.01; NS, not significant.

Figure 16:
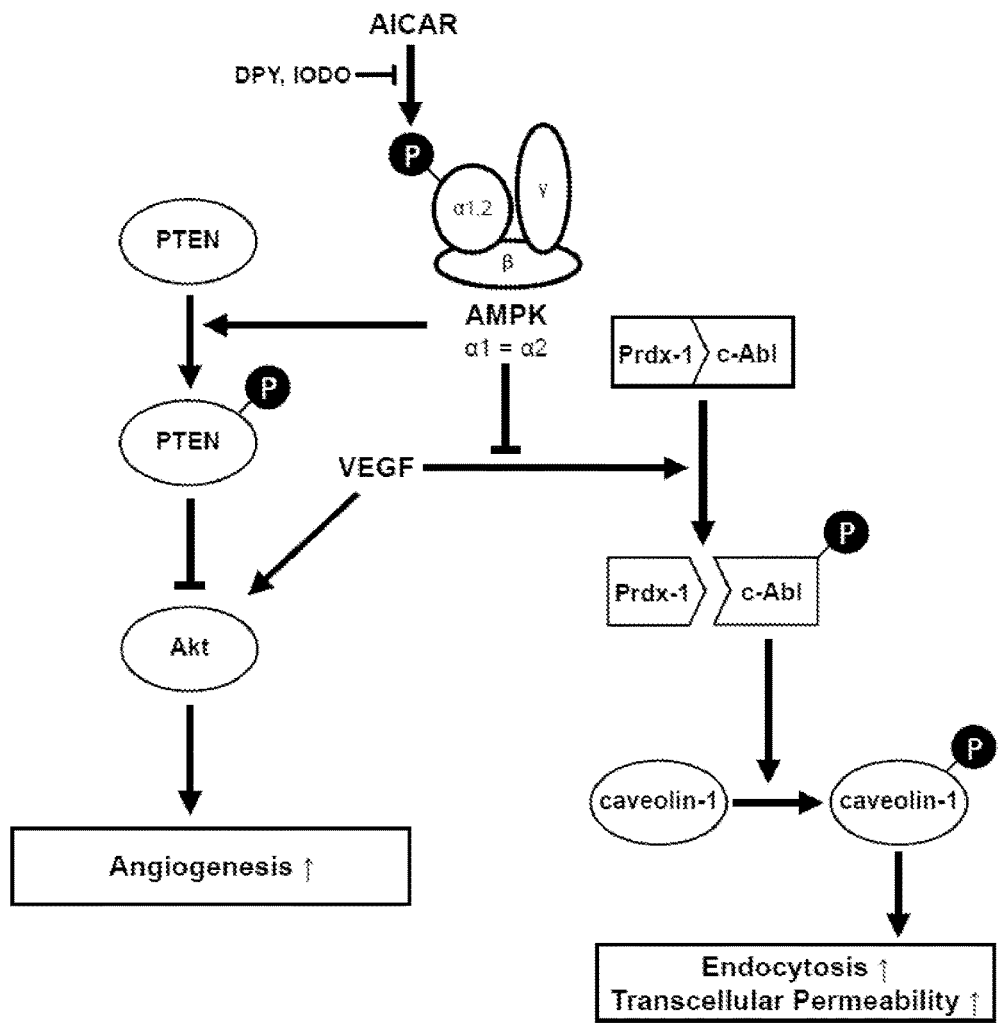

FIG. 16. Proposed model for the mechanism by which AMPK activator AICAR suppresses VEGF induced angiogenesis and caveolin-1 dependent trancytosis.

AMPK negatively regulates Akt and caveolin-1 phosphorylation by activating PTEN and suppressing the dissociation between c-Abl and prdx1.

DETAILED DESCRIPTION

Using multiple biochemical and molecular biology techniques, the present inventors have identified AMPK as a novel negative regulator of VEGF-induced caveolin-1 and Akt phosphorylation in HUVECs contributing to the suppression of VEGF induced tube formation and vascular endothelial cell permeability. These effects are mediated in part by PTEN dephosphorylation of Akt and AMPK dependent stabilization of c-Abl/Prdx1 complex. Thus, the present disclosure includes methods for reducing or delaying ocular neovascularization by administering one or both of an AMPK activators or a PTEN activator.

AMPK

AMP-activated protein kinase (AMPK) is a serine/threonine kinase that regulates energy homeostasis and metabolic stress (Hardie and Hawley, (2001) Bioessays 23, 1112-1119). AMPK acts as a sensor of cellular energy status and maintains the balance between ATP production and consumption. In mammals, AMPK exists as a heterotrimer with α, β, and γ subunits, each of which is encoded by two or three genes (α1, α2, β1, β2, γ1, γ2, and γ3). The α subunit possesses catalytic activity, whereas the β and γ subunits are regulatory and maintain the stability of the heterotrimer complex. The importance of AMPKα is illustrated by the finding that dual deficiency of AMPKα1 and AMPKα2 results in an embryonic-lethal phenotype (Viollet et al. (2009) Front Biosci 14, 19-44).

Prior studies suggest that AMPK has a much wider range of functions, including the regulation of cell growth, cell proliferation, cell polarity, and autophagy (Wang et al. (2009) Acta Physiol (Oxf) 196, 55-63; Theodoropoulou et al. (2010) FASEB J 24, 2620-2630) and activation of PTEN (Phosphatase and tensin homolog deleted on chromosome 10) (Kim and Choi, (2012) Biochem Biophys Res Commun 425, 866-872), which negatively regulates the activity of this VEGF/PI3K/Akt (Myers et al. (1997) Proc Natl Acad Sci USA 94, 9052-9057; Tamura, et al. (1998) Science 280, 1614-1617). In addition, we have demonstrated that activation of AMPK inhibits retinoblastoma cell proliferation, tumor growth and angiogenesis, ocular inflammation, and MMP-9 expression (Theodoropoulou et al., 2010; Theodoropoulou et al., (2013) PLoS One 8, e52852; Suzuki et al., (2011) Invest Ophthalmol Vis Sci 52, 6565-6571; Suzuki et al., (2012) Invest Ophthalmol Vis Sci 53, 4158-4169; Morizane et al., (2011) J Biol Chem 286, 16030-16038). Because these functions of AMPK are closely linked to the vascular hyper-permeability and angiogenesis induced by stress, we hypothesized that AICAR activation of AMPK has an inhibitory effect on VEGF induced vascular permeability and angiogenesis. Indeed, a recent study reported that AMPK protects a paracellular pathway by supporting the adherent junction proteins of N-cadherin and VE-cadherin (Creighton et al., (2011) FASEB J 25, 3356-3365), and there have been conflicting studies on the role of AMPK in angiogenesis (Ahluwalia and Tarnawski, (2011) J Physiol Pharmacol 62, 583-587; Stahmann et al., (2010) J Biol Chem 285, 10638-10652; Peyton et al., (2012) J Pharmacol Exp Ther 342, 827-834). Thus, the present study examined the role of AMPK in the transcellular pathway and phosphorylation of caveolin-1 as well as angiogenesis under VEGF stimulation.

The present study identified AICAR as a novel chemical inhibitor of VEGF induced Akt, c-Abl and caveolin-1 phosphorylation. Provided herein is evidence that the AMPK activator AICAR suppresses tube formation (angiogenesis) in an in vitro assay by inhibiting Akt phosphorylation, likely due to activation of PTEN. In addition AMPK activation by AICAR suppresses VEGF induced endocytosis and leakage by inhibiting caveolin-1 phosphorylation and stabilizing Prdx1/c-Abl complex. These results reveal the suppressive role of AMPK in VEGF-induced caveolin-1, c-Abl and Akt phosphorylation. The possibility of caveolin-1 phosphorylation as a therapeutic target for VEGF-mediated vascular diseases was not described prior to the present study. In addition, the inhibitory effect of AICAR on angiogenesis has not been prior studied, though the present inventors observed a decrease in tumor vessel formation in AICAR-treated retinoblastoma xenografts (Theodoropoulou et al. (2013) PLoS One 8, e52852).

In other studies AICAR and activation of AMPK has been related with cytoprotection and stimulation of angiogenesis in situations of ischemia/re-perfusion injury or hypoxia (Russell et al., (2004) J Clin Invest 114, 495-503; Nagata, et al., (2003) J Biol Chem 278, 31000-31006; Ouchi et al., (2005) Circ Res 96, 838-846). Yet Zou et al. ((2003) J Biol Chem 278, 34003-34010) and Nagata et al. (2003) did not observe a positive role of AMPK in VEGF-mediate angiogenesis under normoxic conditions. In other studies (Reihill et al., (2011) Vasc Cell 3, 9), despite the apparent requirement for AMPK in VEGF-stimulated endothelial cell proliferation, activation of AMPK with AICAR, A769662 or Ad.AMPK-CA suppressed endothelial proliferation in the absence of VEGF and may relate to the cell cycle inhibition effects of AMPK. The in vitro study described herein and an in vivo study with retinoblastoma related angiogenesis (Theodoropoulou et al. (2013) PLoS ONE 8(1): e52852) shows that the AMPK activator AICAR is related with anti-angiogenesis properties and may be related to its anti-proliferative effects. Recently, Zhou et al. ((2011) Oncogene 30, 1892-1900) reported that AMPK upregulates TNFSF15, a cytokine that exerts a potent inhibitory effect on vascular endothelial cells and tumor angiogenesis. It is also possible that the various effects of AICAR depend on the specific cell type, cellular events following external stimuli, paracrine effects and/or downstream-regulated pathways.

PTEN

Phosphatase and tensin homologue deleted on chromosome 10 (PTEN), which has been identified as a tumor suppressor (see Li et al., J Cell. Biochem. 102:1368, 2007), is a phospholipid phosphatase that converts PI(3,4,5)P3 to PI(4,5)P2 (PIP3 to PIP2). This action opposes the phosphatidylinositol 3-kinases (PI3Ks), a large family of proteins activated by numerous cellular processes (including growth factor signaling) and activate the Akt protein via PIP3. Akt then directly or indirectly activates a number of other proteins including mammalian target of rapamycin (mTOR) which leads to protein synthesis, enhancing cell proliferation and cell survival (Jiang et al., Biochim. Biophys. Acta 1784:150, 2008). PTEN thus controls and down-regulates this survival pathway by reducing levels of PIP3. PTEN also possesses phosphatase-independent tumor suppressive functions. See, e.g., WO2009126842A1 and US20070280918.

AMPK and PTEN

Figure 8A:
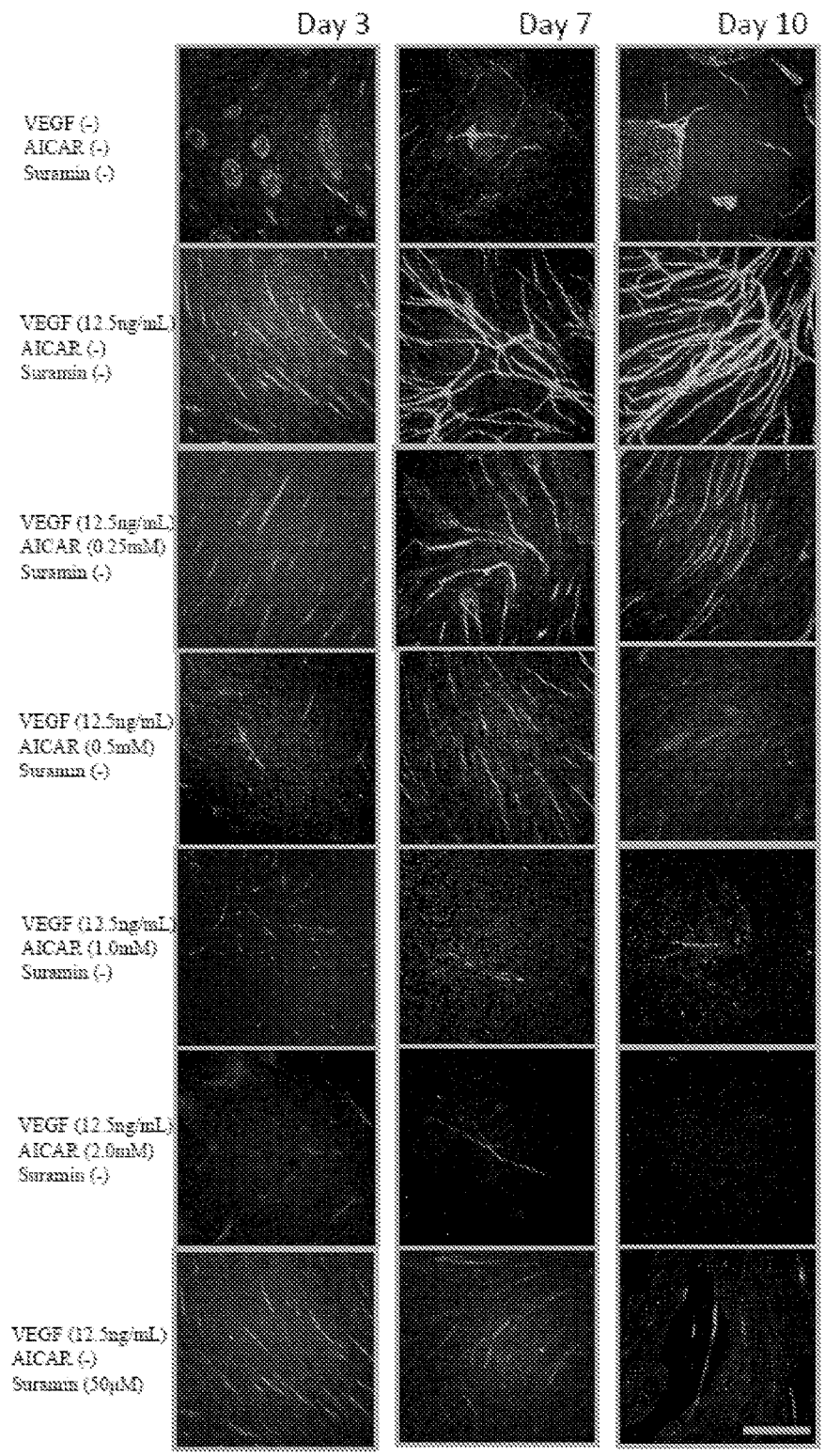
Figure 8B:
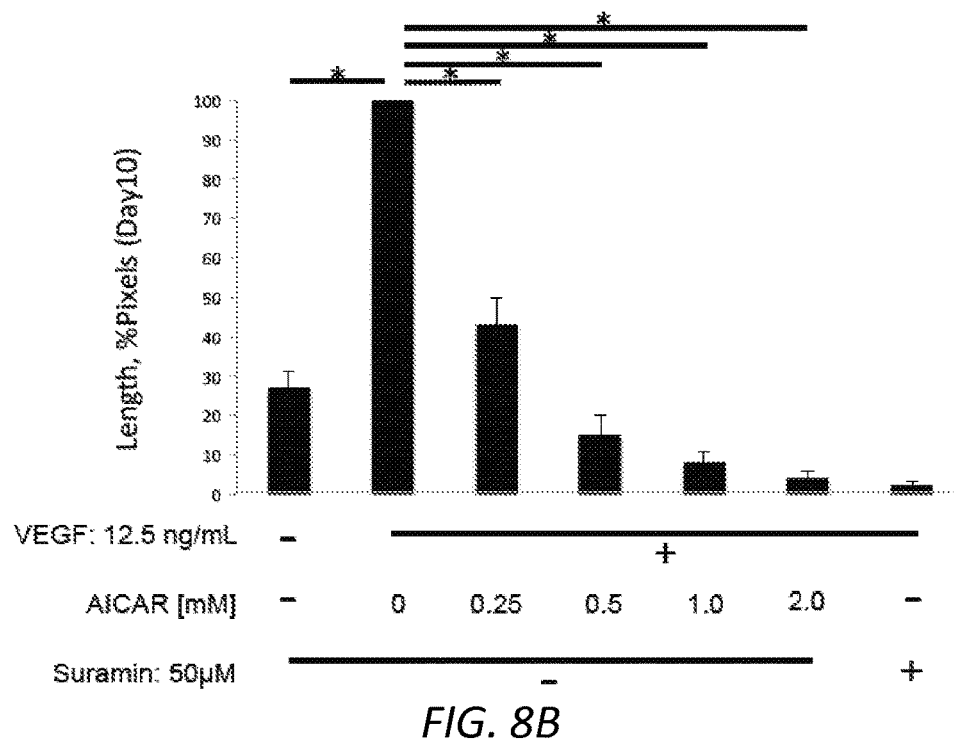
Figure 8C:
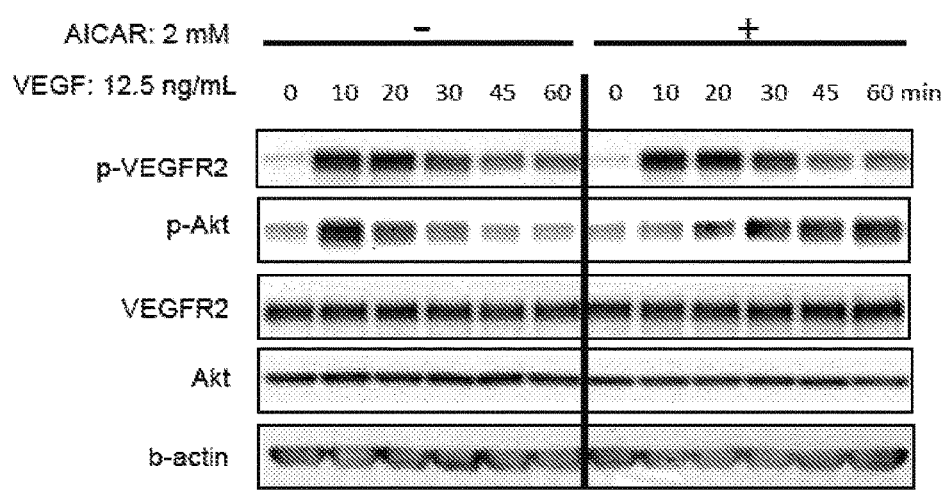
Figure 8D:
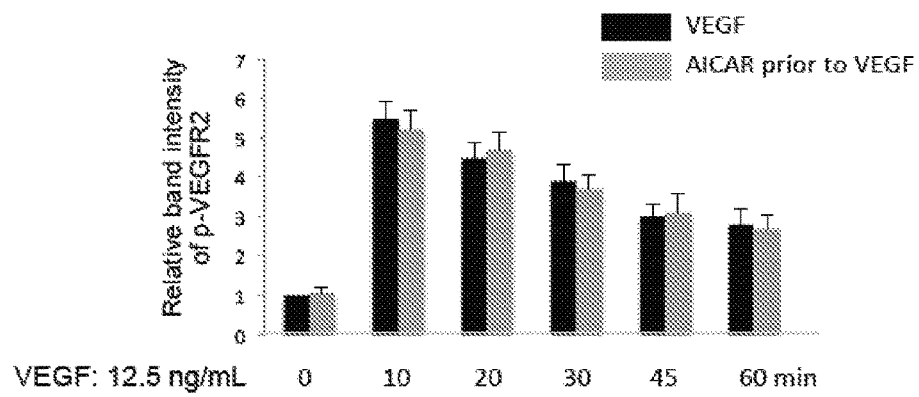
Figure 8E:
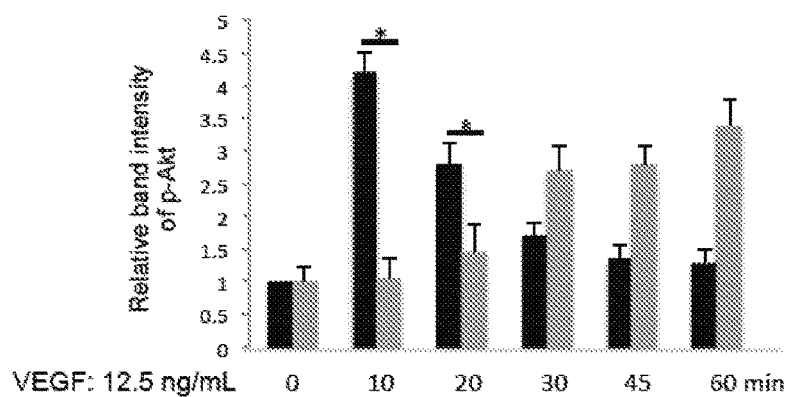
Figure 8F:
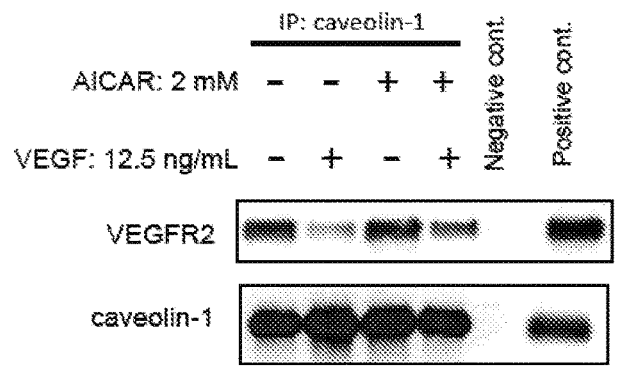
Figure 8G:
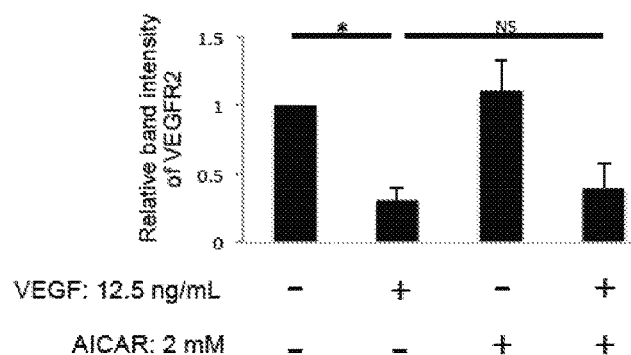

The effects of AICAR in inhibiting tube formation in the present studies appear to be downstream of VEGFR2, since AICAR pretreatment has no influence on VEGFR2 phosphorylation (FIG. 8C,D) or on VEGFR2 dissociation from caveolin-1 (FIG. 8F,G). It is well known that VEGF regulates the activity of Akt pathway and that PTEN is a negative regulator of that pathway (Myers et al. (1997) and Tamura et al. (1998)). In addition, Kim et al. (2012) reported that AMPK can induce PTEN phosphorylation in vascular smooth muscle cells. In the present study, AICAR administration lead to concomitant activation of PTEN in an AMPK dependent fashion and a subsequent Akt de-phosphorylation (FIGS. 9A-D and 6) and thus it was hypothesized that AICAR activation of AMPK suppresses VEGF mediated tube formation via PTEN de-phosphorylation of Akt. This finding of AICAR and AMPK effects on Akt differ somewhat from the findings of Levine et al. ((2007) J Biol Chem 282, 20351-20364) which show that siRNA downregulation of AMPK α1 suppresses overall phospho-Akt. In that study although VEGF stimulation of Akt phosphorylation was blunted it was not completely abolished and showed at least a 2.5 fold activation.

VEGF

VEGF is a key regulator of angiogenesis, and it controls the proliferation, migration, differentiation, and survival of endothelial cells through binding to VEGF receptor-2 (VEGFR2) (Shibuya et al., (2006) Exp Cell Res 312, 549-560). VEGFR2 is a receptor tyrosine kinase that autophosphorylates and initiates a variety of signaling pathways, including the phospholipase Cγ/protein kinase C/$Ca^{2+}$ pathway and the phosphoinositide 3-kinase/Akt pathway (Holmes et al., (2007) Cell Signal 19, 2003-2012; Olsson et al., (2006) Nat Rev Mol Cell Biol 7, 359-371). Overexpression of VEGF can induce pathological endothelial cell permeability and angiogenesis via Akt phosphorylation at Ser473 in the diseases such as cancer, diabetic retinopathy and age-related macular degeneration (Olson et al., (2006) Nat Rev Mol Cell Biol 7, 359-371; Komarova and Malik, (2010) Annu Rev Physiol 72, 463-493; Bates, (2010) Cardiovasc Res 87, 262-271; Bates and Harper, (2002) Vascul Pharmacol 39, 225-237), and it leads to the disorder of vessel fenestrations, tight junctions and adherent junctions (in the paracellular pathway) and in the transcellular pathway ((Olson et al., (2006)). Passage of small proteins such as albumin has been attributed to the VEGF-induced formation of caveolae, the assembly of caveolae into vesiculovacuolar organelles (VVOs), and/or the induction of transendothelial pores. Feng et al. ((1999) Invest Ophthalmol Vis Sci 40, 157-167) reported that a VEGF-induced increase in the permeability of the cell membrane was mediated by caveolae, and Zhao et al. ((2011) J Mol Neurosci 44, 122-129) reported that VEGF increased the permeability through a caveolae-mediated transcellular pathway in a blood-tumor barrier. It is also known that VEGFR2 colocalizes with VEGFR2 in the caveolae (Holmes et al., (2007) Cell Signal 19, 2003-2012; Labrecque et al., (2003) Mol Biol Cell 14, 334-347; Tahir et al., (2009) Cancer Biol Ther 8, 2286-2296).

Methods of Treatment

The methods described herein include methods for the treatment of disorders associated with ocular neovascularization. In some embodiments, the disorder is choroidal, retinal, or surface neovascularization; vasoproliferative ocular tumours; or inflammation and vascular leakage conditions.

In some embodiments, the disorder will stem from overformation of blood vessels, or formation of blood vessels in an unwanted area, e.g., in the avascular regions of the eye, e.g., retinopathies, or in a tumor, e.g., a cancerous or benign tumor. For example, the ophthalmological disorder can be age-related macular degeneration (AMD), where new blood vessels grow under the retina, or retinopathy, e.g., diabetic retinopathy, where abnormal vessels grow on top of the retina. Other ophthalmological disorders include retinopathy (e.g., is selected from a group comprising of: retinopathy of prematurity (ROP); diabetic retinopathy; retina vein occlusion; sickle cell retinopathy; Stargardt's disease; choroidal neovascularization, radiation retinopathy), microangiopathy, neovascular glaucoma, corneal graft rejection, glaucoma, herpetic and infectious keratitis, ocular ischemia, neovascular glaucoma, corneal, uveal and iris neovascularization, orbital and eyelid tumors, Stevens Johnson Syndrome, ocular cicatricial pemphigoid, wounds or other injuries (e.g., chemical injuries due to exposure to irritants, acids or bases), and ocular surface diseases. The disorder can be characterized by, for example, corneal, retinal, choroidal, uveal, or iris neovascularization.

In some embodiments, the disorder is associated with choroidal neovascularization (CNV), e.g., choroidal neovascularization secondary to, for example, the neovascular (wet) form of age-related macular degeneration (AMD), pathologic myopia, or ocular histoplasmosis syndrome. In some embodiments, the disorder is associated with retinal neovascularization (e.g., proliferative diabetic retinopathy). In some embodiments, the disorder is associated with surface neovascularization (e.g., secondary to a chemical or other injury, or Stevens-Johnson syndrome).

In some embodiments, the disorder is associated with tumor neovascularization, e.g., vasoproliferative ocular tumours (e.g., neoplastic and benign retinal vascular tumors such as retinal capillary hemangioma, hemangioblastomas, cavernous hemangiomas, Racemose Hemangioma (Wyburn-Mason Syndrome), Retinal Vasoproliferative Tumors, and tumors associated with Von Hippel-Lindau (VHL) disease; or choroidal vascular tumors including circumscribed choroidal hemangiomas and diffuse choroidal hemangiomas). See, e.g., Turell and Singh, Middle East Afr J Ophthalmol. 2010 July-September; 17(3): 191-200.

In addition, the methods described herein include methods for the treatment of disorders associated with inflammation or "leaky" vasculature. Ocular inflammatory conditions that may be treated with the methods described herein include, but are not limited to, endophthalmitis (e.g., the endogenous form and the exogenous form), macular edema (e.g., macular edema that occurs as a result of age-related macular degeneration, cataract surgery, diabetes, drug toxicity, eye injury, retinal vein occlusion (e.g., central retinal vein occlusion (CRVO) and branch retinal vein occlusion), or other inflammatory eye diseases, e.g., pseudophakic macular edema), conjunctivitis, episcleritis, keratitis, optic neuritis, orbital pseudotumor, retinal vasculitis, scleritis, and uveitis (e.g., (i) uveitis associated with sepsis (e.g., LPS-induced uveitis); (ii) autoimmune uveitis (e.g., uveitis associated with lupus); or (iii) uveitis associated with type II, type III, type IV, or type V hypersensitivity reactions). See, e.g., WO2011133964 and WO2013003467.

Generally, the methods include administering a therapeutically effective amount of one or more of an AMPK activator, a PTEN activator, or both, to a subject who is in need of, or who has been determined to be in need of, such treatment.

Examples of routes of administration include systemic parenteral, e.g., intravenous, intraperitoneal, intradermal, or subcutaneous; local to the eye, e.g., topical, intravitreal, intraocular, intraorbital, periorbital, subconjuctival, subretinal, subtenons or transscleral; and systemic oral administration. In some embodiments, intraocular administration or administration by eye drops, ointments, creams, gels, or lotions may be used, inter alia. In some embodiments, the AMPK or PTEN activator is administered systemically, e.g., orally; in preferred embodiments, the AMPK or PTEN activator is administered to the eye, e.g., via topical (eye drops, lotions, or ointments) administration, or by local injection, e.g., periocular or intravitreal injection; see, e.g., Gaudana et al., AAPS J. 12(3):348-360 (2010); Fischer et al., Eur J Ophthalmol. 21 Suppl 6:S20-6 (2011). Administration may be provided as a periodic bolus (for example, intravitreally or intravenously) or as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag, or a contact lens slow release formulation system). The AMPK or PTEN activator may be administered locally, for example, by continuous release from a sustained release drug delivery device immobilized to an inner wall of the eye or via targeted transscleral controlled release into the choroid (see, for example, PCT/US00/00207, PCT/US02/14279, PCT/US2004/004625, Ambati et al. (2000) Invest. Ophthalmol. Vis. Sci. 41:1181-1185, and Ambati et al (2000) Invest. Ophthalmol. Vis. Sci. 41:1186-1191). A variety of devices suitable for administering agents locally to the inside of the eye are known in the art. See, for example, U.S. Pat. Nos. 6,251,090, 6,299,895, 6,416,777, 6,413,540, and 6,375,972, and PCT/US00/28187.

In some embodiments, the treatment is administered to a subject who has been diagnosed with a disorder associated with ocular neovascularization; such a diagnosis can be made by a skilled practitioner using known methods and ordinary skill. In some embodiments, the methods include a step of diagnosing or identifying or selecting a subject with a disorder associated with ocular neovascularization, or identifying or selecting a subject based on the presence or a diagnosis of a disorder associated with ocular neovascularization.

As used in this context, to "treat" means to ameliorate at least one symptom of the disorder associated with ocular neovascularization. Often, pathological ocular neovascularization results in a loss of visual acuity; thus, a treatment can result in a reduction in ocular vascularity and a return or approach to normal sight. Administration of a therapeutically effective amount of a compound described herein for the treatment of a condition associated with ocular neovascularization will result in decreased levels or rate of ocular neovascularization (which can prevent or delay the progression or onset of loss of visual acuity), or a regression in ocular vascularity.

The methods described herein include the manufacture and use of pharmaceutical compositions, which include compounds identified by a method described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include systemic (e.g., parenteral and oral) and local (ocular, e.g., intravitreal or topical) administration. Thus also within the scope of the present disclosure are compositions comprising the AMPK or PTEN activators described herein in a formulation for administration for the eye, e.g., in eye drops, lotions, creams, e.g., comprising microcapsules, microemulsions, or nanoparticles. Methods of formulating suitable pharmaceutical compositions for ocular delivery are known in the art, see, e.g., Losa et al., Pharmaceutical Research 10:1 (80-87 (1993); Gasco et al., J. Pharma Biomed Anal., 7(4):433-439 (1989); Fischer et al., Eur J Ophthalmol. 21 Suppl 6:S20-6 (2011); and Tangri and Khurana, Intl J Res Pharma Biomed Sci., 2(4):1541-1442 (2011).

General methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can be included in a container, pack, or dispenser (e.g., eye drop bottle) together with instructions for administration. In some embodiments, the compositions are provided lyophilized or dry, and the kit includes saline for making a solution comprising the AMPK or PTEN activator(s).

Age-Related Macular Degeneration

Advanced AMD is characterized as "atrophic" or "neovascular," the former showing loss of outer retinal layers, and the latter the presence of choroidal neovascularization (CNV).[8] Neovascular (or "wet") AMD is defined by the formation of abnormal blood vessels that grow from the choroidal vasculature, through breaks in Bruch's membrane, toward the outer retina[1]. These blood vessels are immature in nature and leak fluid below or within the retina.[9] The two forms of AMD can occur together and share pathologies of cell death and fibroglial replacement.[10,11] Neovascular AMD accounts for 10 to 15% of AMD cases, develops abruptly, and rapidly leads to substantial loss of vision.[9,12] Although growth factors appear to play an important role in the late stage of neovascular AMD progression, they likely do not contribute to the underlying cause of the disease. Current standard of care for patients with CNV involves targeting the proangiogenic and permeability molecule vascular endothelial growth factor-A (VEGF).[13-15] However, although anti-VEGF therapy blocks vascular permeability and angiogenesis, it does not lead to complete vascular regression.[14] Moreover, in patients treated with VEGF antagonists, substantial vision improvement occurs in only one-third, with one-sixth of treated patients still progressing to legal blindness.[13,15] Thus, there is an urgent need for safe nutritional or pharmacological interventions for the treatment and ideally the prevention of AMD.

PTEN Activators

The methods described herein can include the administration of a therapeutically effective amount of one or more PTEN activators. PTEN agonists or activators are agents that directly stimulate the expression of PTEN in a cell, or directly stimulates the activity of PTEN; such agonists include di-C8-phosphatidylinositol 4,5-P2 (PI(4,5)P2 and PI(5)P (but PI(4)P, PI(3,4)P2, and PI(3,5)P2 do not activate PTEN). Alternatively or in addition, any of the methods described herein can include the administration of PPAR-gamma agonists such as rosiglitazone (Patel et al., (2001) Current. Biol. 11:764-8), or a compound that down regulates the PI3K/Akt/mTOR pathway, e.g., an inhibitor of mTOR, which is considered herein to be a PTEN agonist. Preferred PTEN agonists/mTOR inhibitors for use in the methods described herein include rapamycin (Rapamune®, sirolimus, ATC code L04AA10 commercially available from Wyeth) and its chemical analogues such as CCI-779 (temsirolimus, Anatomical Therapeutic Chemical (ATC) code L01XE09, commercially available from Wyeth), RAD-001 (everolimus, ATC code L04AA18. commercially available from Novartis) and AP-2357 (Granville et al, op. cit.). Other agonists include zinc finger proteins or nucleic acids encoding the same that bind to and activate transcription of PTEN (see, e.g., WO 00/00388). Other PTEN agonists are described in US20070280918. Whereas proteins are typically administered parenterally, e.g. intravenously, small molecules may be administered parenterally or orally.

AMPK Activators

The methods described herein can include the administration of a therapeutically effective amount of one or more AMPK activators. A number of small molecule inhibitors of AMPK are known in the art, including C24 (Li et al., Toxicol Appl Pharmacol. 2013 Dec. 1; 273(2):325-34); A-769662 (4-hydroxy-3-[4-(2-hydroxyphenyl)phenyl]-6-oxo-7H-thieno[2,3-b]pyridine-5-carbonitrile; Cool et al., Cell Metab. 2006 June; 3(6):403-16); D942 (5-[3-[4-[2-(4-fluorophenyl) ethoxy]phenyl]propyl] furan-2-carboxylic acid); ZLN024 (see FIG. 1A of Zhang et al., PLoS ONE 8(8): e72092 (2013)). Other known AMPK activators include drugs such as 5-Aminoimidazole-4-carboxamide riboside (AICA riboside or AICAR); AICA ribotide (ZMP); guanidine; galegine; metformin (dimethylbiguanide); phemformin (phenethylbiguanide); antifolate drugs that inhibit AICAR transformylase (e.g., methotrexate, pemetrexed); thiazolidinediones (e.g., rosiglitazone, pioglitazone, or troglitazone); 2-Deoxyglucose (2DG); phenobarbital; PT1; and salicylate. See, e.g., Hardie et al. (2012) Chem. Biol. 19:1222-1236; Hawley et al. (2012) Science 336:918-922. In addition, AMPK activators are described in the following: U.S. Pat. No. 8,604,202B2 (Merck); U.S. Pat. No. 8,592,594B2 (Roche); U.S. Pat. No. 8,586,747B2 (Roche); U.S. Pat. No. 8,563,746B2 (Merck); U.S. Pat. No. 8,546,427B2 (Roche); U.S. Pat. No. 8,563,729B2 (Merck); U.S. Pat. No. 8,394,969B2 (Merck); U.S. Pat. No. 8,329,914B2 (Merck); U.S. Pat. No. 8,329,738B2 (Merck); US20120172333A1 (GSK); US20110060001A1 (Merck); US20090105293A1 (Merck); EP2519527B1 (Poxel); and WO2010073011A2 (Betagenon).

Combination Therapies

In some embodiments, the methods described herein are administered in combination with another therapy. Thus, the methods can optionally include administration (e.g., in the same composition, or separately but during the same time frame as the administration of an AMPK activator, a PTEN activator, or both) of one or more additional therapies or active agents. For example, the present methods can be used in combination with other established treatments such as anti VEGF therapies, non-steroidal or steroidal anti-inflammatory treatments, or neuroprotective treatments. For example, to treat inflammatory disease, corticosteroids, antimetabolites, cycloplegics, and biologics can be used in combination with an AMPK activator, a PTEN activator, or both, to control the inflammatory process.

In some embodiments a neuroprotective treatment is administered in combination with an AMPK activator, a PTEN activator, or both; a neuroprotective treatment can include, for example, administration of a hydrophilic bile acid (e.g., a ursodeoxycholic acid (UDCA) or a tauroursodeoxycholic acid (TUDCA).), e.g., as described in WO 2013025840 A1; administration of a necrosis inhibitor, e.g., RIP-3 kinase inhibitor, e.g., a necrostatin, e.g., necrostatin-1, alone or combined with an apoptotic inhibitor (e.g., a pan-caspase inhibitor, e.g., Z-VAD and/or IDN-6556), as described in WO2012061045 and WO2011133964.

In some embodiments, one or more anti-VEGF therapies are administered in combination with an AMPK activator, a PTEN activator, or both; anti-VEGF therapies are known in the art and include Ayastin (Beyacizumab) monoclonal antibody that inhibits VEGF-A; Lucentis (Ranibizumab) monoclonal Fab antibody fragment that inhibits VEGF-A; Eylea (Aflibercept) fusion protein that binds VEGF-A, VEGF-B and PGF; Zaltrap (Aflibercept used for cancer treatment); and Macugen (Pegaptanib) aptamer that binds VEGF. See, e.g., US20130209570 (Carasquillo, Miller, MEEI).

EXAMPLES

The invention is further described in the following examples, which do not limit the scope of the invention described in the claims.

Example 1

AMPK Inhibits Oxidative Stress Induced Caveolin-1 Phosphorylation and Endocytosis by Suppressing the Dissociation Between c-Abl and prdx1 in Endothelial Cells.

This Example demonstrates that activation of AMPK inhibits oxidative stress induced cayeolin-1 phosphorylation and endocytosis and this effect is mediated in part by stabilizing the interaction between c-Abl and prdx-1.

Materials and Methods

The following materials and methods were used in Example 1.

Materials—Antibodies for (p-) caveolin-1, (p-) c-Abl, Peroxiredoxin I (Prdx1), (p-) AMPK, AMPKα1, AMPKα2, and VE-cadherin were purchased from Cell Signaling Technologies (Beverly, Mass.). Antibodies for β-actin and p-caveolin-1 (for immunofluorescence) were obtained from Abcam (Cambridge, Mass.) and R&D Systems (Minneapolis, Minn.), respectively. Secondary antibodies of Alexa Flour 488 goat anti mouse IgG and Alexa Flour 647 goat anti rabbit IgG were purchased from Invitrogen (Carlsbad, Calif.). 5-amino-4-imidazole carboxamide riboside (AICAR), a pharmacological activator of AMPK, was purchased from Toronto Research Chemicals (Toronto, ON, Canada). Hydrogen Peroxide ($H_2O_2$), 5-Iodotubericidin (IODO) and dipyridamole (DPY) were purchased from Sigma (St Louis, Mo.). Imatinib mesylate, c-Abl inhibitor, was purchased from Cayman Chemicals (Ann Arbor, Mich.). SiRNAs targeting c-Abl, AMPKα1, AMPKα2 and Prdx1, and control siRNA were purchased from Thermoscientific (Rockford, Ill.).

Cell Culture—HUVECs (Lonza, Walkersville, Md.) were cultured in Endothelial Growth Medium (EGM, Lonza, Walkersville, Md.). For all experiments, cells were grown at 37° C. in a humidified atmosphere of 5% CO2 and 95% air. Experiments were performed on cells below passage 3 to 6 grown to 80-90% confluence.

Protein Extraction and Western Blotting—Protein extraction and western blotting were carried out as described previously (Morizane et al. JBC). Densitometric analysis of bands was performed using ImageJ software. Lane-loading differences were normalized by β-actin.

Immunoprecipitation—Immunoprecipitation was performed with the Universal Magnetic Co-IP Kit (Active Motif North America, Carlsbad, Calif.), according to the manufacturer's instruction.

siRNA—Cells were transfected with siRNAs using Nucleofection kit (Amaxa Biosystems, Gaithersburg, Md.), following the manufacturer's protocol. The medium was changed at 6 h after transfection. The down-regulation of each protein was evaluated at 3 days after nucleofection.

Albumin Endocytosis Assay—After serum starvation for overnight, HUVECs were pretreated with AICAR (2 mM) for 2 h, and then stimulated with $H_2O_2$ (2 mM) for 30 min. We added BSA conjugated with Alexa 555 (50 μg/ml, Life Technologies, Gaithersburg, Md.) in the medium during the experiment. Cells on coverslips were washed three times with cold TBS and fixed in 100% methanol at −20° C. for 15 min. Cells were then permeabilized in 0.3% Triton X-100, 0.15% BSA in TBS with 0.05% Tween 20 (TBST) for 15 min at room temperature and blocked with 0.5% skim milk in TBST for 60 min at room temperature. Cells were incubated in p-caveolin-1 antibody diluted 1:200 and VE-cadherin antibody diluted 1:400 for overnight at 4° C., and then incubated for 2 h in secondary antibody diluted 1:300. Cells were then rinsed three times in TBST before mounting in Toto3 (Life Technologies, Gaithersburg, Md.). Images were acquired with confocal microscope, Leica TCS SP2 spectral confocal laser scanning microscope (Leica Microsystems, Wetzlar, Germany).

Statistical Analysis—All experiments were repeated a minimum of three times. All data were expressed as means±S.D. Statistical differences were analyzed by the unpaired Student's t test. Differences were considered significant at P<0.05.

1.1 AICAR Suppresses Oxidative Stress Induced Phosphorylation of Caveolin-1 and c-Abl.

Figure 1D:
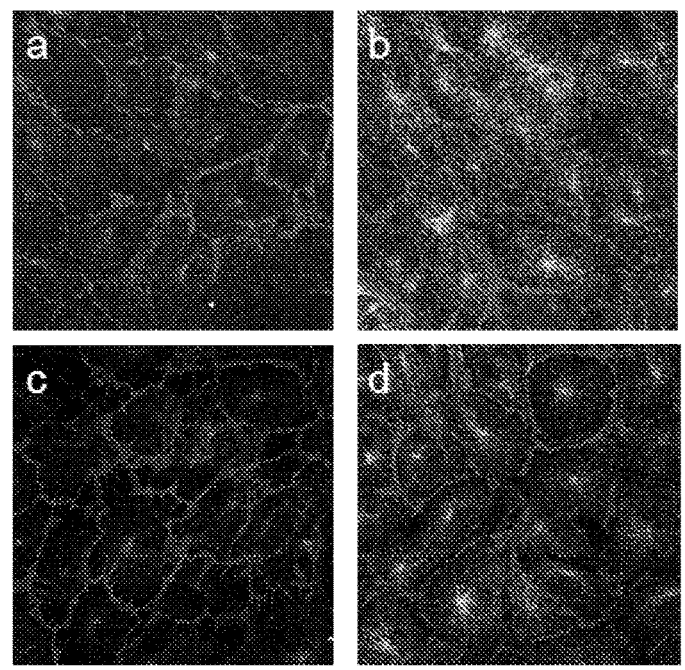

It has been already reported that caveolin-1 is phosphorylated on tyrosine 14 under hyperosmotic shock and oxidative stress (17,18) and that c-Abl, which is an upstream kinase of caveolin-1, is required for oxidative stress-induced phosphorylation of caveolin-1 (19). To study the effect of oxidative stress on the phosphorylation of caveolin-1 and c-Abl in HUVEC, we exposed HUVEC to $H_2O_2$ and determined the phosphorylation by western blotting. Incubation with $H_2O_2$ resulted in the phosphorylation of both caveolin-1 and c-Abl dose-dependently (FIG. 1A). To investigate whether AMPK activation inhibits oxidative stress induced phosphorylation of caveolin-1 and c-abl, we pretreated HUVEC with a pharmacological activator of AMPK, AICAR, prior to $H_2O_2$ exposure. As shown in FIGS. 1A, B and C), AICAR significantly suppressed the phosphorylation of both cayeolin-1 and c-Abl. Caveolin-1 is the main component of the caveolae plasma membranes and involved in receptor-independent endocytosis (2,20). To determine the effect of $H_2O_2$ and AICAR on the endocytosis, we evaluated the amount of fluorescein-conjugated albumin endocytosed by HUVEC. Exposure to $H_2O_2$ resulted in the elevation of albumin endocytosis together with caveolin-1 phosphorylation (FIG. 1D). By contrast, pretreatment by AICAR suppressed both endocytosis and caveolin-1 phosphorylation (FIG. 1D).

1.2 AICAR Inhibits $H_2O_2$ Induced Phosphorylation of Caveolin-1 via Activation of AMPK.

It has been reported that AICAR has several effects independent of AMPK pathway (21-24). To determine the effect of AICAR on AMPK phosphorylation in HUVEC, we investigated phosphorylation of AMPK after AICAR administration by western blotting. As shown in FIG. 2A, AICAR phosphorylated AMPK dose-dependently. We next used 2 different inhibitors of AICAR, DPY and IODO, to exclude the possibility that the inhibitory effect of AICAR on caveolin-1 phosphorylation was caused by mechanisms other than AMPK activation. DPY blocks adenosine transporters and prevents uptake of AICAR into the cells (11,25). IODO inhibits adenosine kinase in the cell and prevents conversion of AICAR to ZMP, which activates AMPK (11,25). Pretreatment with DPY or IODO inhibited AICAR induced AMPK phosphorylation dose-dependently (FIG. 2, B and F). Furthermore, pretreatment with DPY or IODO prior to $H_2O_2$ exposure significantly restored the inhibitory effect of AICAR on phosphorylation of both caveolin-1 and c-Abl (FIG. 2). These results indicate that ZMP accumulation through both transport and phosphorylation of AICAR is required for the suppression of caveolin-1 phosphorylation, suggesting that AMPK activation is a key process for the inhibitory effect of AICAR.

1.3 Both AMPKα1 and α2 Isoforms are Required for the Inhibition of Caveolin-1 Phosphorylation Under Oxidative Stress.

The catalytic subunit of AMPK, AMPKα, has two isoforms (i.e. AMPKα1 and α2), which show differential tissue-specific expression (8,9,15). To determine the role of both isoforms in the inhibitory effect of AMPK on caveolin-1 phosphorylation under oxidative stress, we used RNA interference technology to knock down AMPKα1 or α2 in HUVEC. Knockdown of either isoform of AMPKα abolished the inhibitory effect of AICAR on $H_2O_2$ induced phosphorylation of caveolin-1 and c-Abl (FIG. 3). Knockdown of both AMPK isoforms with two different siRNA oligos showed similar results (FIG. 4). These results suggest that both AMPKα1 and α2 isoforms are required to inhibit caveolin-1 phosphorylation under oxidative stress.

1.4 Inhibitory Effect of AMPK on Caveolin-1 Phosphorylation Under Oxidative Stress is Dependent on c-Abl.

Figure 5D:
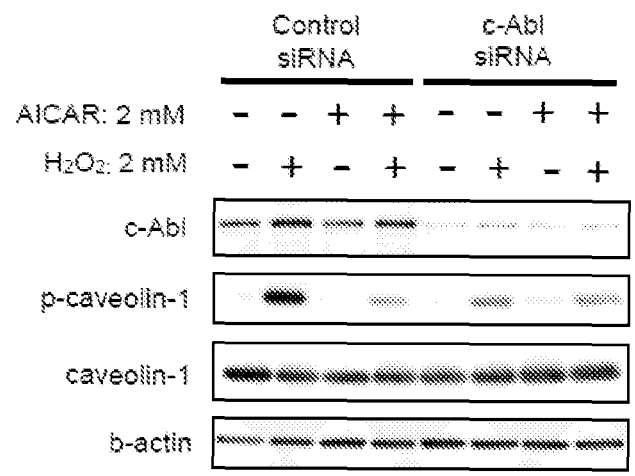
Figure 5E:
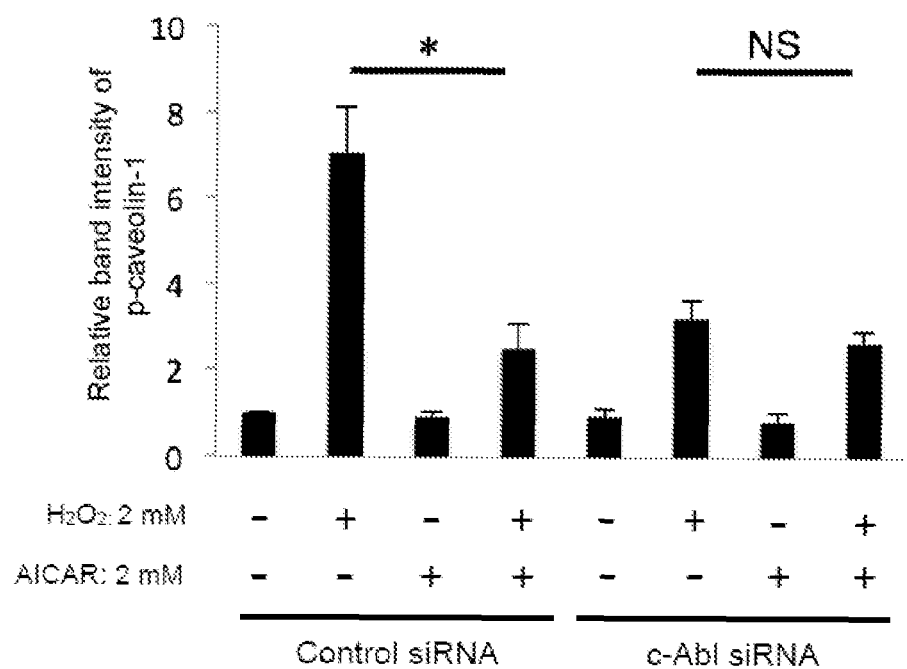

Next, to determine the role of c-Abl in the oxidative stress induced phosphorylation of caveolin-1, we utilized a c-Abl inhibitor, imatinib mesylate (26,27). As shown in FIGS. 5A, B and C, imatinib mesylate inhibited $H_2O_2$ induced phosphorylation of both caveolin-1 and c-Abl dose- and time-dependently, indicating that c-Abl is an upstream kinase of caveolin-1 in HUVEC. We next investigated the role of c-Abl in the inhibitory effect of AICAR on canveolin-1 phosphorylation by knock down c-Abl with siRNA. Deletion of c-Abl resulted in the significant decrease in caveolin-1 phosphorylation after $H_2O_2$ exposure (FIGS. 5D and E). Furthermore, pretreatment with AICAR prior to $H_2O_2$ exposure did not change caveolin-1 phosphorylation significantly, suggesting that inhibitory effect of AICAR on caveolin-1 phosphorylation under oxidative stress is dependent on c-Abl (FIGS. 5D and E).

1.5 Prdx1 is Indispensable for the Inhibitory Effect of AMPK on the $H_2O_2$ Induced Phosphorylation of Caveolin-1.

Prdx1, one of the antioxidant enzymes, plays a protective role in cells against oxidative stress. In cytoplasm, prdx1 exists as a protein complex with c-Abl-SH domain (28-31), and protects c-Abl from phosphorylation (32). Under oxidative stress, oxidant dissociates the protein-protein interaction and phosphorylates liberated c-Abl. To investigate the role of prdx1 in the inhibitory effect of AICAR on canveolin-1 phosphorylation, we knocked down prdx1 in HUVEC with siRNA and determined the level of caveolin-1 phosphorylation by western blotting. As shown in FIGS. 6A, B and C, knockdown of prdx1 resulted in increased phosphorylation of both caveolin-1 and c-Abl after $H_2O_2$ exposure. Furthermore, lack of prdx1 abolished the inhibitory effect of AICAR on the $H_2O_2$ induced phosphorylation of both caveolin-1 and c-Abl. These results indicate that prdx1 is indispensable for the inhibitory effect of AMPK on the $H_2O_2$ induced phosphorylation of caveolin-1.

1.6 AMPK Inhibits Caveolin-1 Phosphorylation Under Oxidative Stress by Suppressing the Dissociation Between prdx1 and c-Abl.

Figure 6F:
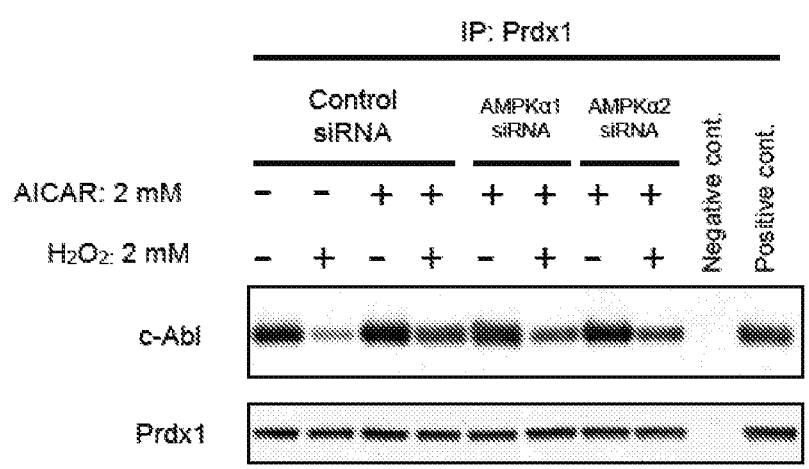
Figure 6G:
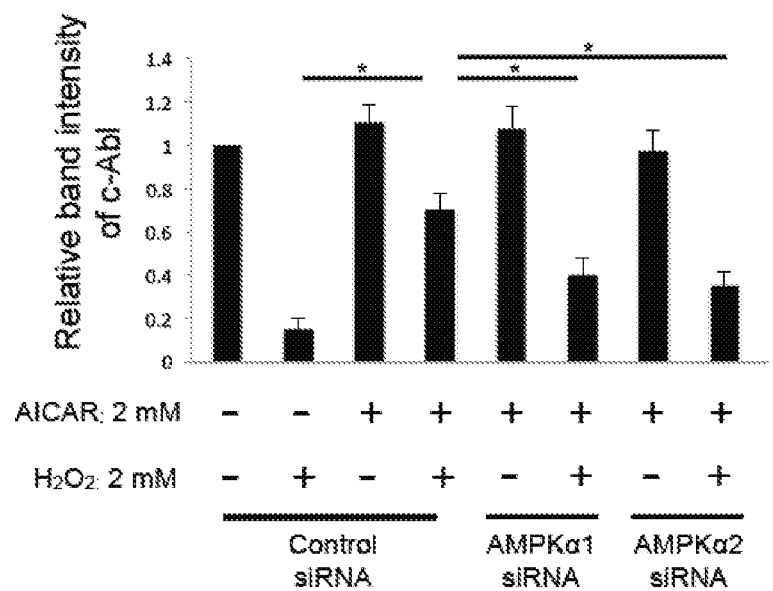
Figure 6H:
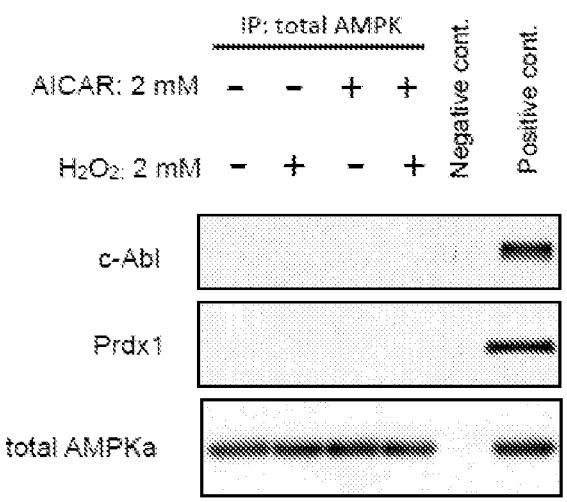

To investigate the relationship between AMPK and protein interaction of c-Abl and prdx1, we performed co-immunoprecipitation experiments. As shown in FIG. 6D, oxidative stress resulted in the dissociation between prdx1 and c-Abl. The dissociation was inhibited by treatment with AICAR prior to $H_2O_2$. In contrast, treatment with IODO prior to $H_2O_2$ and AICAR restored the dissociation, indicating AICAR inhibits the $H_2O_2$ induced dissociation between c-Abl and prdx1. To confirm this, we further conducted co-immunoprecipitation for the cell lysates from HUVEC lacking AMPKα1 or α2. Deletion of either AMPKα1 or α2 isoform decreased the inhibitory effect of AICAR on the dissociation between c-Abl and prdx1 (FIG. 6F, G). These results indicated that activation of AMPK inhibits caveolin-1 phosphorylation under oxidative stress by suppressing the dissociation between prdx1 and c-Abl.

1.7 AMPK is not Detected in the prdx1/c-abl Complex.

To further investigate the mechanism, we asked if AMPK directly associates with the c-abl/prdx1 complex. Co-immunoprecipitation experiments (FIG. 6H), failed to show any direct association. This could be because the association is very weak or because the effects of AMPK on the prdx1/c-abl complex are indirect.

REFERENCES FOR EXAMPLE 1

1. Mehta, D., and Malik, A. B. (2006) Signaling mechanisms regulating endothelial permeability. *Physiol Rev* 86, 279-367
2. Sun, Y., Minshall, R. D., and Hu, G. (2011) Role of caveolin-1 in the regulation of pulmonary endothelial permeability. *Methods Mol Biol* 763, 303-317
3. Minshall, R. D., Sessa, W. C., Stan, R. V., Anderson, R. G., and Malik, A. B. (2003) Caveolin regulation of endothelial function. *Am J Physiol Lung Cell Mol Physiol* 285, L1179-1183
4. Komarova, Y., and Malik, A. B. (2010) Regulation of endothelial permeability via paracellular and transcellular transport pathways. *Annu Rev Physiol* 72, 463-493
5. Razani, B., Engelman, J. A., Wang, X. B., Schubert, W., Zhang, X. L., Marks, C. B., Macaluso, F., Russell, R. G., Li, M., Pestell, R. G., Di Vizio, D., Hou, H., Jr., Kneitz, B., Lagaud, G., Christ, G. J., Edelmann, W., and Lisanti, M. P. (2001) Caveolin-1 null mice are viable but show evidence of hyperproliferative and vascular abnormalities. *J Biol Chem* 276, 38121-38138
6. Drab, M., Verkade, P., Elger, M., Kasper, M., Lohn, M., Lauterbach, B., Menne, J., Lindschau, C., Mende, F., Luft, F. C., Schedl, A., Haller, H., and Kurzchalia, T. V. (2001) Loss of caveolae, vascular dysfunction, and pulmonary defects in caveolin-1 gene-disrupted mice. *Science* 293, 2449-2452
7. Hu, G., and Minshall, R. D. (2009) Regulation of transendothelial permeability by Src kinase. *Microvasc Res* 77, 21-25
8. Hardie, D. G., and Hawley, S. A. (2001) AMP-activated protein kinase: the energy charge hypothesis revisited. *Bioessays* 23, 1112-1119
9. Viollet, B., Athea, Y., Mounier, R., Guigas, B., Zarrinpashneh, E., Horman, S., Lantier, L., Hebrard, S., Devin-Leclerc, J., Beauloye, C., Foretz, M., Andreelli, F., Ventura-Clapier, R., and Bertrand, L. (2009) AMPK: Lessons from transgenic and knockout animals. *Front Biosci* 14, 19-44
10. Wang, W., and Guan, K. L. (2009) AMP-activated protein kinase and cancer. *Acta Physiol (Oxf)* 196, 55-63
11. Theodoropoulou, S., Kolovou, P. E., Morizane, Y., Kayama, M., Nicolaou, F., Miller, J. W., Gragoudas, E., Ksander, B. R., and Vavvas, D. G. (2010) Retinoblastoma cells are inhibited by aminoimidazole carboxamide ribonucleotide (AICAR) partially through activation of AMP-dependent kinase. *FASEB J* 24, 2620-2630
12. Theodoropoulou, S., Brodowska, K., Kayama, M., Morizane, Y., Miller, J. W., Gragoudas, E. S., and Vavvas, D. G. (2013) Aminoimidazole Carboxamide Ribonucleotide (AICAR) Inhibits the Growth of Retinoblastoma In Vivo by Decreasing Angiogenesis and Inducing Apoptosis. *PLoS One* 8, e52852
13. Suzuki, J., Manola, A., Murakami, Y., Morizane, Y., Takeuchi, K., Kayama, M., Miller, J. W., Sobrin, L., and Vavvas, D. G. (2011) Inhibitory effect of aminoimidazole carboxamide ribonucleotide (AICAR) on endotoxin-induced uveitis in rats. *Invest Ophthalmol Vis Sci* 52, 6565-6571
14. Suzuki, J., Yoshimura, T., Simeonova, M., Takeuchi, K., Murakami, Y., Morizane, Y., Miller, J. W., Sobrin, L., and Vavvas, D. G. (2012) Aminoimidazole carboxamide ribonucleotide ameliorates experimental autoimmune uveitis. *Invest Ophthalmol Vis Sci* 53, 4158-4169
15. Morizane, Y., Thanos, A., Takeuchi, K., Murakami, Y., Kayama, M., Trichonas, G., Miller, J., Foretz, M., Viollet, B., and Vavvas, D. G. (2011) AMP-activated protein kinase suppresses matrix metalloproteinase-9 expression in mouse embryonic fibroblasts. *J Biol Chem* 286, 16030-16038
16. Creighton, J., Jian, M., Sayner, S., Alexeyev, M., and Insel, P. A. (2011) Adenosine monophosphate-activated kinase alpha1 promotes endothelial barrier repair. *FASEB J* 25, 3356-3365
17. Volonte, D., Galbiati, F., Pestell, R. G., and Lisanti, M. P. (2001) Cellular stress induces the tyrosine phosphorylation of caveolin-1 (Tyr(14)) via activation of p38 mitogen-activated protein kinase and c-Src kinase. Evidence for caveolae, the actin cytoskeleton, and focal adhesions as mechanical sensors of osmotic stress. *J Biol Chem* 276, 8094-8103
18. Aoki, T., Nomura, R., and Fujimoto, T. (1999) Tyrosine phosphorylation of caveolin-1 in the endothelium. *Exp Cell Res* 253, 629-636
19. Sanguinetti, A. R., and Mastick, C. C. (2003) c-Abl is required for oxidative stress-induced phosphorylation of caveolin-1 on tyrosine 14. *Cell Signal* 15, 289-298
20. Sun, Y., Hu, G., Zhang, X., and Minshall, R. D. (2009) Phosphorylation of caveolin-1 regulates oxidant-induced pulmonary vascular permeability via paracellular and transcellular pathways. *Circ Res* 105, 676-685, 615 p following 685
21. Guigas, B., Bertrand, L., Taleux, N., Foretz, M., Wiernsperger, N., Vertommen, D., Andreelli, F., Viollet, B., and Hue, L. (2006) 5-Aminoimidazole-4-carboxamide-1-beta-D-ribofuranoside and metformin inhibit hepatic glucose phosphorylation by an AMP-activated protein kinase-independent effect on glucokinase translocation. *Diabetes* 55, 865-874
22. Guigas, B., Taleux, N., Foretz, M., Detaille, D., Andreelli, F., Viollet, B., and Hue, L. (2007) AMP-activated protein kinase-independent inhibition of hepatic mitochondrial oxidative phosphorylation by AICA riboside. *Biochem J* 404, 499-507
23. Mukhtar, M. H., Payne, V. A., Arden, C., Harbottle, A., Khan, S., Lange, A. J., and Agius, L. (2008) Inhibition of glucokinase translocation by AMP-activated protein kinase is associated with phosphorylation of both GKRP and 6-phosphofructo-2-kinase/fructose-2,6-bisphosphatase. *Am J Physiol Regul Integr Comp Physiol* 294, R766-774

24. Foretz, M., Hebrard, S., Leclerc, J., Zarrinpashneh, E., Soty, M., Mithieux, G., Sakamoto, K., Andreelli, F., and Viollet, B. (2010) Metformin inhibits hepatic gluconeogenesis in mice independently of the LKB1/AMPK pathway via a decrease in hepatic energy state. *J Clin Invest* 120, 2355-2369

25. Sanz, P. (2008) AMP-activated protein kinase: structure and regulation. *Curr Protein Pept Sci* 9, 478-492

26. Muller, B. A. (2009) Imatinib and its successors—how modern chemistry has changed drug development. *Curr Pharm Des* 15, 120-133

27. Druker, B. J. (2008) Translation of the Philadelphia chromosome into therapy for CML. *Blood* 112, 4808-4817

28. Wen, S. T., and Van Etten, R. A. (1997) The PAG gene product, a stress-induced protein with antioxidant properties, is an Abl SH3-binding protein and a physiological inhibitor of c-Abl tyrosine kinase activity. *Genes Dev* 11, 2456-2467

29. Prosperi, M. T., Ferbus, D., Rouillard, D., and Goubin, G. (1998) The pag gene product, a physiological inhibitor of c-abl tyrosine kinase, is overexpressed in cells entering S phase and by contact with agents inducing oxidative stress. *FEBS Lett* 423, 39-44

30. Cao, J., Schulte, J., Knight, A., Leslie, N. R., Zagozdzon, A., Bronson, R., Manevich, Y., Beeson, C., and Neumann, C. A. (2009) Prdx1 inhibits tumorigenesis via regulating PTEN/AKT activity. *EMBO J* 28, 1505-1517

31. Morell, M., Espargaro, A., Aviles, F. X., and Ventura, S. (2007) Detection of transient protein-protein interactions by bimolecular fluorescence complementation: the Abl-SH3 case. *Proteomics* 7, 1023-1036

32. Wong, C. M., Zhou, Y., Ng, R. W., Kung Hf, H. F., and Jin, D. Y. (2002) Cooperation of yeast peroxiredoxins Tsa1p and Tsa2p in the cellular defense against oxidative and nitrosative stress. *J Biol Chem* 277, 5385-5394

33. Levine, Y. C., Li, G. K., and Michel, T. (2007) Agonist-modulated regulation of AMP-activated protein kinase (AMPK) in endothelial cells. Evidence for an AMPK→Rac1→Akt→endothelial nitric-oxide synthase pathway. *J Biol Chem* 282, 20351-20364

34. Wang, F., Song, X., Zhou, M., Wei, L., Dai, Q., Li, Z., Lu, N., and Guo, Q. (2012) Wogonin inhibits H(2)O(2)-induced vascular permeability through suppressing the phosphorylation of caveolin-1. *Toxicology*

35. Rothberg, K. G., Heuser, J. E., Donzell, W. C., Ying, Y. S., Glenney, J. R., and Anderson, R. G. (1992) Caveolin, a protein component of caveolae membrane coats. *Cell* 68, 673-682

36. Glenney, J. R., Jr., and Soppet, D. (1992) Sequence and expression of caveolin, a protein component of caveolae plasma membrane domains phosphorylated on tyrosine in Rous sarcoma virus-transformed fibroblasts. *Proc Natl Acad Sci USA* 89, 10517-10521

37. Ko, Y. G., Liu, P., Pathak, R. K., Craig, L. C., and Anderson, R. G. (1998) Early effects of pp60(v-src) kinase activation on caveolae. *J Cell Biochem* 71, 524-535

38. Sun, S. W., Zu, X. Y., Tuo, Q. H., Chen, L. X., Lei, X. Y., Li, K., Tang, C. K., and Liao, D. F. (2010) Caveolae and caveolin-1 mediate endocytosis and transcytosis of oxidized low density lipoprotein in endothelial cells. *Acta Pharmacol Sin* 31, 1336-1342

39. Kumar, S., Mishra, N., Raina, D., Saxena, S., and Kufe, D. (2003) Abrogation of the cell death response to oxidative stress by the c-Abl tyrosine kinase inhibitor STI571. *Mol Pharmacol* 63, 276-282

40. Cao, H., Courchesne, W. E., and Mastick, C. C. (2002) A phosphotyrosine-dependent protein interaction screen reveals a role for phosphorylation of caveolin-1 on tyrosine 14: recruitment of C-terminal Src kinase. *J Biol Chem* 277, 8771-8774

41. Ceolotto, G., Gallo, A., Papparella, I., Franco, L., Murphy, E., Tori, E., Pagnin, E., Fadini, G. P., Albiero, M., Semplicini, A., and Avogaro, A. (2007) Rosiglitazone reduces glucose-induced oxidative stress mediated by NAD(P)H oxidase via AMPK-dependent mechanism. *Arterioscler Thromb Vasc Biol* 27, 2627-2633

42. Deng, G., Long, Y., Yu, Y. R., and Li, M. R. (2010) Adiponectin directly improves endothelial dysfunction in obese rats through the AMPK-eNOS Pathway. *Int J Obes (Lond)* 34, 165-171

43. Lassila, M., Allen, T. J., Cao, Z., Thallas, V., Jandeleit-Dahm, K. A., Candido, R., and Cooper, M. E. (2004) Imatinib attenuates diabetes-associated atherosclerosis. *Arterioscler Thromb Vasc Biol* 24, 935-942

44. Hagerkvist, R., Makeeva, N., Elliman, S., and Welsh, N. (2006) Imatinib mesylate (Gleevec) protects against streptozotocin-induced diabetes and islet cell death in vitro. *Cell Biol Int* 30, 1013-1017

45. Hagerkvist, R., Sandler, S., Mokhtari, D., and Welsh, N. (2007) Amelioration of diabetes by imatinib mesylate (Gleevec): role of beta-cell NF-kappaB activation and anti-apoptotic preconditioning. *FASEB J* 21, 618-628

46. Louvet, C., Szot, G. L., Lang, J., Lee, M. R., Martinier, N., Bollag, G., Zhu, S., Weiss, A., and Bluestone, J. A. (2008) Tyrosine kinase inhibitors reverse type 1 diabetes in nonobese diabetic mice. *Proc Natl Acad Sci USA* 105, 18895-18900

47. Jeyabalan, J., Shah, M., Viollet, B., and Chenu, C. (2012) AMP-activated protein kinase pathway and bone metabolism. *J Endocrinol* 212, 277-290

48. Gayard, M., Guilluy, C., Rousselle, A., Viollet, B., Henrion, D., Pacaud, P., Loirand, G., and Rolli-Derkinderen, M. (2011) AMPK alpha 1-induced RhoA phosphorylation mediates vasoprotective effect of estradiol. *Arterioscler Thromb Vasc Biol* 31, 2634-2642

49. Goirand, F., Solar, M., Athea, Y., Viollet, B., Mateo, P., Fortin, D., Leclerc, J., Hoerter, J., Ventura-Clapier, R., and Garnier, A. (2007) Activation of AMP kinase alpha1 subunit induces aortic vasorelaxation in mice. *J Physiol* 581, 1163-1171

50. Bess, E., Fissltheler, B., Fromel, T., and Fleming, I. (2011) Nitric oxide-induced activation of the AMP-activated protein kinase alpha2 subunit attenuates IkappaB kinase activity and inflammatory responses in endothelial cells. *PLoS One* 6, e20848

51. Xing, J., Wang, Q., Coughlan, K., Viollet, B., Moriasi, C., and Zou, M. H. (2013) Inhibition of AMP-Activated Protein Kinase Accentuates Lipopolysaccharide-Induced Lung Endothelial Barrier Dysfunction and Lung Injury in Vivo. *Am J Pathol*

52. Warden, S. M., Richardson, C., O'Donnell, J., Jr., Stapleton, D., Kemp, B. E., and Witters, L. A. (2001) Post-translational modifications of the beta-1 subunit of AMP-activated protein kinase affect enzyme activity and cellular localization. *Biochem J* 354, 275-283

Example 2

The AMPK Agonist AICAR Suppresses VEGF Stimulated Tube Formation, Transcytosis, Endocytosis, Caveolin-1 Phosphorylation and Prdx1/c-abl Dissociation This Example shows that AMPK activation inhibits VEGF tube formation through PTEN dependent dephosphorylation of Akt and suppresses VEGF induced caveolin-1 phosphorylation through stabilization of c-alb/prdx1 complex.

Materials and Methods

The following materials and methods were used in Example 2.

Materials Antibodies for (p-)VEGFR2, (p-)caveolin-1, (p-)c-Abl, (p-)Akt, (p-)PTEN, peroxiredoxin I (Prdx1), (p-)AMPK, AMPKα1, AMPKα2 and VE-cadherin were purchased from Cell Signaling Technologies (Beverly, Mass.). Antibodies for β-actin was purchased from Abcam (Cambridge, Mass.). CD31 and p-caveolin-1 (for immunofluorescence) were obtained from R&D Systems (Minneapolis, Minn.). Secondary antibodies of Alexa Fluor 488 goat anti-mouse IgG and Alexa Fluor 647 goat anti-rabbit IgG were purchased from Invitrogen (Carlsbad, Calif.). 5-amino-4-imidazole carboxamide riboside (AICAR), a pharmacological activator of AMPK, was purchased from Toronto Research Chemicals (Toronto, ON, Canada). 5-Iodotubericidin (IODO), dipyridamole (DPY) and suramin were purchased from Sigma (St. Louis, Mo.). VEGF was purchased from R&D Systems. Imatinib mesylate, a c-Abl inhibitor, was purchased from Cayman Chemicals (Ann Arbor, Mich.). The in vitro vascular permeability assay kit was from Millipore (Beverly, Mass., USA). SiRNAs targeting c-Abl, AMPKα1 and α2 and Prdx1, PTEN and control siRNA were purchased from Thermoscientific (Rockford, Ill.).

Cell cultures. Human umbilical vein endothelial cells (HUVECs) were cultured in endothelial growth medium (EGM, Lonza, Walkersville, Md.). Normal human dermal fibroblasts (NHDFs) were cultured in fibroblast basal medium (ATCC, Rockville, Md.). Cells were grown at 37° C. in a humidified atmosphere of 95% air, 5% $CO_2$. Experiments were performed on cells below passage 3 to 6 grown to 80%-90% confluence.

In Vitro Angiogenesis (Tube Formation) Assay.

To evaluate the effects of AICAR on angiogenesis, HUVECs were cocultured with NHDFs in a 24-well plate with or without VEGF and AICAR. NHDF cells were seeded at $1.0 \times 10^5$ cells/well and then cultured for 2 wks to form a fibroblast cell sheet. HUVECs were then seeded at $5.0 \times 10^3$ cells/well on the sheets, and the next day, AICAR (2 mM) and VEGF (12.5 ng/mL) were added to each well. Suramin (50 μM) was used as the inhibitor of VEGF. At 3, 7 and 10 days after treatment, cells were fixed at −20° C. in ethanol and acetone (1:1). Subsequently, cells were blocked with 1% bovine serum albumin (BSA) in phosphate-buffered saline for 30 min at room temperature, and then incubated with primary rabbit anti-human CD31 antibody overnight at 4° C. After the cells were washed with Tris-buffered saline (TBS), Alexa Flour 488 goat anti-rabbit IgG was applied for 2 h at room temperature. The tube length was quantified using a Kurabo Angiogenesis Image Analyzer (imaging software; Kurabo, Osaka, Japan).

In vitro vascular permeability assay. We conducted the in vitro vascular permeability assay using Alexa Flour 555-labeled bovine serum albumin (BSA) (Invitrogen) and an In Vitro Vascular Permeability Assay kit (Millipore). According to the manufacturer's instructions, HUVECs were seeded at a density of $1 \times 10^5$ on a collagen-coated polystyrene filter. After a confluent monolayer was formed, each chamber was treated with AICAR or stimulated with VEGF. To measure endothelial permeability, 100 μL of Alexa Flour 555-BSA solution (0.050 mg/mL) was added into the insert and incubated for 10 min, and then the insert was removed and 100 μL medium was collected from the bottom chamber. The fluorescent density of samples was analyzed on a SPECTRAmax GEMINI XS Microplate Spectrofluorometer (Molecular Devices, Sunnyvale, Calif.) at excitation and emission wavelengths of 555 nm and 565 nm, respectively.

Albumin endocytosis assay. After overnight serum starvation, HUVECs were pretreated with AICAR (2 mM) for 2 h and then stimulated with VEGF (12.5 ng/mL) for 10 min. We added BSA conjugated with Alexa 555 (50 μg/mL, Life Technologies, Gaithersburg, Md.) in the medium during the experiment. Cells on coverslips were washed three times with cold TBS and fixed in 100% methanol at 20° C. for 15 min. Cells were then permeabilized in 0.3% Triton X-100, 0.15% BSA in TBS with 0.05% Tween 20 (TBST) for 15 min at room temperature, and blocked with 0.5% skim milk in TBST for 60 min at room temperature. Cells were incubated in p-caveolin-1 antibody diluted 1:200 and VE-cadherin antibody diluted 1:400 overnight at 4° C., and then incubated for 2 h in secondary antibody diluted 1:300. Cells were then rinsed three times in TBST before mounting in Toto3 (Life Technologies). Images were acquired with a Leica TCS SP2 spectral confocal laser scanning microscope (Leica Microsystems, Wetzlar, Germany).

Protein extraction and western blotting. Protein extraction and Western blotting were carried out as described previously (Morizane et al. JBC (26)). We conducted a densitometric analysis of bands using ImageJ software. Lane-loading differences were normalized by β-actin.

Immunoprecipitation. Immunoprecipitation was performed with the Universal Magnetic Co-IP Kit (Active Motif North America, Carlsbad, Calif.) according to the manufacturer's instruction.

Small interfering RNA. Cells were transfected with siRNAs using a Nucleofection kit (Amaxa Biosystems, Gaithersburg, Md.), following the manufacturer's protocol. The medium was changed 6 h after transfection. The downregulation of each protein was evaluated 3 days after nucleofection.

Statistical analysis. Data are expressed as means±SDs. Statistical analyses were performed using the unpaired Student's t-test. Differences were considered significant at $p<0.01$ or $0.05$.

2.1 AMPK Activator AICAR Inhibits VEGF-Induced Vascular Tube Formation in an In-Vitro Model Through VEGFR2 Independent Mechanisms.

Co-culture of HUVECs and NHDFs in the presence of VEGF results in significant vascular tube formation. Addition of AICAR (0.25, 0.5, 1.0, 2.0 mM), led to a dose-dependent inhibition of tube formation (FIG. 8A,B). Phosphorylation of VEGFR2 and Akt (31-33) by VEGF are key steps of angiogenesis in addition to VEGF induced dissociation of VEGFR2 from Caveolin-1 in the caveolae (7). As seen in FIG. 8C-G, AICAR pretreatment had no effect on VEGFR2 phosphorylation or its dissociation from caveolin-1 upon VEGF stimulation, however it significantly suppressed and delayed VEGF induced Akt phosphorylation.

2.2 AICAR Activation of AMPK Leads to PTEN Dependent Dephosphorylation of Akt.

Figure 9A:
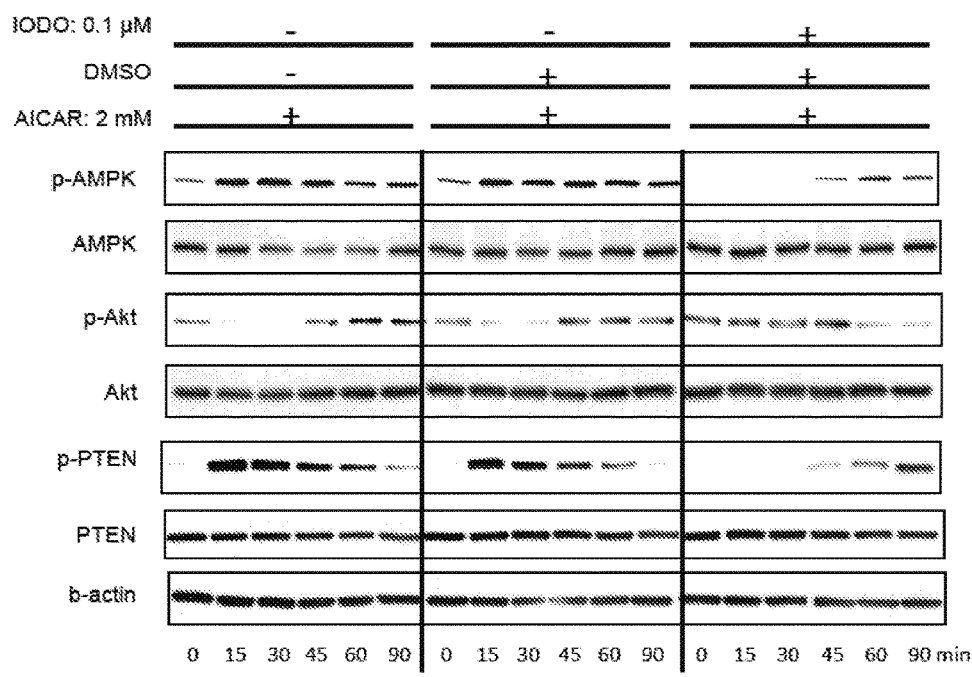
Figure 9B:
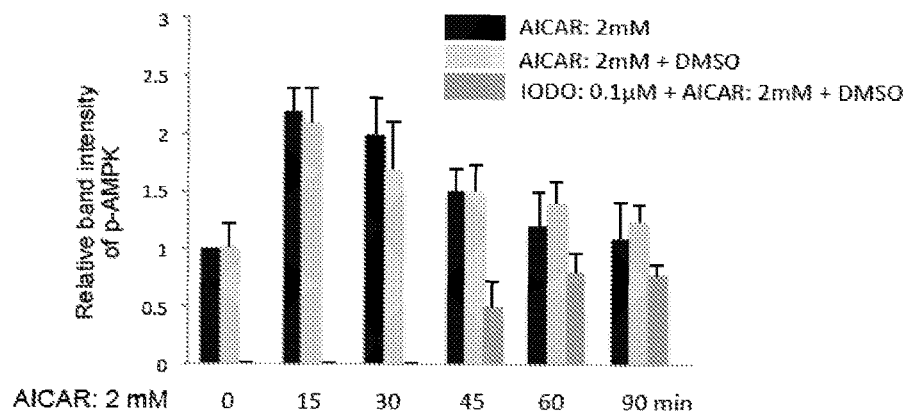
Figure 9C:
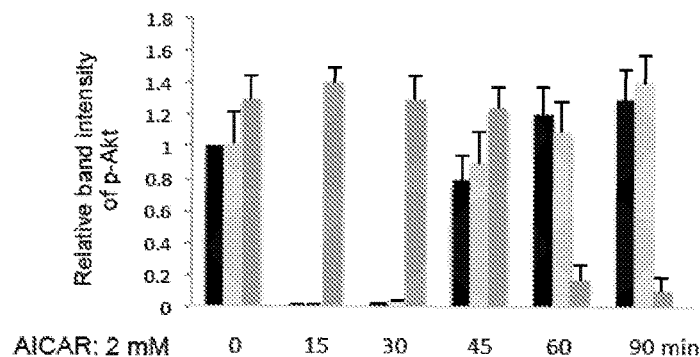
Figure 9D:
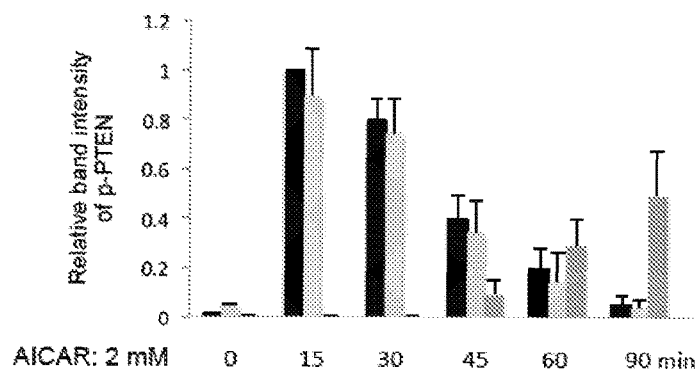
Figure 9E:
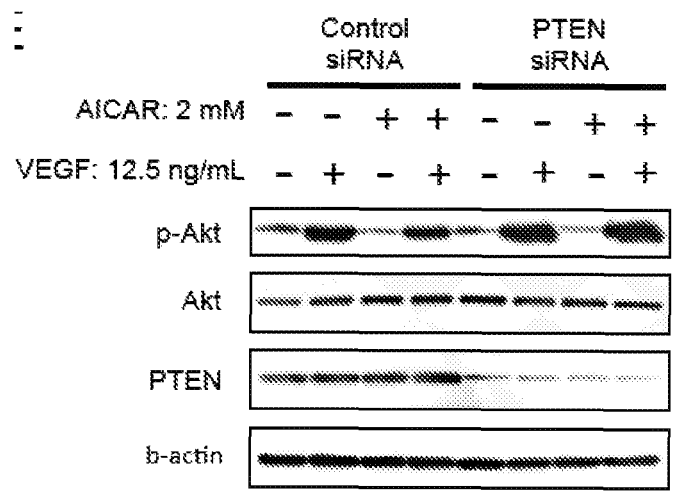
Figure 9F:
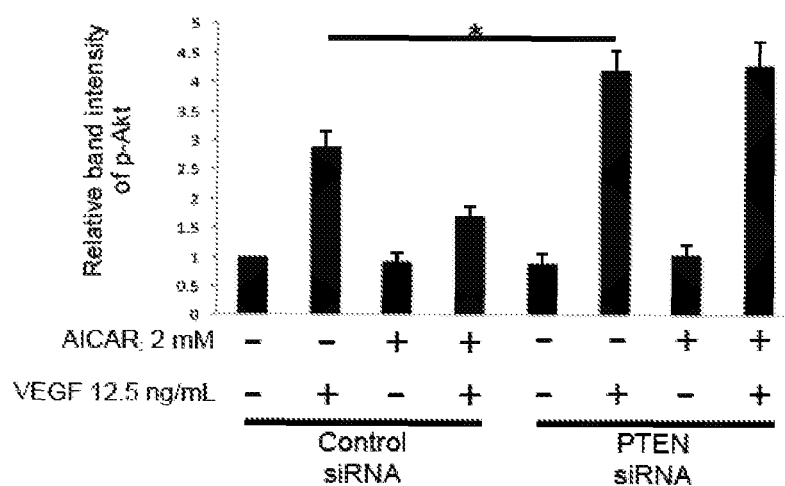

AICAR can mediate its function via both AMPK dependent and independent pathways (34-37) and there have been many conflicting reports on the relationship between AMPK and Akt phosphorylation depending on cell types and experimental system (38-42). Once AICAR enters a cell, it can be converted to either inosine or ZMP. Inosine inhibits cells by raising the adenosine concentration, which is independent of AMPK. By contrast, ZMP is activating the AMPK pathway. AICAR is converted to ZMP by adenosine kinase (AK), but this conversion is blocked by the AK inhibitor IODO (19,43). As shown in FIG. 9, AICAR treatment of endothelial cells resulted in AMPK and PTEN phosphorylation with similar time course, that was followed by Akt dephosphorylation. Pretreatment with IODO, suppressed and delayed the effects of AICAR on AMPK and PTEN phosphorylation and Akt dephosphorylation. This indicates that AMPK activation by AICAR is needed for the phosphorylation of PTEN and dephosphorylation of Akt (FIG. 9AD). In addition, PTEN knockdown by siRNA abrogated the effects of AICAR on Akt dephosphyralation, suggesting that its effects are PTEN dependent (FIG. 9E,F).

2.3 AICAR Inhibits VEGF-Induced Albumin Endocytosis and Leakage in HUVECs in an in Vitro Model and Suppresses VEGF-Induced Phosphorylation of Caveolin-1 and c-Abl.

Figure 10A:
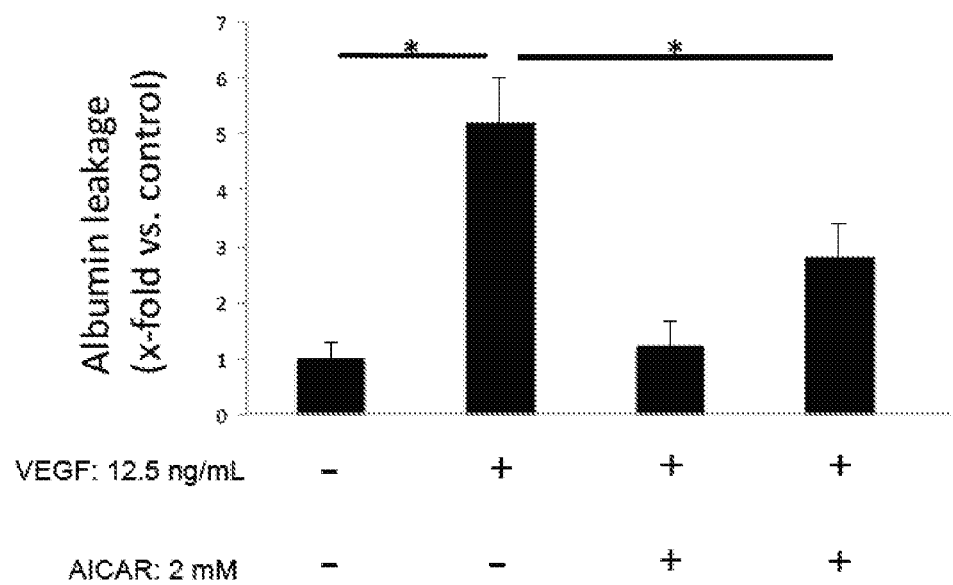
Figure 10B:
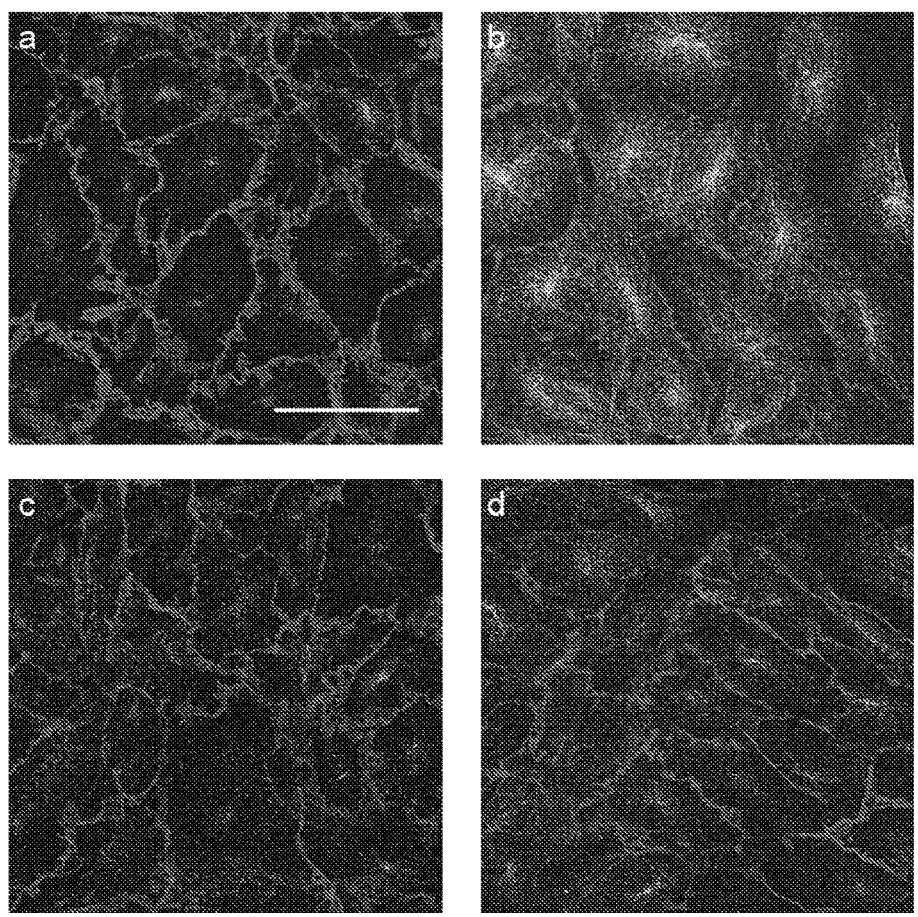

In addition to its role in angiogenesis, VEGF is also a powerful stimulus of endocytosis and vascular leakage. Exposure of HUVEC monolayer to VEGF results in increased albumin leakage (FIG. 10A) and endocytosis (FIG. 10B) that can be significantly suppressed by pretreatment with AICAR (FIG. 10A,B). Increased VEGF permeability is thought to be partially mediated by Caveolin-1 phosphorylation on Y14 (7,8). Caveolin-1 phosphyrylation requires c-Abl, at least under certain conditions such as oxidative stress (15). As shown in FIG. 11AC, AICAR significantly suppressed the VEGF induced phosphorylation of caveolin-1 and c-Abl.

2.4 AICAR Suppresses VEGF-Induced Caveolin-1, c-Abl and Akt Phosphorylation Likely via AMPK.

Figures 12A, 12B, 12C:
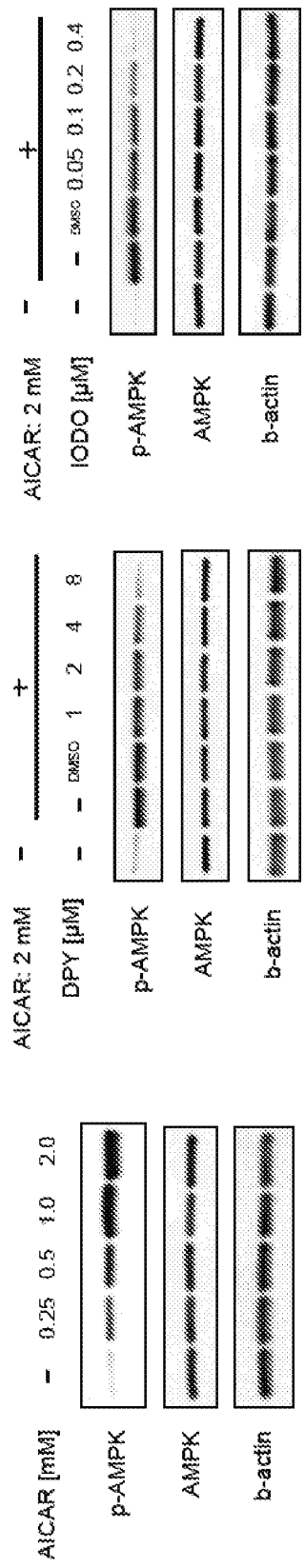
Figure 12D:
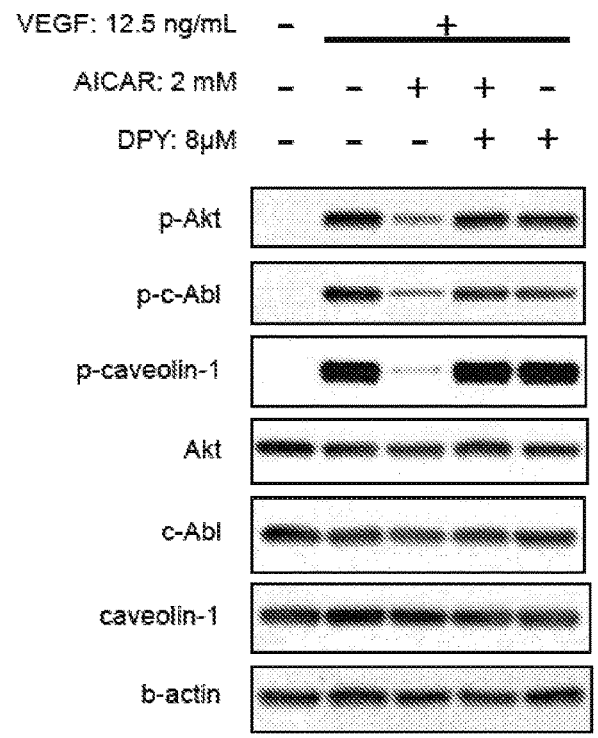
Figure 12E:
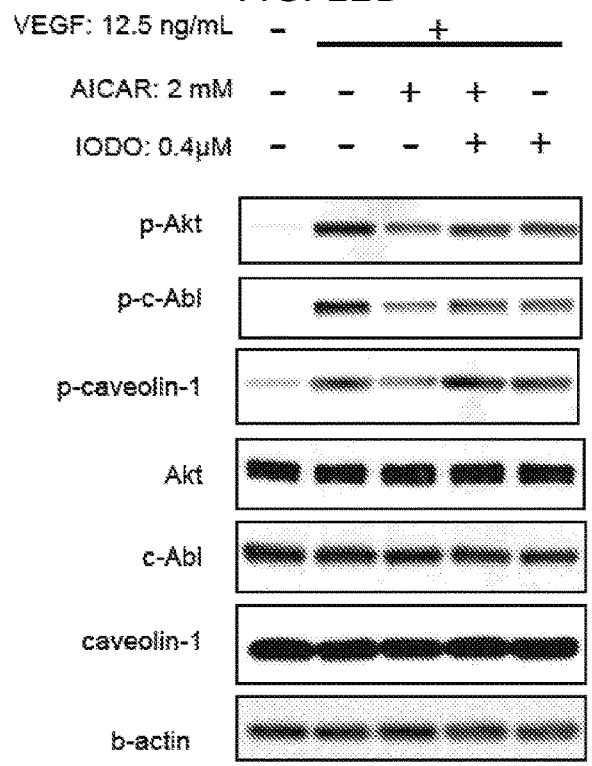
Figure 12F:
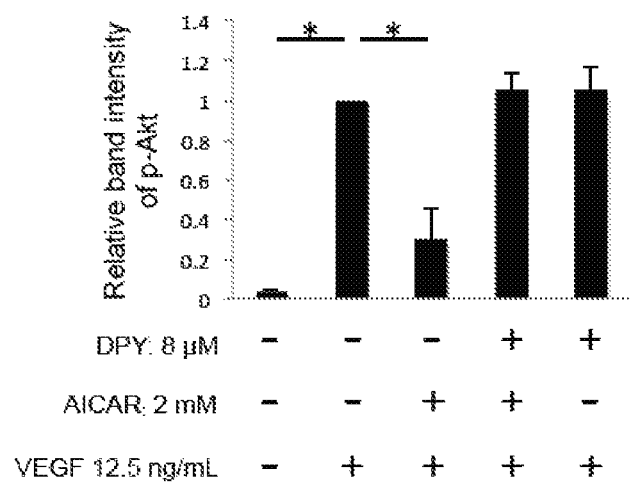
Figure 12G:
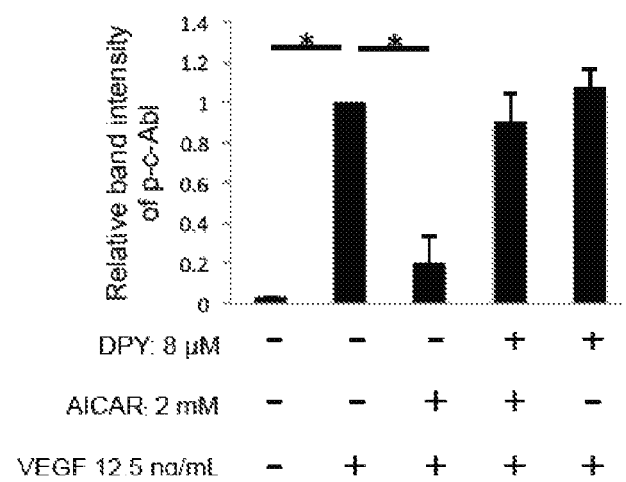
Figure 12H:
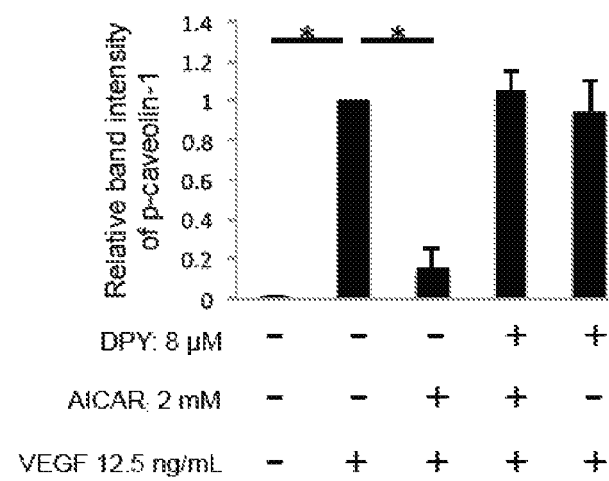
Figure 12I:
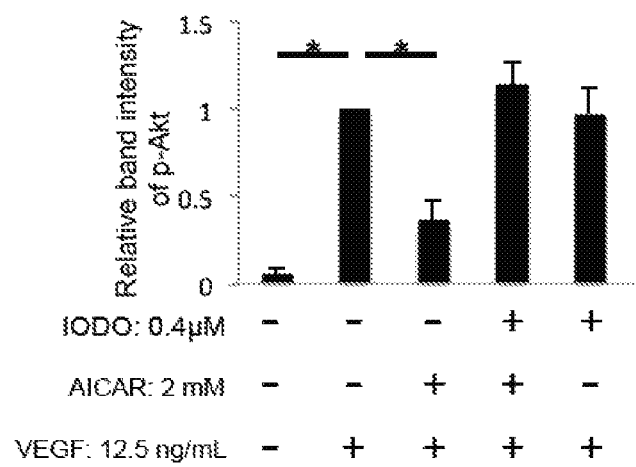
Figure 12J:
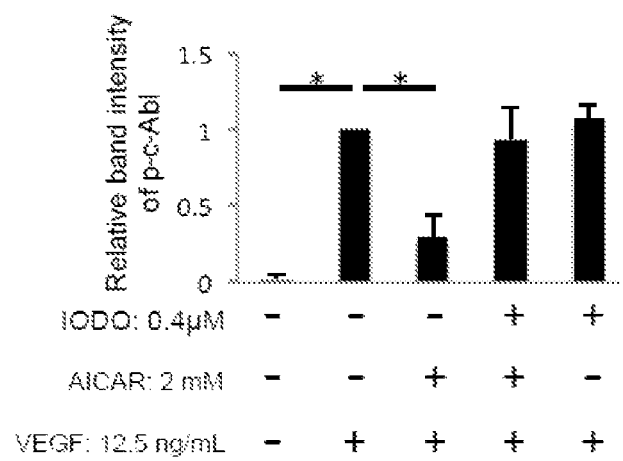
Figure 12K:
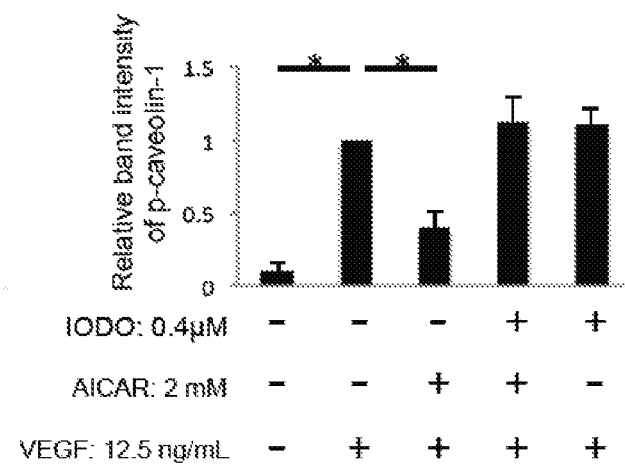

To determine if the effects of AICAR are mediated via AMPK, several set of experiments were performed. AICAR administration resulted in dose dependent AMPK phosphorylation in HUVEC cells (FIG. 12A). To confirm AMPK phosphorylation was due to intracellular AICAR, HUVEC cells were pretreated with Adenosine transporter inhibitor DPY or with the AK inhibtor IODO (19,43). Blocking AICAR receptors with DPY inhibited AMPK phosphorylation (FIG. 12B). IODO inhibition of AICAR conversion to ZMP, the direct activator of AMPK, significantly abolished the inhibitory effect of AICAR on the phosphorylation of caveolin-1, c-Abl and Akt (FIG. 12D,E). These results suggest that AMPK activation is a key process for the inhibitory effect of AICAR on VEGF induced phosphorylation of caveolin-1, c-Abl and Akt phosphorylation.

2.5 Both AMPKα1 and α2 Isoforms are Required for AICAR Inhibition of VEGF Dependent Caveolin-1, c-Abl and Akt Phosphorylation.

AMPK has two catalytic subunit isoforms (AMPKα1 and α2) (16,17,26). To determine the role of each isoform, we used siRNA. Knockdown of either isoform of AMPKα abolished the inhibitory effect of AICAR on the VEGF-induced phosphorylation of caveolin-1, c-Abl and Akt (FIG. 13). These results suggest that both AMPK isoforms (α1 and α2) are required for AICAR to inhibit VEGF dependent c-alb, Akt, and caveolin-1 phosphorylation.

2.6 c-Abl is Required for VEGF Dependent Caveolin-1 Phosphorylation.

Figure 14A:
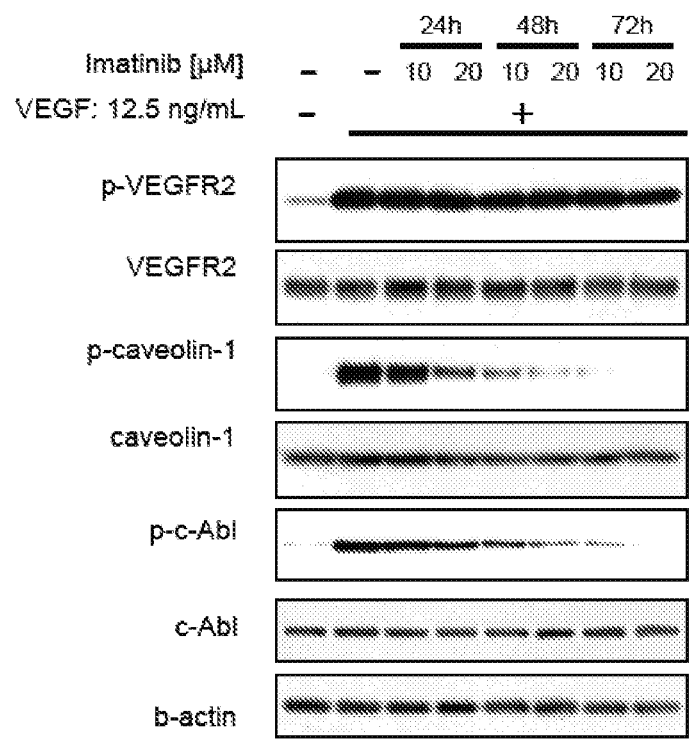
Figure 14B:
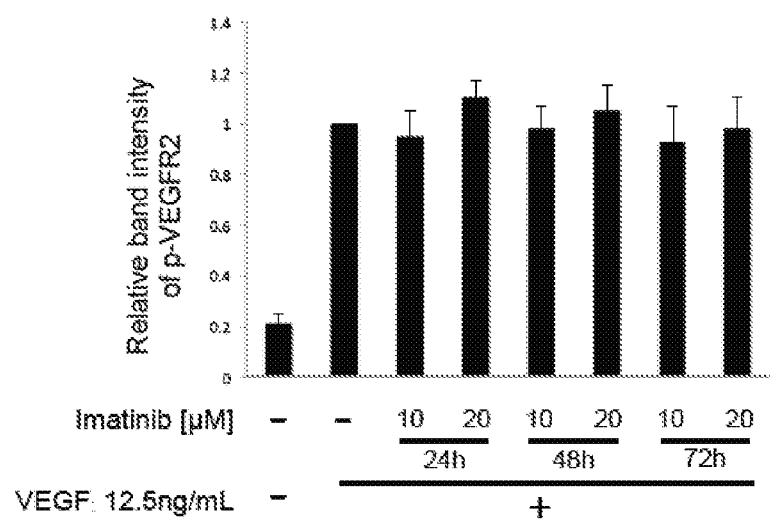
Figure 14E:
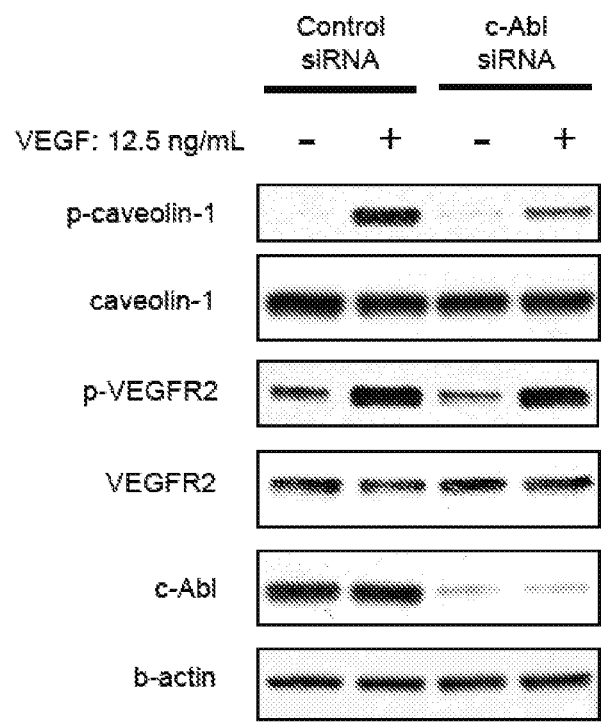
Figure 14F:
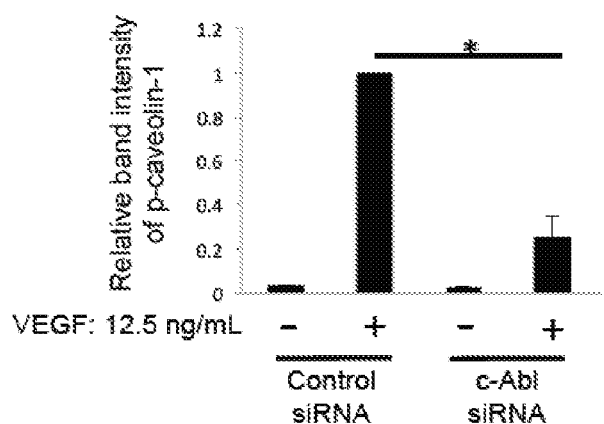
Figure 14G:
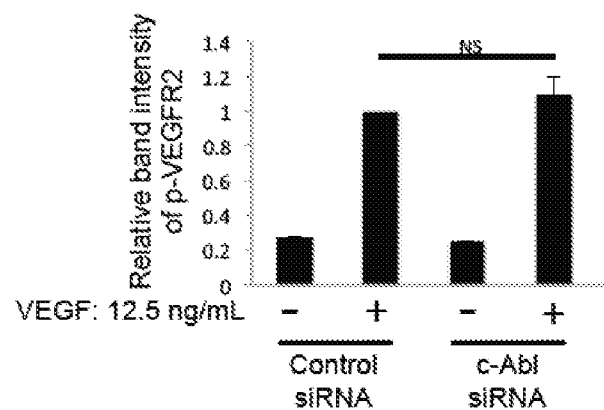

To determine the role of c-Abl in the VEGF-induced phosphorylation of caveolin-1, we used a c-Abl inhibitor, imatinib mesylate (44,45). As shown in FIG. 14A-D, imatinib mesylate inhibited the VEGF-induced phosphorylation of caveolin-1 and c-Abl in a time and dose dependent manner, indicating that c-Abl is an upstream kinase of caveolin-1 in HUVECs. We next investigated the role of c-Abl in the inhibitory effect of AICAR on canveolin-1 phosphorylation by the knockdown of c-Abl with siRNA. Deletion of c-Abl resulted in a significant decrease in caveolin-1 phosphorylation after VEGF exposure (FIG. 14E-G). These results indicate that VEGF induced caveolin-1 phosphorylation requires c-abl.

2.7 Prdx1 is Indispensable for the Inhibitory Effect of AMPK Activator AICAR on the VEGF-Induced Phosphorylation of Caveolin-1 and c-Abl.

Figure 15A:
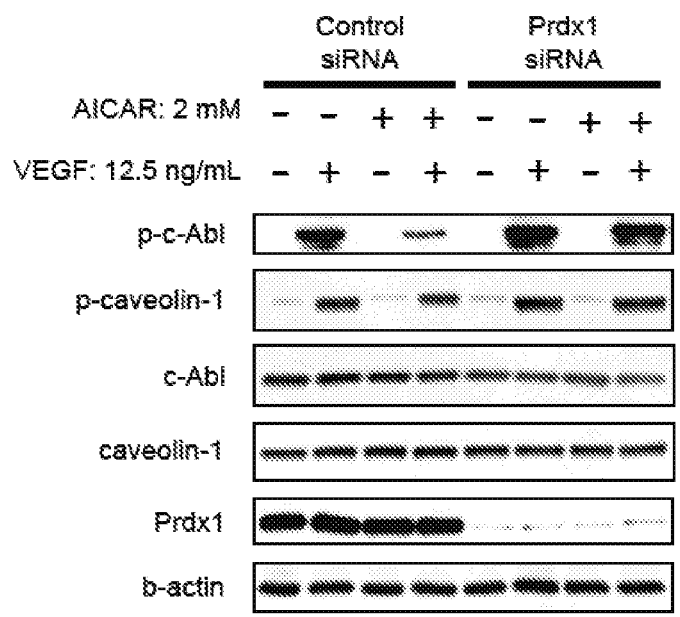
Figure 15B:
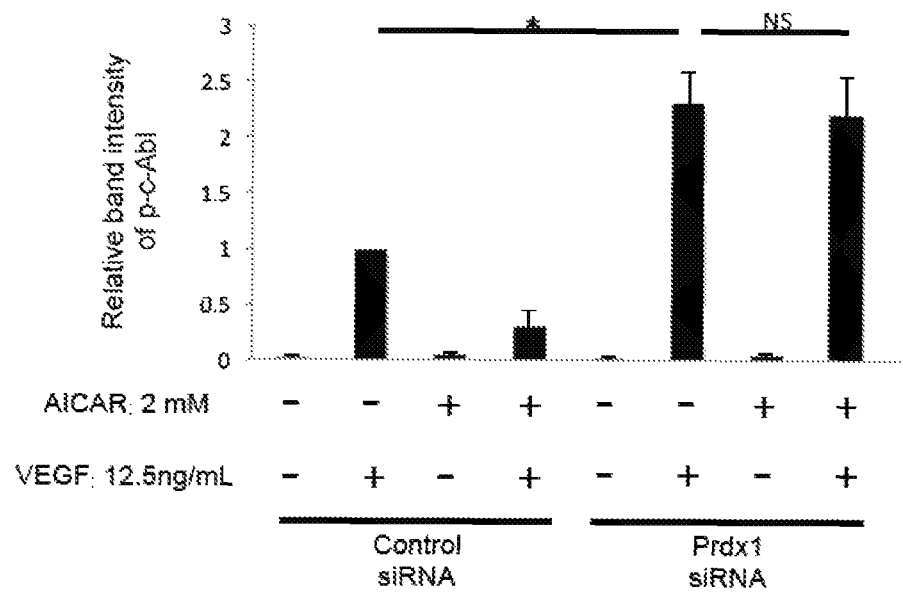
Figure 15C:
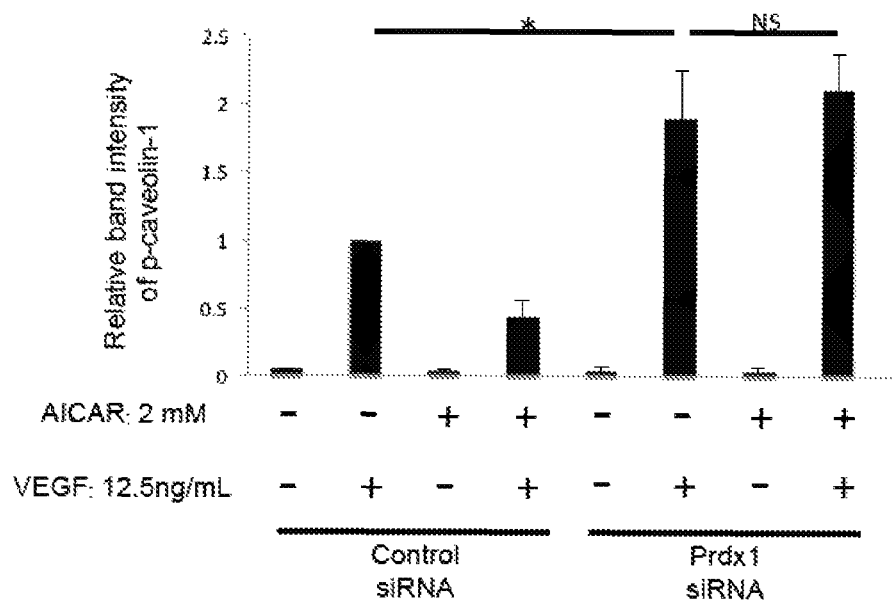

Prdx1, one of the antioxidant enzymes that exists in a complex with c-Abl and plays a protective role in cells against oxidative stress (46-49). Dissociation of this complex is thought to lead to phosphorylation of c-Abl and subsequent Caveolin-1 phosphorylation by c-Abl. To investigate the role of this complex on AICAR inhibition of VEGF induced Caveolin-1 phosphorylation, we knocked down Prdx1 in HUVECs with siRNA. As shown in FIG. 15A-C, knockdown of prdx1 resulted in increased phosphorylation of caveolin-1 and c-Abl after VEGF exposure. Furthermore, lack of prdx1 abolished the inhibitory effect of AICAR on the VEGF-induced phosphorylation of caveolin-1 and c-Abl. These results indicate that prdx1 is indispensable for the inhibitory effect of AMPK activator AICAR on the VEGF-induced phosphorylation of caveolin-1 and c-Abl.

2.8 AMPK Inhibits VEGF Dependent Caveolin-1 Phosphorylation by Suppressing the Dissociation Between prdx1 and c-Abl.

Figure 15D:
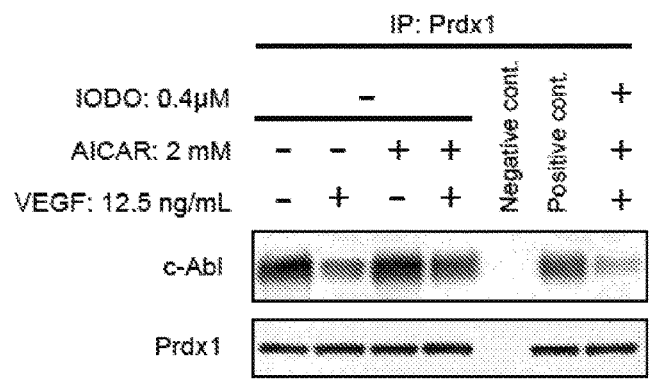
Figure 15E:
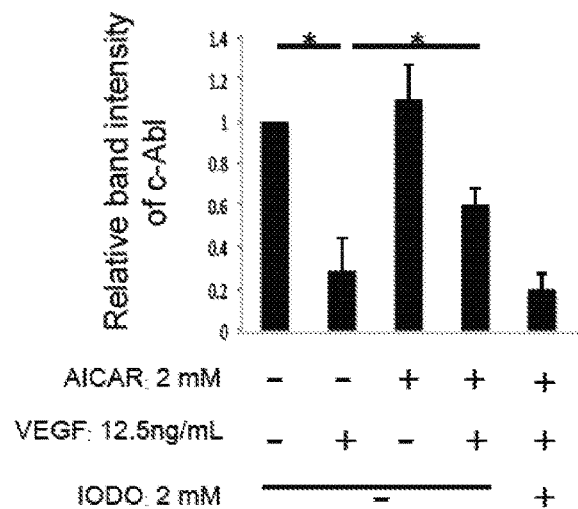
Figure 15F:
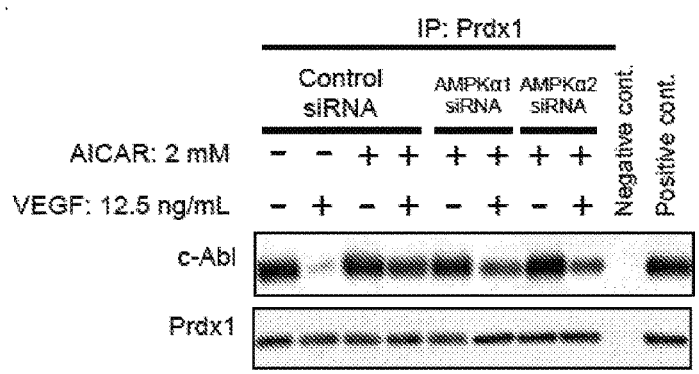
Figure 15G:
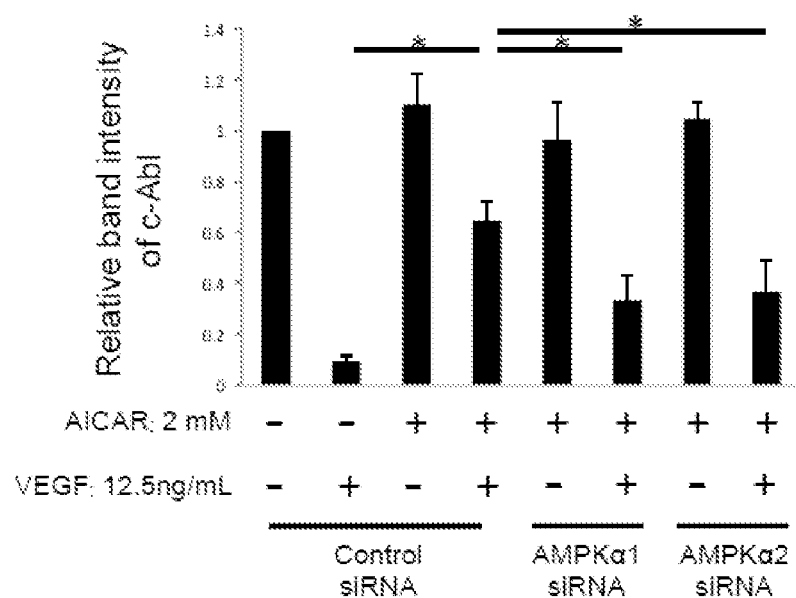

AICAR inhibited the VEGF induced dissociation between prdx1 and c-Abl (FIG. 15D). This inhibition was abrogated by the AK inhibitor IODO suggesting that the effects of AICAR were AMPK mediated (FIGS. 15D,E). Supporting this conclusion, siRNA knockdown of either AMPKα1 or α2 isoform decreased the ability of AICAR to inhibit the VEGF induced dissociation between prdx1 and c-Abl (FIGS. 15F,G). These results indicated that AMPK mediates the AICAR suppression of VEGF induced prdx1/c-abl dissociation and subsequent caveolin-1 phosphorylation.

REFERENCES FOR EXAMPLE 2

1. Shibuya, M., and Claesson-Welsh, L. (2006) Signal transduction by VEGF receptors in regulation of angiogenesis and lymphangiogenesis. *Exp Cell Res* 312, 549-560
2. Holmes, K., Roberts, O. L., Thomas, A. M., and Cross, M. J. (2007) Vascular endothelial growth factor receptor-2: structure, function, intracellular signaling and therapeutic inhibition. *Cell Signal* 19, 2003-2012
3. Olsson, A. K., Dimberg, A., Kreuger, J., and Claesson-Welsh, L. (2006) VEGF receptor signaling—in control of vascular function. *Nat Rev Mol Cell Biol* 7, 359-371
4. Komarova, Y., and Malik, A. B. (2010) Regulation of endothelial permeability via paracellular and transcellular transport pathways. *Annu Rev Physiol* 72, 463-493
5. Bates, D. O. (2010) Vascular endothelial growth factors and vascular permeability. *Cardiovasc Res* 87, 262-271
6. Bates, D. O., and Harper, S. J. (2002) Regulation of vascular permeability by vascular endothelial growth factors. *Vascul Pharmacol* 39, 225-237
7. Feng, Y., Venema, V. J., Venema, R. C., Tsai, N., Behzadian, M. A., and Caldwell, R. B. (1999) VEGF-induced permeability increase is mediated by caveolae. *Invest Ophthalmol Vis Sci* 40, 157-167
8. Zhao, L. N., Yang, Z. H., Liu, Y. H., Ying, H. Q., Zhang, H., and Xue, Y. X. (2011) Vascular endothelial growth factor increases permeability of the blood-tumor barrier via caveolae-mediated transcellular pathway. *J Mol Neurosci* 44, 122-129

9. Labrecque, L., Royal, I., Surprenant, D. S., Patterson, C., Gingras, D., and Beliveau, R. (2003) Regulation of vascular endothelial growth factor receptor-2 activity by caveolin-1 and plasma membrane cholesterol. *Mol Biol Cell* 14, 334-347

10. Tahir, S. A., Park, S., and Thompson, T. C. (2009) Caveolin-1 regulates VEGF-stimulated angiogenic activities in prostate cancer and endothelial cells. *Cancer Biol Ther* 8, 2286-2296

11. Yamada, E. (1955) The fine structure of the gall bladder epithelium of the mouse. *J Biophys Biochem Cytol* 1, 445-458

12. Schubert, W., Frank, P. G., Razani, B., Park, D. S., Chow, C. W., and Lisanti, M. P. (2001) Caveolae-deficient endothelial cells show defects in the uptake and transport of albumin in vivo. *J Biol Chem* 276, 48619-48622

13. Hu, G., and Minshall, R. D. (2009) Regulation of transendothelial permeability by Src kinase. *Microvasc Res* 77, 21-25

14. Hu, G., Vogel, S. M., Schwartz, D. E., Malik, A. B., and Minshall, R. D. (2008) Intercellular adhesion molecule-1-dependent neutrophil adhesion to endothelial cells induces caveolae-mediated pulmonary vascular hyperpermeability. *Circ Res* 102, e120-131

15. Sanguinetti, A. R., and Mastick, C. C. (2003) c-Abl is required for oxidative stress-induced phosphorylation of caveolin-1 on tyrosine 14. *Cell Signal* 15, 289-298

16. Hardie, D. G., and Hawley, S. A. (2001) AMP-activated protein kinase: the energy charge hypothesis revisited. *Bioessays* 23, 1112-1119

17. Viollet, B., Athea, Y., Mounter, R., Guigas, B., Zarrinpashneh, E., Horman, S., Lantier, L., Hebrard, S., Devin-Leclerc, J., Beauloye, C., Foretz, M., Andreelli, F., Ventura-Clapier, R., and Bertrand, L. (2009) AMPK: Lessons from transgenic and knockout animals. *Front Biosci* 14, 19-44

18. Wang, W., and Guan, K. L. (2009) AMP-activated protein kinase and cancer. *Acta Physiol (Oxf)* 196, 55-63

19. Theodoropoulou, S., Kolovou, P. E., Morizane, Y., Kayama, M., Nicolaou, F., Miller, J. W., Gragoudas, E., Ksander, B. R., and Vavvas, D. G. (2010) Retinoblastoma cells are inhibited by aminoimidazole carboxamide ribonucleotide (AICAR) partially through activation of AMP-dependent kinase. *FASEB J* 24, 2620-2630

20. Kim, S. A., and Choi, H. C. (2012) Metformin inhibits inflammatory response via AMPK-PTEN pathway in vascular smooth muscle cells. *Biochem Biophys Res Commun* 425, 866-872

21. Myers, M. P., Stolarov, J. P., Eng, C., Li, J., Wang, S. I., Wigler, M. H., Parsons, R., and Tonks, N. K. (1997) P-TEN, the tumor suppressor from human chromosome 10q23, is a dual-specificity phosphatase. *Proc Natl Acad Sci USA* 94, 9052-9057

22. Tamura, M., Gu, J., Matsumoto, K., Aota, S., Parsons, R., and Yamada, K. M. (1998) Inhibition of cell migration, spreading, and focal adhesions by tumor suppressor PTEN. *Science* 280, 1614-1617

23. Theodoropoulou, S., Brodowska, K., Kayama, M., Morizane, Y., Miller, J. W., Gragoudas, E. S., and Vavvas, D. G. (2013) Aminoimidazole Carboxamide Ribonucleotide (AICAR) Inhibits the Growth of Retinoblastoma In Vivo by Decreasing Angiogenesis and Inducing Apoptosis. *PLoS One* 8, e52852

24. Suzuki, J., Manola, A., Murakami, Y., Morizane, Y., Takeuchi, K., Kayama, M., Miller, J. W., Sobrin, L., and Vavvas, D. G. (2011) Inhibitory effect of aminoimidazole carboxamide ribonucleotide (AICAR) on endotoxin-induced uveitis in rats. *Invest Ophthalmol Vis Sci* 52, 6565-6571

25. Suzuki, J., Yoshimura, T., Simeonova, M., Takeuchi, K., Murakami, Y., Morizane, Y., Miller, J. W., Sobrin, L., and Vavvas, D. G. (2012) Aminoimidazole carboxamide ribonucleotide ameliorates experimental autoimmune uveitis. *Invest Ophthalmol Vis Sci* 53, 4158-4169

26. Morizane, Y., Thanos, A., Takeuchi, K., Murakami, Y., Kayama, M., Trichonas, G., Miller, J., Foretz, M., Viollet, B., and Vavvas, D. G. (2011) AMP-activated protein kinase suppresses matrix metalloproteinase-9 expression in mouse embryonic fibroblasts. *J Biol Chem* 286, 16030-16038

27. Creighton, J., Jian, M., Sayner, S., Alexeyev, M., and Insel, P. A. (2011) Adenosine monophosphate-activated kinase alpha1 promotes endothelial barrier repair. *FASEB J* 25, 3356-3365

28. Ahluwalia, A., and Tamawski, A. S. (2011) Activation of the metabolic sensor-AMP activated protein kinase reverses impairment of angiogenesis in aging myocardial microvascular endothelial cells. Implications for the aging heart. *J Physiol Pharmacol* 62, 583-587

29. Stahmann, N., Woods, A., Spengler, K., Heslegrave, A., Bauer, R., Krause, S., Viollet, B., Carling, D., and Heller, R. (2010) Activation of AMP-activated protein kinase by vascular endothelial growth factor mediates endothelial angiogenesis independently of nitric-oxide synthase. *J Biol Chem* 285, 10638-10652

30. Peyton, K. J., Liu, X. M., Yu, Y., Yates, B., and Durante, W. (2012) Activation of AMP-activated protein kinase inhibits the proliferation of human endothelial cells. *J Pharmacol Exp Ther* 342, 827-834

31. Karkkainen, M. J., and Petrova, T. V. (2000) Vascular endothelial growth factor receptors in the regulation of angiogenesis and lymphangiogenesis. *Oncogene* 19, 5598-5605

32. Rahimi, N., Dayanir, V., and Lashkari, K. (2000) Receptor chimeras indicate that the vascular endothelial growth factor receptor-1 (VEGFR-1) modulates mitogenic activity of VEGFR-2 in endothelial cells. *J Biol Chem* 275, 16986-16992

33. Claesson-Welsh, L. (2003) Signal transduction by vascular endothelial growth factor receptors. *Biochem Soc Trans* 31, 20-24

34. Guigas, B., Bertrand, L., Taleux, N., Foretz, M., Wiernsperger, N., Vertommen, D., Andreelli, F., Viollet, B., and Hue, L. (2006) 5-Aminoimidazole-4-carboxamide-1-beta-D-ribofuranoside and metformin inhibit hepatic glucose phosphorylation by an AMP-activated protein kinase-independent effect on glucokinase translocation. *Diabetes* 55, 865-874

35. Guigas, B., Taleux, N., Foretz, M., Detaille, D., Andreelli, F., Viollet, B., and Hue, L. (2007) AMP-activated protein kinase-independent inhibition of hepatic mitochondrial oxidative phosphorylation by AICA riboside. *Biochem J* 404, 499-507

36. Mukhtar, M. H., Payne, V. A., Arden, C., Harbottle, A., Khan, S., Lange, A. J., and Agius, L. (2008) Inhibition of glucokinase translocation by AMP-activated protein kinase is associated with phosphorylation of both GKRP and 6-phosphofructo-2-kinase/fructose-2,6-bisphosphatase. *Am J Physiol Regul Integr Comp Physiol* 294, R766-774

37. Foretz, M., Hebrard, S., Leclerc, J., Zarrinpashneh, E., Soty, M., Mithieux, G., Sakamoto, K., Andreelli, F., and Viollet, B. (2010) Metformin inhibits hepatic gluconeogenesis in mice independently of the LKB1/AMPK pathway via a decrease in hepatic energy state. *J Clin Invest* 120, 2355-2369
38. Leclerc, G. M., Leclerc, G. J., Fu, G., and Barredo, J. C. (2010) AMPK-induced activation of Akt by AICAR is mediated by IGF-1R dependent and independent mechanisms in acute lymphoblastic leukemia. *J Mol Signal* 5, 15
39. Ouchi, N., Kobayashi, H., Kihara, S., Kumada, M., Sato, K., Inoue, T., Funahashi, T., and Walsh, K. (2004) Adiponectin stimulates angiogenesis by promoting cross-talk between AMP-activated protein kinase and Akt signaling in endothelial cells. *J Biol Chem* 279, 1304-1309
40. Zhao, L., Wen, Z. H., Jia, C. H., Li, M., Luo, S. Q., and Bai, X. C. (2011) Metformin induces G1 cell cycle arrest and inhibits cell proliferation in nasopharyngeal carcinoma cells. *Anat Rec (Hoboken)* 294, 1337-1343
41. Kovacic, S., Soltys, C. L., Barr, A. J., Shiojima, I., Walsh, K., and Dyck, J. R. (2003) Akt activity negatively regulates phosphorylation of AMP-activated protein kinase in the heart. *J Biol Chem* 278, 39422-39427
42. Tzatsos, A., and Tsichlis, P. N. (2007) Energy depletion inhibits phosphatidylinositol 3-kinase/Akt signaling and induces apoptosis via AMP-activated protein kinase-dependent phosphorylation of IRS-1 at Ser-794. *J Biol Chem* 282, 18069-18082
43. Sanz, P. (2008) AMP-activated protein kinase: structure and regulation. *Curr Protein Pept Sci* 9, 478-492
44. Muller, B. A. (2009) Imatinib and its successors—how modern chemistry has changed drug development. *Curr Pharm Des* 15, 120-133
45. Druker, B. J. (2008) Translation of the Philadelphia chromosome into therapy for CML. *Blood* 112, 4808-4817
46. Wen, S. T., and Van Etten, R. A. (1997) The PAG gene product, a stress-induced protein with antioxidant properties, is an Abl SH3-binding protein and a physiological inhibitor of c-Abl tyrosine kinase activity. *Genes Dev* 11, 2456-2467
47. Prosperi, M. T., Ferbus, D., Rouillard, D., and Goubin, G. (1998) The pag gene product, a physiological inhibitor of c-abl tyrosine kinase, is overexpressed in cells entering S phase and by contact with agents inducing oxidative stress. *FEBS Lett* 423, 39-44
48. Cao, J., Schulte, J., Knight, A., Leslie, N. R., Zagozdzon, A., Bronson, R., Manevich, Y., Beeson, C., and Neumann, C. A. (2009) Prdx1 inhibits tumorigenesis via regulating PTEN/AKT activity. *EMBO J* 28, 1505-1517
49. Morell, M., Espargaro, A., Aviles, F. X., and Ventura, S. (2007) Detection of transient protein-protein interactions by bimolecular fluorescence complementation: the Abl-SH3 case. *Proteomics* 7, 1023-1036
50. Wang, F., Song, X., Zhou, M., Wei, L., Dai, Q., Li, Z., Lu, N., and Guo, Q. (2012) Wogonin inhibits H(2)O(2)-induced vascular permeability through suppressing the phosphorylation of caveolin-1. *Toxicology*
51. Russell, R. R., 3rd, Li, J., Coven, D. L., Pypaert, M., Zechner, C., Palmeri, M., Giordano, F. J., Mu, J., Birnbaum, M. J., and Young, L. H. (2004) AMP-activated protein kinase mediates ischemic glucose uptake and prevents postischemic cardiac dysfunction, apoptosis, and injury. *J Clin Invest* 114, 495-503
52. Nagata, D., Mogi, M., and Walsh, K. (2003) AMP-activated protein kinase (AMPK) signaling in endothelial cells is essential for angiogenesis in response to hypoxic stress. *J Biol Chem* 278, 31000-31006
53. Ouchi, N., Shibata, R., and Walsh, K. (2005) AMP-activated protein kinase signaling stimulates VEGF expression and angiogenesis in skeletal muscle. *Circ Res* 96, 838-846
54. Zou, M. H., Hou, X. Y., Shi, C. M., Kirkpatick, S., Liu, F., Goldman, M. H., and Cohen, R. A. (2003) Activation of 5'-AMP-activated kinase is mediated through c-Src and phosphoinositide 3-kinase activity during hypoxia-reoxygenation of bovine aortic endothelial cells. Role of peroxynitrite. *J Biol Chem* 278, 34003-34010
55. Reihill, J. A., Ewart, M. A., and Salt, I. P. (2011) The role of AMP-activated protein kinase in the functional effects of vascular endothelial growth factor-A and -B in human aortic endothelial cells. *Vasc Cell* 3, 9
56. Zhou, J., Yang, Z., Tsuji, T., Gong, J., Xie, J., Chen, C., Li, W., Amar, S., and Luo, Z. (2011) LITAF and TNFSF15, two downstream targets of AMPK, exert inhibitory effects on tumor growth. *Oncogene* 30, 1892-1900
57. Levine, Y. C., Li, G. K., and Michel, T. (2007) Agonist-modulated regulation of AMP-activated protein kinase (AMPK) in endothelial cells. Evidence for an AMPK→Rac1→Akt→endothelial nitric-oxide synthase pathway. *J Biol Chem* 282, 20351-20364
58. Ceolotto, G., Gallo, A., Papparella, I., Franco, L., Murphy, E., Tori, E., Pagnin, E., Fadini, G. P., Albiero, M., Semplicini, A., and Avogaro, A. (2007) Rosiglitazone reduces glucose-induced oxidative stress mediated by NAD(P)H oxidase via AMPK-dependent mechanism. *Arterioscler Thromb Vasc Biol* 27, 2627-2633
59. Deng, G., Long, Y., Yu, Y. R., and Li, M. R. (2010) Adiponectin directly improves endothelial dysfunction in obese rats through the AMPK-eNOS Pathway. *Int J Obes (Lond)* 34, 165-171
60. Rothberg, K. G., Heuser, J. E., Donzell, W. C., Ying, Y. S., Glenney, J. R., and Anderson, R. G. (1992) Caveolin, a protein component of caveolae membrane coats. *Cell* 68, 673-682
61. Glenney, J. R., Jr., and Soppet, D. (1992) Sequence and expression of caveolin, a protein component of caveolae plasma membrane domains phosphorylated on tyrosine in Rous sarcoma virus-transformed fibroblasts. *Proc Natl Acad Sci USA* 89, 10517-10521
62. Aoki, T., Nomura, R., and Fujimoto, T. (1999) Tyrosine phosphorylation of caveolin-1 in the endothelium. *Exp Cell Res* 253, 629-636
63. Ko, Y. G., Liu, P., Pathak, R. K., Craig, L. C., and Anderson, R. G. (1998) Early effects of pp60(v-src) kinase activation on caveolae. *J Cell Biochem* 71, 524-535
64. Lassila, M., Allen, T. J., Cao, Z., Thallas, V., Jandeleit-Dahm, K. A., Candido, R., and Cooper, M. E. (2004) Imatinib attenuates diabetes-associated atherosclerosis. *Arterioscler Thromb Vasc Biol* 24, 935-942
65. Hagerkvist, R., Makeeva, N., Elliman, S., and Welsh, N. (2006) Imatinib mesylate (Gleevec) protects against streptozotocin-induced diabetes and islet cell death in vitro. *Cell Biol Int* 30, 1013-1017
66. Hagerkvist, R., Sandler, S., Mokhtari, D., and Welsh, N. (2007) Amelioration of diabetes by imatinib mesylate (Gleevec): role of beta-cell NF-kappaB activation and anti-apoptotic preconditioning. *FASEB J* 21, 618-628
67. Louvet, C., Szot, G. L., Lang, J., Lee, M. R., Martinier, N., Bollag, G., Zhu, S., Weiss, A., and Bluestone, J. A. (2008) Tyrosine kinase inhibitors reverse type 1 diabetes in nonobese diabetic mice. *Proc Natl Acad Sci USA* 105, 18895-18900

68. Jeyabalan, J., Shah, M., Viollet, B., and Chenu, C. (2012) AMP-activated protein kinase pathway and bone metabolism. *J Endocrinol* 212, 277-290
69. Gayard, M., Guilluy, C., Rousselle, A., Viollet, B., Henrion, D., Pacaud, P., Loirand, G., and Rolli-Derkinderen, M. (2011) AMPK alpha 1-induced RhoA phosphorylation mediates vasoprotective effect of estradiol. *Arterioscler Thromb Vasc Biol* 31, 2634-2642
70. Goirand, F., Solar, M., Athea, Y., Viollet, B., Mateo, P., Fortin, D., Leclerc, J., Hoerter, J., Ventura-Clapier, R., and Garnier, A. (2007) Activation of AMP kinase alpha1 subunit induces aortic vasorelaxation in mice. *J Physiol* 581, 1163-1171
71. Bess, E., Fisslthaler, B., Fromel, T., and Fleming, I. (2011) Nitric oxide-induced activation of the AMP-activated protein kinase alpha2 subunit attenuates IkappaB kinase activity and inflammatory responses in endothelial cells. *PLoS One* 6, e20848
72. Xing, J., Wang, Q., Coughlan, K., Viollet, B., Moriasi, C., and Zou, M. H. (2013) Inhibition of AMP-Activated Protein Kinase Accentuates Lipopolysaccharide-Induced Lung Endothelial Barrier Dysfunction and Lung Injury in Vivo. *Am J Pathol*

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating ocular neovascularization characterized by surface, corneal, retinal, choroidal, uveal, or iris neovascularization in a mammal, the method comprising: identifying a mammal in need of reduced or delayed ocular neovascularization; and administering to the mammal an effective amount of one or both of: (i) an amp-activated protein kinase (AMPK) activator selected from the group consisting of guanidine; galegine; antifolate drugs that inhibit AICAR transformylase; phenobarbital; A-769662; PT1; and salicylate, wherein the AMPK activator is not methotrexate or rosiglitazone, or (ii) a Phosphatase and tensin homolog deleted on chromosome 10 (PTEN) activator selected from the group consisting of di-C8-phosphatidylinositol 4,5-P2 (PI(4,5)P2) and PI(5)P.

2. A method of treating wet age-related macular degeneration (AMD) in a mammal, the method comprising:
    identifying a mammal who has wet AMD; and
    administering to the mammal a therapeutically effective amount of one or both of:
    (i) an amp-activated protein kinase (AMPK) activator selected from the group consisting of 5-Aminoimidazole-4-carboxamide riboside (AICA riboside or AICAR); ZMP; guanidine; galegine; metformin (dimethylbiguanide); phemformin (phenethylbiguanide); antifolate drugs that inhibit AICAR transformylase; thiazolidinediones; phenobarbital; A-769662; PT1; and salicylate, wherein the AMPK activator is not methotrexate or rosiglitazone, or
    (ii) a Phosphatase and tensin homolog deleted on chromosome 10 (PTEN) activator selected from the group consisting of di-C8-phosphatidylinositol 4,5-P2 (PI(4,5)P2) and PI(5)P; and PPARgamma agonists.

3. A method of treating retinopathy, symptoms associated with microangiopathy, neovascular glaucoma, corneal graft rejection, glaucoma, herpetic and infectious keratitis, ocular ischemia, neovascular glaucoma, corneal, uveal and iris neovascularization, orbital and eyelid tumors, Stevens Johnson Syndrome, ocular cicatricial pemphigoid, wounds or other injuries, and ocular surface diseases in a mammal, the method comprising administering to a mammal in need thereof an effective amount of one or both of:
    (i) an amp-activated protein kinase (AMPK) activator selected from the group consisting of galegine; antifolate drugs that inhibit AICAR transformylase; phenobarbital; A-769662; PT1; and salicylate, wherein the AMPK activator is not methotrexate or rosiglitazone, or
    (ii) a Phosphatase and tensin homolog deleted on chromosome 10 (PTEN) activator selected from the group consisting of di-C8-phosphatidylinositol 4,5-P2 (PI(4,5)P2) and PI(5)P.

4. A method of treating a retinopathy selected from the group consisting of retinopathy of prematurity (ROP); retina vein occlusion; sickle cell retinopathy; Stargardt's disease; choroidal neovascularization; and radiation retinopathy in a mammal, the method comprising administering to a mammal in need thereof an effective amount of one or both of:
    (i) an amp-activated protein kinase (AMPK) activator selected from the group consisting of 5-Aminoimidazole-4-carboxamide riboside (AICA riboside or AICAR); ZMP; guanidine; galegine; metformin (dimethylbiguanide); phemformin (phenethylbiguanide); antifolate drugs that inhibit AICAR transfomylase; thiazolidinediones; phenobarbital; A-769662; PT1; and salicylate, wherein the AMPK activator or PTEN activator is not methotrexate or rosiglitazone, or
    (ii) a Phosphatase and tensin homolog deleted on chromosome 10 (PTEN) activator selected from the group consisting of di-C8-phosphatidylinositol 4,5-P2 (PI(4,5)P2) and PI(5)P.

5. The method of claim 3, wherein the injury is a chemical injury due to exposure to irritants, acids or bases.

6. The method of claim 1, wherein the mammal has endophthalmitis, macular edema, conjunctivitis, episcleritis, keratitis, optic neuritis, orbital pseudotumor, retinal vasculitis, or scleritis.

7. The method of claim 1, comprising administering a AMPK activator selected from the group consisting of guanidine; galegine; phenobarbital; A-769662; PT1; and salicylate.

8. The method of claim 1, comprising administering a PTEN activator selected from the group consisting of di-C8-phosphatidylinositol 4,5-P2 (PI(4,5)P2) and PI(5)P.

9. The method of claim 1, wherein the AMPK activator or PTEN activator is administered in combination with another treatment selected from the group consisting of anti VEGF therapies, non-steroidal or steroidal anti-inflammatory treatments, and neuroprotective treatments.

10. The method of claim 2, comprising administering a AMPK activator selected from the group consisting of 5-Aminoimidazole-4-carboxamide riboside (AICA riboside or AICAR); ZMP; guanidine; galegine; metformin (dimethylbiguanide); phemformin (phenethylbiguanide); pemetrexed; pioglitazone; troglitazone; phenobarbital; A-769662; PT1; and salicylate.

11. The method of claim 2, comprising administering a PTEN activator selected from the group consisting of di-C8-phosphatidylinositol 4,5-P2 (PI(4,5)P2) and PI(5)P.

12. The method of claim 2, wherein the AMPK activator or PTEN activator is administered in combination with another treatment selected from the group consisting of anti VEGF therapies, non-steroidal or steroidal anti-inflammatory treatments, and neuroprotective treatments.

* * * * *

UNITED STATES PATENT AND TRADEMARK OFFICE
CERTIFICATE OF CORRECTION

PATENT NO. : 10,143,703 B2
APPLICATION NO. : 15/108751
DATED : December 4, 2018
INVENTOR(S) : Demetrios Vavvas et al.

Page 1 of 1

It is certified that error appears in the above-identified patent and that said Letters Patent is hereby corrected as shown below:

On the Title Page

Column 2 (Abstract), Line 2, delete "agerelated" and insert -- age-related --,

In the Claims

In Column 33, Line 25, Claim 2, delete "phemformin" and insert -- phenformin --, In Column 34, Line 11, Claim 4, delete "phemformin" and insert -- phenformin --, In Column 34, Line 12, Claim 4, delete "transfomylase;" and insert -- transformylase; --, In Column 34, Line 28 (approx.), Claim 7, after "galegine;" insert -- pemetrexed; --, In Column 34, Line 42, Claim 10, delete "phemformin" and insert -- phenformin --.

Signed and Sealed this
Twenty-seventh Day of August, 2019

Andrei Iancu
*Director of the United States Patent and Trademark Office*